US012691063B1

(12) United States Patent
Muglia et al.

(10) Patent No.: US 12,691,063 B1
(45) Date of Patent: *Jul. 28, 2026

(54) METHODS OF USING RADIPRODIL IN THE TREATMENT OF DISORDERS

(71) Applicant: GRIN Therapeutics, Inc., New York, NY (US)

(72) Inventors: Pierandrea Muglia, Brussels (BE); Bruce Leuchter, New York, NY (US); Hans Christinger, New York, NY (US); Michael Panzara, New York, NY (US); Massimo Bani, New York, NY (US); Susan Paulson, New York, NY (US)

(73) Assignee: GRIN Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/336,122

(22) Filed: Sep. 22, 2025

Related U.S. Application Data

(63) Continuation of application No. 19/171,162, filed on Apr. 4, 2025, now Pat. No. 12,419,881, which is a continuation of application No. PCT/US2024/061589, filed on Dec. 20, 2024.

(60) Provisional application No. 63/691,887, filed on Sep. 6, 2024, provisional application No. 63/691,900, filed on Sep. 6, 2024, provisional application No. 63/612,997, filed on Dec. 20, 2023, provisional application No. 63/612,998, filed on Dec. 20, 2023.

(51) Int. Cl.

| | |
|---|---|
| ***A61K 31/454*** | (2006.01) |
| ***A61K 9/00*** | (2006.01) |
| ***A61K 9/10*** | (2006.01) |
| ***A61K 9/16*** | (2006.01) |
| ***A61P 25/08*** | (2006.01) |

(52) U.S. Cl.
CPC .............. *A61K 9/10* (2013.01); *A61K 9/0053* (2013.01); *A61K 9/1623* (2013.01); *A61K 9/1635* (2013.01); *A61K 9/1652* (2013.01); *A61K 9/1694* (2013.01); *A61K 31/454* (2013.01); *A61P 25/08* (2018.01)

(58) Field of Classification Search
CPC .................................................... A61K 31/454
USPC ......................................................... 514/326
See application file for complete search history.

(56) References Cited

U.S. PATENT DOCUMENTS 7,435,744 B2 10/2008 Domany et al.
9,387,212 B2 7/2016 Michel et al.
12,419,881 B1 * 9/2025 Muglia ................ A61K 9/1694
2004/0157886 A1 8/2004 Domany et al.
2010/0010044 A1 1/2010 Higuera et al.
2010/0048629 A1 2/2010 Gage
2010/0048630 A1 2/2010 Banerjee
2011/0190347 A1 8/2011 Gage
2011/0190348 A1 8/2011 Banerjee
2012/0059034 A1 * 3/2012 Demeter ................ A61P 25/36 546/198
2015/0157638 A1 * 6/2015 Michel ................ A61K 31/501 514/233.8
2016/0367560 A1 12/2016 Michel et al.
2022/0117951 A1 * 4/2022 Williams ............ A61K 31/454
2025/0127770 A1 4/2025 Genin et al.

FOREIGN PATENT DOCUMENTS

CA 3228004 A1 2/2023
WO WO-2003010159 A1 2/2003
WO WO-2010006020 A1 1/2010
WO WO-2010022300 A1 2/2010
WO WO-2010022304 A1 2/2010
WO WO-2010100512 A1 9/2010
WO WO-2012020270 A1 2/2012
WO WO-2013156614 A1 10/2013
WO WO-2017136375 A1 8/2017
WO WO-2020006629 A1 1/2020
WO WO-2020163966 A1 8/2020
WO WO-2021003553 A1 1/2021
WO WO-2023014956 A1 2/2023

OTHER PUBLICATIONS

Auvin et al., "Radiprodil, a NR2B negative allosteric modulator, from bench to bedside in infantile spasm syndrome" Annals of Clinical and Translational Neurology pp. 1-10 (2020). (Year: 2020).*
Anonymous, "An Open-label Adaptive Study for the Assessment of Safety, Tolerability, Pharmacokinetics, and Efficacy of Multiple Doses of Radiprodil in Subjects with Drug-resistant Infantile Spasms," EudraCT No. 2016-002107-26_Clinical trial results_EU Clinical Trials Register, XP093265333, Retrieved from the Internet: URL:https://www.clinicaltrialsregister.eu/ctr-search/trial/2016-002107-26/results, pp. 1-11 (Oct. 2018).
Anonymous, "Clinical Trials: Honeycomb: Evaluation of Radiprodil in Children with GRIN-related Disorder Record History," NCT05818943, Version 3, pp. 1-16, XP093265333, Retrieved from the Internet: URL:https://www.clinicaltrials.gov/study/NCT05818943?tab=history&a=3#version-content-panel (Oct. 2023).
Anonymous, "GRIN Therapeutics Announces First Patient Dosed in Phase 1B Clinical Trial with Radiprodil for Treatment of GRIN-related Disorders," First Word Pharma, Retrieved from the Internet: URL: https://firstwordpharma.com/story/5719, pp. 1-6, XP093265341 (Mar. 2023).

(Continued)

*Primary Examiner* — Raymond J Henley, III
(74) *Attorney, Agent, or Firm* — STERNE, KESSLER, GOLDSTEIN & FOX P.L.L.C.

(57) ABSTRACT

The present disclosure provides, in part, methods of treating an epileptic disorder in a pediatric subject in need thereof, comprising administering radiprodil to the pediatric subject; pharmaceutical compositions comprising radiprodil and pharmaceutically acceptable excipients and methods of use thereof in the treatment of disorders such as epileptic disorders.

30 Claims, 28 Drawing Sheets

(56) References Cited

OTHER PUBLICATIONS

Barta-Szalai, et al., "Oxamides as Novel NR2B Selective NMDA Receptor Antagonists," Bioorganic and Medicinal Chemistry Letters 14(15):3953-3956, Elsevier Science Ltd, United Kingdom (Aug. 2004).
Burge, M., et al., "The Anaesthetic Xenon Partially Restores an Amyloid Beta-induced Impairment in Murine Hippocampal Synaptic Plasticity," Neuropharmacology 151:21-32, Pergamon Press, United Kingdom (Jun. 2019).
Burger, P.B., et al., "Mapping the Binding of GluN2B-Selective N-methyl-D-aspartate Receptor Negative Allosteric Modulators," Molecular Pharmacology 82(2):344-359, Elsevier, Netherlands (Aug. 2012).
Fernandes, A., et al., "Inhibition of Invivo [3H] MK-801 Binding by NMDA Receptor Open Channel Blockers and GluN2B Antagonists in Rats and Mice," European Journal of Pharmacology 766:1-8 (2015).
Firaha, D., et al., "Predicting Crystal Form Stability Under Real-world Conditions," Nature 623(7986):324-328, Nature Publishing Group, United Kingdom (Nov. 2023).
ICH Harmonised Tripartite Guideline "Impurities in New Drug Products Q3B(R2)," International Conference on Harmonisation of Technical Requirements for Registration of Pharmaceuticals for Human Use; Current Step 4 version (Jun. 2006).
ICH Harmonized Guideline, "Assessment and Control of DNA Reactive (Mutagenic) Impurities in Pharmaceuticals to Limit Potential Carcinogenic Risk M7(R1)," Current Step 4 version (Mar. 2017).
"ICH Topic Q3A (R2) Impurities in New Drug Substances, ICH Step 5, Note for Guidance on Impurities Testing: Impurities in New Drug Substances," European Medicines Agency, Oct. 2006.
International Search Report and Written Opinion for International PCT Application No. PCT/US2022/039543 mailed on Nov. 25, 2022, 13 pages.
International Search Report and Written Opinion for International PCT Application No. PCT/US2024/061589 mailed on Jul. 22, 2025, 25 pages.
Johnson, T.N., et al., "Use of a Physiologically Based Pharmacokinetic-pharmacodynamic Model for Initial Dose Prediction and Escalation During a Paediatric Clinical Trial," British Journal of Clinical Pharmacology 87(3):1378-1389, Wiley-Blackwell, United Kingdom (Mar. 2021).
Labas, R., et al., "Synthesis, Evaluation and Metabolic Studies of Radiotracers Containing a 4-(4-[18F]-fluorobenzyl)piperidin-1-yl Moiety for the PET Imaging of NR2B NMDA Receptors," European Journal of Medicinal Chemistry 46:2295-2309 (Jun. 2011).
Marcin, L.R., et al., "BMS-986163, a Negative Allosteric Modulator of GluN2B with Potential Utility in Major Depressive Disorder," ACS Medicinal Chemistry Letters 9(5):472-477, American Chemical Society, United States (Apr. 2018).
Meglio, M., "Radiprodil Significantly Reduces Seizure Frequency in Phase 1b Honeycomb Study of GRIN-Related Neurodevelopmental Disorder," Retrieved from the Internet: URL: https://www.neurologylive.com/view/rad iprodil-significantly-reduces-seizure-frequency-phase-1b-honeycomb-study-grin-relate, pp. 1-5, XP093264883 (Sep. 2024).
Michel, A., et al., "Antiparkinsonian Effects of the "Radiprodil and Tozadenant" Combination in MPTP-treated Marmosets," PLoS One 12(8):e0182887, pp. 1-13, Public Library of Science, United States (Aug. 2017).
Michel, A., et al., "Behavioural Assessment of the A2a/NR2B Combination in the Unilateral 6-OHDA-Lesioned Rat Model: A New Method to Examine the Therapeutic Potential of Non-dopaminergic Drugs," PLoS One 10(8):e0135949, pp. 1-15, Public Library of Science, United States (Aug. 2015).
Michel, A., et al., "Unprecedented Therapeutic Potential With a Combination of A2A/NR2B Receptor Antagonists as Observed in the 6-OHDA Lesioned Rat Model of Parkinson's Disease," PLoS One 9(12):e114086, pp. 1-15, Public Library of Science, United States (Dec. 2014).
Muglia, P., "Radiprodil, a NR2B-NMDA Negative Allosteric Modulator, for GRIN-Related Disorder," Retrieved from Internet URL: https://www.youtube.com/watch?v=NDMruJOi9QE, XP093265212, pp. 1-20, (Jul. 2022).
Mullier, B., et al., "GRIN2B Gain of Function Mutations Are Sensitive to Radiprodil, a Negative Allosteric Modulator of GluN2B-containing NMDA Receptors," Neuropharmacology 123:322-331, Pergamon Press, United Kingdom (Sep. 2017).
Rammes, G., et al., "The NMDA Receptor Antagonist Radiprodil Reverses the Synaptotoxic Effects of Different Amyloid-beta (aβ) Species on Long-term Potentiation (LTP)," Neuropharmacology 140:184-192, Pergamon Press, United Kingdom (Sep. 2018).
Sciberras, D., et al., "A Pharmacokinetic Study of Radiprodil Oral Suspension in Healthy Adults Comparing Conventional Venous Blood Sampling with Two Microsampling Techniques," Pharmacology Research & Perspectives 7(1):e00459, John Wiley & Sons Ltd, United States (Jan. 2019).
Sidders, B., et al., "Network-based Drug Discovery: Coupling Network Pharmacology With Phenotypic Screening for Neuronal Excitability," Journal of Molecular Biology 430(18 Pt A):3005-3015, Elsevier, Netherlands (Sep. 2018).
Srikumar, B.N., et al., "Characterization of the Adrenocorticotrophic Hormone-Induced Mouse Model of Resistance to Antidepressant Drug Treatment," Pharmacology, Biochemistry, and Behavior 161:53-61, Elsevier, United States (Oct. 2017).
Van Der Aart, J., et al., "Evaluation of the Novel PET Tracer [11C]HACH242 for Imaging the GluN2B NMDA Receptor in Non-Human Primates," Molecular Imaging and Biology 21:676-685 (2019).

* cited by examiner

*One patient had not yet completed the maintenance period at the time these analyses were conducted. Dashed lines represent ≥50%, ≥90%, and 100% reductions from baseline in CMS frequency.

*One patient had not yet completed the maintenance period at the time these analyses were conducted. Dashed lines represent 80% and 90% seizure-free days.

*Six patients completed CGI baseline and end of maintenance period assessments at the time these analyses were conducted.

| Visit/Week | Screening Period (with 4-week observation) | Titration Period [a] | | | | | Maintenance Period | | | | UNS Visit / EOT [b] | Follow-up Visit [c] |
|---|---|---|---|---|---|---|---|---|---|---|---|---|
| | Screening | T1 / Week 1 | | T2 / Week 2 | T3 / Week 3 | T4 [d] / Week 4 | M1[e] / Week 1 | M2 / Week 2 | M3 / Week 6 | M4 [f,g,n] / Week 12 or EOS[c] | | |
| Timeframe [days] | Days -35 to -2 | -1 | t1 | (T1+7) +3 | (T2+7) +3 | (T3+7) +3 | m1 +3 | m15 ±3 | m43 ±3 | m85 ±3 | | 14 (+7) post last dose |
| (T)elemedicine or (H)ome Health Visit Allowed | | | | T | T | T | | T | | | | H |
| Written informed consent | X | | | | | | | | | | Unscheduled visits may be done at any time with assessments conducted as needed as clinically indicated. See Table 2-8 for associated PK sample. | |
| Inclusion/exclusion criteria | X | X | | | | | | | | | | |
| Sponsor eligibility review | X | | | | | | | | | | | |
| Feedback interview / questionnaire [b] | X [h] | | | | | | | | | X [i] (M4 only) | | |
| Demographics | X | | | | | | | | | | | |
| Medical/neurological history, including medications and procedures | X | | | | | | | | | | | |
| Physical / neurological examination [j] | X | X | | | | | X | | | X | | |
| Vital signs (blood pressure and pulse rate) [k] | X | X | X | | | | X | | X | X | | X |
| Height and weight [l] | X | X | | | | | X | | | X | | |
| ECG [m] | | X | | | | | X | | | X | | |
| V-EEG [b] | | X | | | | | | | | X [n] | | |
| Clinical laboratory tests [o] | X | X [p] | | | | | X | | | X | | X |
| Pregnancy test [q] | X | X | | | | | X | | | X | | |
| Distribute eDiary / instruct caregivers | X | | | | | | | | | | | |
| Check eDiary / records; retrain if needed | | X | | X | X | X | X | X | X | X | | |
| Randomization [r] | | X | | | | | | | | | | |
| Daily study drug dosing [s] | | | | | | | | | | | | |
| Blood sampling for PK [t] | | | X | | | | X | | | X [t] | | |

FIG. 7A

| Visit/Week | Screening Period with 4-week observation) | Titration Period [a] | | | | | Maintenance Period | | | | UNS Visit / EOT [b] | Follow-up Visit [c] |
|---|---|---|---|---|---|---|---|---|---|---|---|---|
| | Screening | T1 / Week 1 | | T2 / Week 2 | T3 / Week 3 | T4 [d] / Week 4 | M1[e] / Week 1 | M2 / Week 2 | M3 / Week 6 | M4 [f,g,n] / Week 12 or EOS[c] | | |
| Timeframe [days] | Days -35 to -2 | -1 | t1 | (T1+7) +3 | (T2+7) +3 | (T3+7) +3 | m1 +3 | m15 ±3 | m43 ±3 | m85 ±3 | | 14 (+7) post last dose |
| (T)elemedicine or (H)ome Health Visit Allowed | | | | T | T | T | | T | | | | H |
| Blood sampling for metabolites [t] | | | | | | | | | | X | | |
| VABS-3 [u] | | X | | | | | | | | X | | |
| ORCA [v] | | X | | | | | | | | X | | |
| CGI-S | X | X | | | | | X | | X | X | | |
| CGI-C | | | | | | | X | | X | X | | |
| ABC-2C [w] | | X | | | | | | | | X | | |
| PedsQL [w] | | X | | | | | | | | X | | |
| Suicidality assessments [x] | X | X | | | | | | | | X | | |
| Submission of SIF to ESCI (if applicable) [y] | X | → | | | | | | | | | | |
| Concomitant medications [z] | X | → | | | | | | | | | | |
| AEs | X | → | | | | | | | | | | |

Abbreviations: ABC-2C = aberrant behavior checklist-community; AE = adverse event; BID = twice daily (bis in die); CGI-C = Clinical Global Impression of Change scale; CGI-S = Clinical Global Impression - Severity scale; C-SSRS = Columbia-Suicide Severity Rating Scale; ECG = electrocardiogram; eCRF = electronic case report form; eDiary = electronic diary; EOS = End of Study; EOT = End of Treatment; ESCI = Epilepsy Study Consortium; m = Maintenance Period study day; M = Maintenance Period Visit; ORCA = Observer-reported Communication Ability; PedsQL = Pediatric Quality of Life Inventory; PK = pharmacokinetics; SIF = seizure identification form; t = Titration Period study day; T = Titration Period Visit; UNS = unscheduled; V-EEG = video electroencephalogram; VABS-3 = Vineland Adaptive Behavior Scale, Third Edition Note 1: Telemedicine visits must be led by the investigator or sub-investigator, conducted as per local regulations, and documented in the participant's medical record. Details regarding the coordination and conduct of Home Health visits will be provided.

Note 2: Participants who discontinue treatment early will be encouraged to remain on study to complete visits and assessments as per the study schedule until they choose to withdraw or otherwise meet criteria to discontinue from study (see Section 8.3.2).

a. For the first dose, participants will stay at the site for a minimum of 1 day with the potential for overnight stays up to 3 days. For Visits T2, T3, and T4, if visits occur on-site, an overnight stay (or hotel stay) before and after the titration day is allowed as deemed necessary based on practical considerations and taking into account participant and caregiver preference.

b. Unscheduled visits may be conducted as needed with the option to use telemedicine visit technology if medically indicated. If the participant discontinues treatment early, an unscheduled visit will be conducted at the site with assessments selected by the investigator as clinically appropriate. The unscheduled end of treatment visit must include a V-EEG assessment if the participant stopped treatment during the Maintenance Period though this is not required if treatment is discontinued prior to Visit M1. If possible with consideration to participant safety, the unscheduled visit and V-EEG (if required) should be conducted before beginning taper of study drug

FIG. 7B (recommendations in Section 7.1.3). A feedback interview will be conducted within +5 days of the unscheduled end of treatment visit. If a participant will continue with study visits and assessments after discontinuation of treatment, V-EEGs and interviews beyond the unscheduled end of treatment visit are NOT required.

Figure 7C:
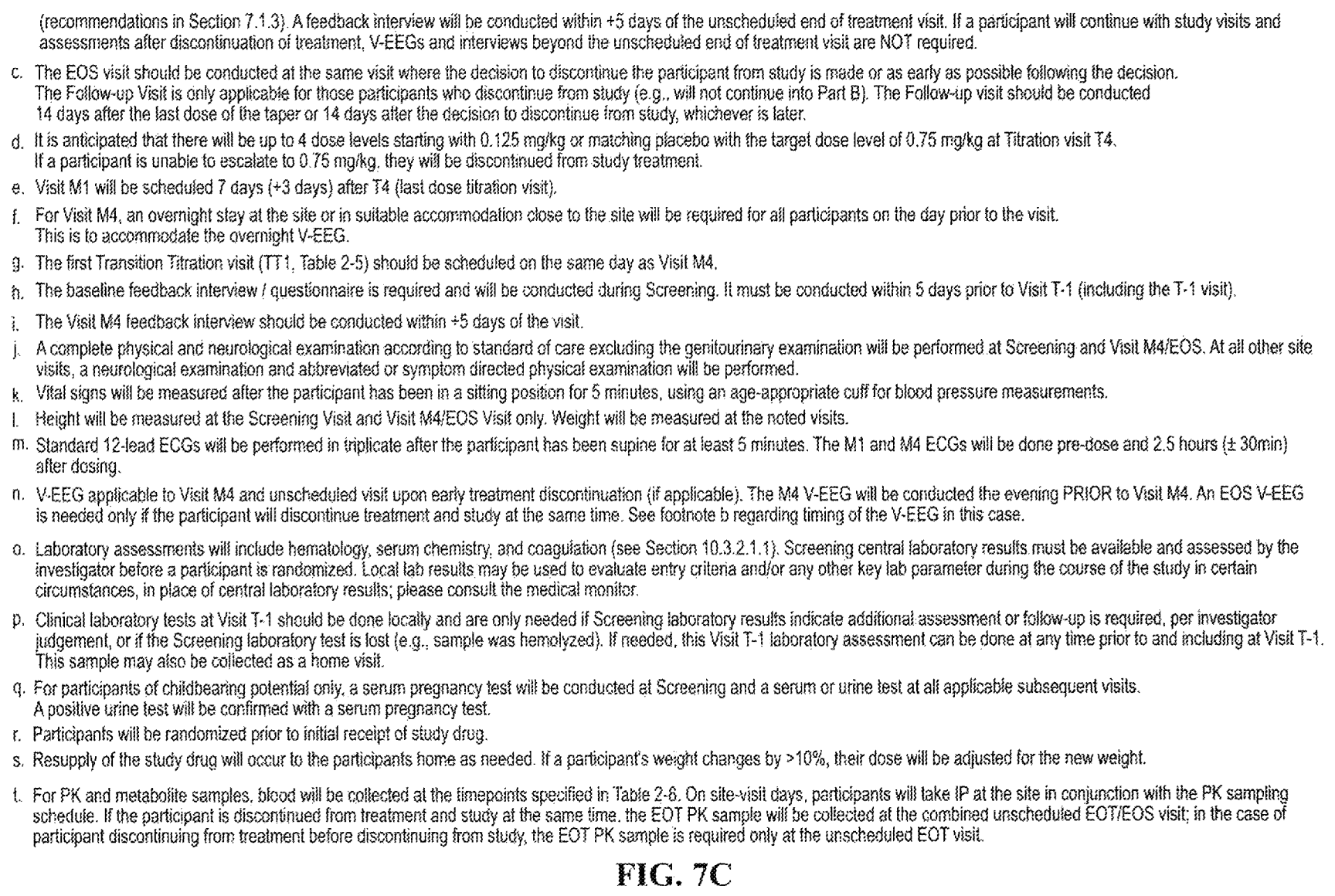

c. The EOS visit should be conducted at the same visit where the decision to discontinue the participant from study is made or as early as possible following the decision. The Follow-up Visit is only applicable for those participants who discontinue from study (e.g., will not continue into Part B). The Follow-up visit should be conducted 14 days after the last dose of the taper or 14 days after the decision to discontinue from study, whichever is later.

d. It is anticipated that there will be up to 4 dose levels starting with 0.125 mg/kg or matching placebo with the target dose level of 0.75 mg/kg at Titration visit T4. If a participant is unable to escalate to 0.75 mg/kg, they will be discontinued from study treatment.

e. Visit M1 will be scheduled 7 days (+3 days) after T4 (last dose titration visit).

f. For Visit M4, an overnight stay at the site or in suitable accommodation close to the site will be required for all participants on the day prior to the visit. This is to accommodate the overnight V-EEG.

g. The first Transition Titration visit (TT1, Table 2-5) should be scheduled on the same day as Visit M4.

h. The baseline feedback interview / questionnaire is required and will be conducted during Screening. It must be conducted within 5 days prior to Visit T-1 (including the T-1 visit).

i. The Visit M4 feedback interview should be conducted within +5 days of the visit.

j. A complete physical and neurological examination according to standard of care excluding the genitourinary examination will be performed at Screening and Visit M4/EOS. At all other site visits, a neurological examination and abbreviated or symptom directed physical examination will be performed.

k. Vital signs will be measured after the participant has been in a sitting position for 5 minutes, using an age-appropriate cuff for blood pressure measurements.

l. Height will be measured at the Screening Visit and Visit M4/EOS Visit only. Weight will be measured at the noted visits.

m. Standard 12-lead ECGs will be performed in triplicate after the participant has been supine for at least 5 minutes. The M1 and M4 ECGs will be done pre-dose and 2.5 hours (± 30min) after dosing.

n. V-EEG applicable to Visit M4 and unscheduled visit upon early treatment discontinuation (if applicable). The M4 V-EEG will be conducted the evening PRIOR to Visit M4. An EOS V-EEG is needed only if the participant will discontinue treatment and study at the same time. See footnote b regarding timing of the V-EEG in this case.

o. Laboratory assessments will include hematology, serum chemistry, and coagulation (see Section 10.3.2.1.1). Screening central laboratory results must be available and assessed by the investigator before a participant is randomized. Local lab results may be used to evaluate entry criteria and/or any other key lab parameter during the course of the study in certain circumstances, in place of central laboratory results; please consult the medical monitor.

p. Clinical laboratory tests at Visit T-1 should be done locally and are only needed if Screening laboratory results indicate additional assessment or follow-up is required, per investigator judgement, or if the Screening laboratory test is lost (e.g., sample was hemolyzed). If needed, this Visit T-1 laboratory assessment can be done at any time prior to and including at Visit T-1. This sample may also be collected as a home visit.

q. For participants of childbearing potential only, a serum pregnancy test will be conducted at Screening and a serum or urine test at all applicable subsequent visits. A positive urine test will be confirmed with a serum pregnancy test.

r. Participants will be randomized prior to initial receipt of study drug.

s. Resupply of the study drug will occur to the participants home as needed. If a participant's weight changes by >10%, their dose will be adjusted for the new weight.

t. For PK and metabolite samples, blood will be collected at the timepoints specified in Table 2-6. On site-visit days, participants will take IP at the site in conjunction with the PK sampling schedule. If the participant is discontinued from treatment and study at the same time, the EOT PK sample will be collected at the combined unscheduled EOT/EOS visit; in the case of participant discontinuing from treatment before discontinuing from study, the EOT PK sample is required only at the unscheduled EOT visit.

FIG. 7C u. The VABS-3 will be centrally and virtually administered up to 5 days before the scheduled visit day or on the day of the visit if not done before hand, preferably early during the visit. The rater will be blinded to the participant's treatment assignment and cohort.

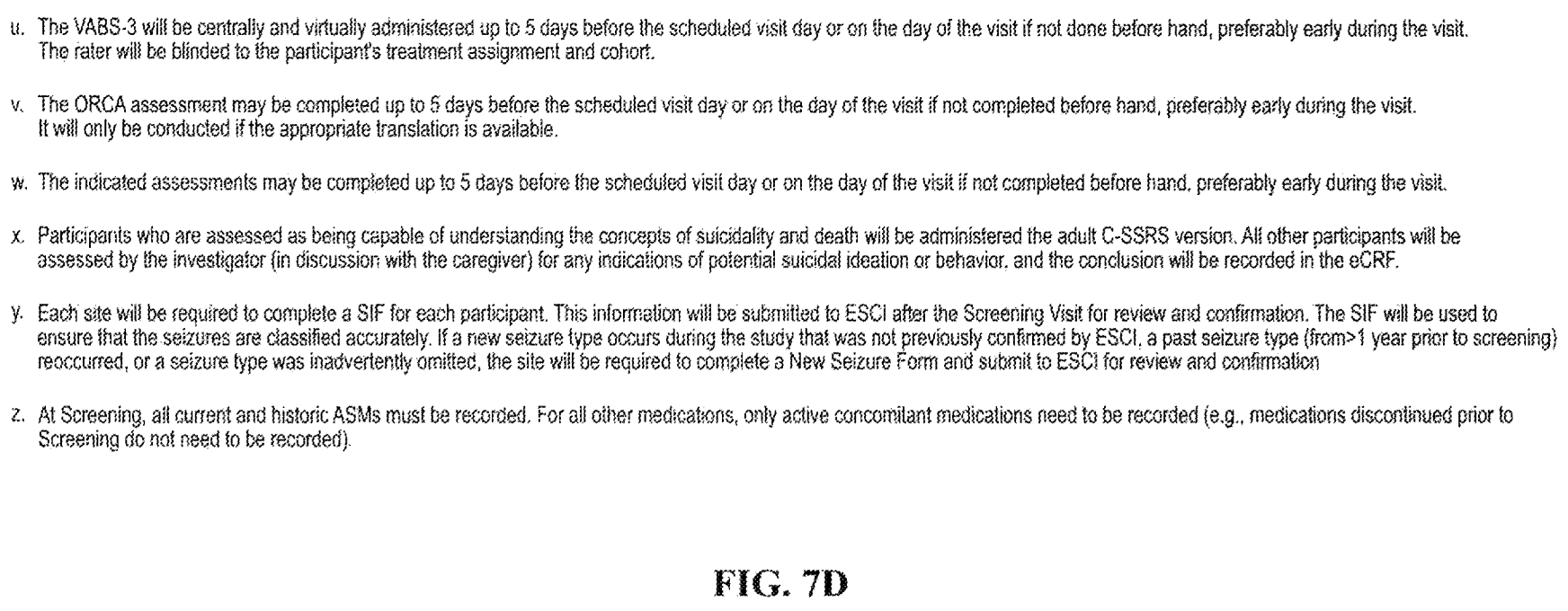

v. The ORCA assessment may be completed up to 5 days before the scheduled visit day or on the day of the visit if not completed before hand, preferably early during the visit. It will only be conducted if the appropriate translation is available.

w. The indicated assessments may be completed up to 5 days before the scheduled visit day or on the day of the visit if not completed before hand, preferably early during the visit.

x. Participants who are assessed as being capable of understanding the concepts of suicidality and death will be administered the adult C-SSRS version. All other participants will be assessed by the investigator (in discussion with the caregiver) for any indications of potential suicidal ideation or behavior, and the conclusion will be recorded in the eCRF.

y. Each site will be required to complete a SIF for each participant. This information will be submitted to ESCI after the Screening Visit for review and confirmation. The SIF will be used to ensure that the seizures are classified accurately. If a new seizure type occurs during the study that was not previously confirmed by ESCI, a past seizure type (from>1 year prior to screening) reoccurred, or a seizure type was inadvertently omitted, the site will be required to complete a New Seizure Form and submit to ESCI for review and confirmation z. At Screening, all current and historic ASMs must be recorded. For all other medications, only active concomitant medications need to be recorded (e.g., medications discontinued prior to Screening do not need to be recorded).

FIG. 7D

| Visit/Week | Screening Period | Titration Period [a] | | | | | End of Study (EOS) [d] | UNS Visit / EOT [c] | Follow-up Visit [d] |
|---|---|---|---|---|---|---|---|---|---|
| | | T1 / Week 1 | | T2 / Week 2 | T3 / Week 3 | T4 [b,e] / Week 4 | | | |
| Timeframe [days] | Days - 35 to - 2 | -1 | t1 | (T1+7) +3 | (T2+7) +3 | (T3+7) +3 | | | 14 (+7) post last dose |
| (T)elemedicine or (H)ome Health Visit Allowed | | | | T | T | T | | | H |
| Written informed consent | X | | | | | | | Unscheduled visits may be done at any time with assessments conducted as needed as clinically indicated. See Table 2-8 for associated PK sample. | |
| Inclusion/exclusion criteria | X | X | | | | | | | |
| Sponsor eligibility review | X | | | | | | | | |
| Feedback interview / questionnaire [c] | X [f] | | | | | | | | |
| Demographics | X | | | | | | | | |
| Medical / neurological history, including medications / procedures | X | | | | | | | | |
| Physical / neurological examination [g] | X | X | | | | | X | | |
| Vital signs (blood pressure and pulse rate) [h] | X | X | X | | | | X | | X |
| Height and weight [i] | X | X | | | | | X | | |
| ECG [j] | | X | | | | | X | | |
| V-EEG [c] | | X | | | | | | | |
| Clinical laboratory tests [k] | X | X [1] | | | | | X | | X |
| Pregnancy test [m] | X | X | | | | | X | | |
| Distribute eDiary / instruct caregivers | X | | | | | | | | |
| Check eDiary / records; retrain if needed | | X | | X | X | X | X | | |
| Randomization [n] | | X | | | | | | | |
| Daily study drug dosing [o] | | | → | → | → | → | | | |
| Blood sampling for PK [p] | | | X | | | | X [p] | | |

FIG. 8A

| Visit/Week | Screening Period | Titration Period [a] | | | | | End of Study (EOS) [d] | UNS Visit / EOT [c] | Follow-up Visit [d] |
|---|---|---|---|---|---|---|---|---|---|
| | | T1 / Week 1 | | T2 / Week 2 | T3 / Week 3 | T4 [b,e] / Week 4 | | | |
| Timeframe [days] | Days - 35 to - 2 | -1 | t1 | (T1+7) +3 | (T2+7) +3 | (T3+7) +3 | | | 14 (+7) post last dose |
| (T)elemedicine or (H)ome Health Visit Allowed | | | | T | T | T | | | H |
| VABS-3 [q] | | X | | | | | X | | |
| ORCA [r] | | X | | | | | X | | |
| CGI-S | X | X | | | | | X | | |
| CGI-C | | | | | | | X | | |
| ABC-2C [s] | | X | | | | | X | | |
| PedsQL [s] | | X | | | | | X | | |
| Suicidality assessment [t] | X | X | | | | | X | | |
| Submission of SIF to ESCI (if applicable) [u] | X | → | → | → | → | → | → | → | → |
| Concomitant medications [v] | X | → | → | → | → | → | → | → | → |
| AEs | X | → | → | → | → | → | → | → | → |

Abbreviations: ABC-2C = aberrant behavior checklist-community; AE = adverse event; BID = twice daily (bis in die); CGI-C = Clinical Global Impression of Change scale; CGI-S = Clinical Global Impression - Severity scale; C-SSRS = Columbia-Suicide Severity Rating Scale; ECG = electrocardiogram; eCRF = electronic case report form; eDiary = electronic diary; EOS = End of Study; EOT = End of Treatment; ESCI = Epilepsy Study Consortium; m = Maintenance Period study day; M = Maintenance Period Visit; ORCA = Observer-reported Communication Ability; PedsQL = Pediatric Quality of Life Inventory; PK = pharmacokinetics; SIF = seizure identification form; t = Titration Period study day; T = Titration Period Visit; V-EEG = video electroencephalogram; VABS-3 = Vineland Adaptive Behavior Scale; Third Edition Note 1: Telemedicine visits must be led by the Investigator or sub-investigator, conducted as per local regulations, and documented in the participant's medical record. Details regarding the coordination and conduct of Home Health visits will be provided.

Note 2: Participants who discontinue treatment early will be encouraged to remain on study to complete visits and assessments as per the study schedule until they choose to withdraw or otherwise meet criteria to discontinue from study (see Section 8.3.2).

Figure 8C:
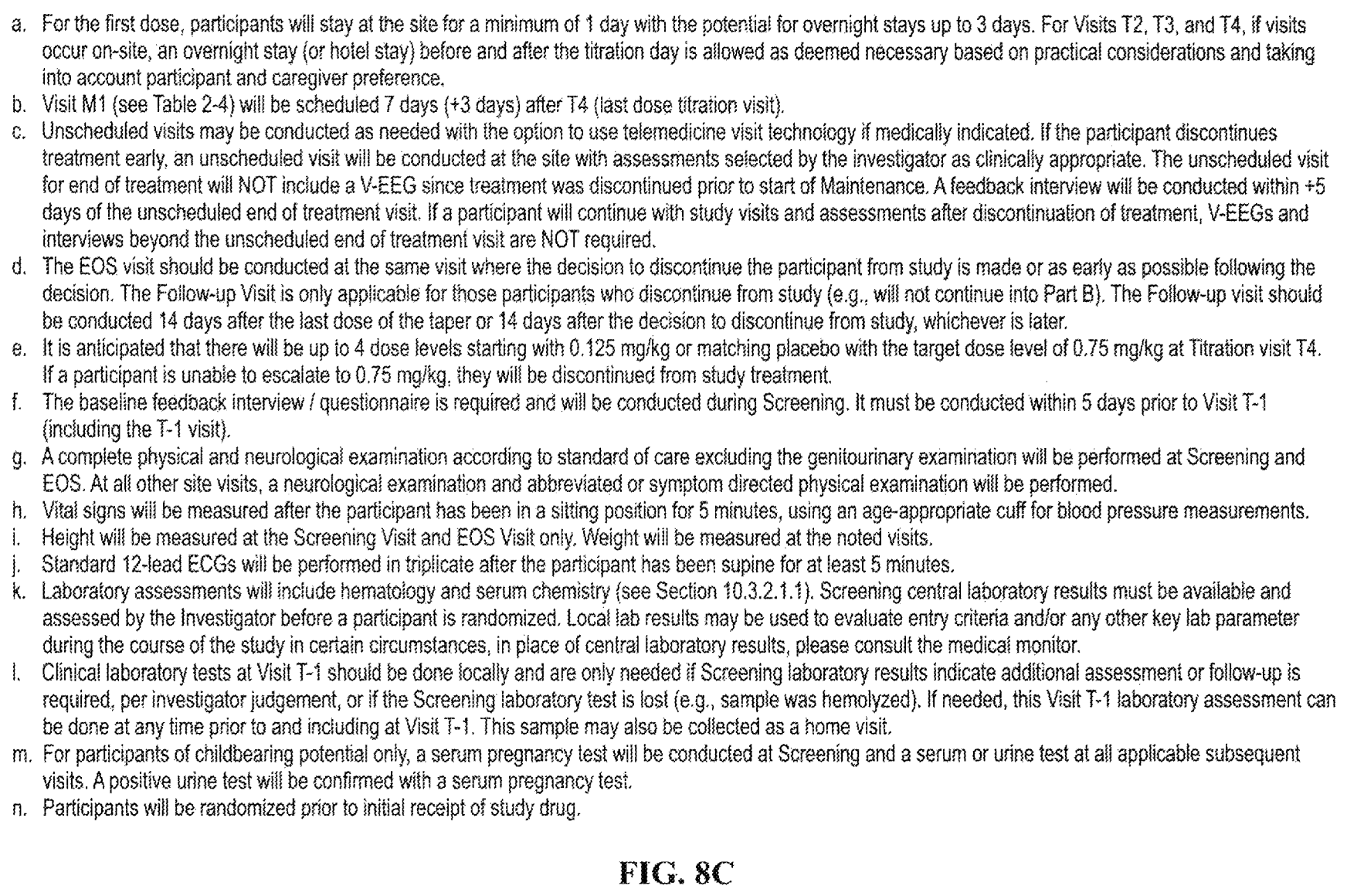

FIG. 8B a. For the first dose, participants will stay at the site for a minimum of 1 day with the potential for overnight stays up to 3 days. For Visits T2, T3, and T4, if visits occur on-site, an overnight stay (or hotel stay) before and after the titration day is allowed as deemed necessary based on practical considerations and taking into account participant and caregiver preference.
b. Visit M1 (see Table 2-4) will be scheduled 7 days (+3 days) after T4 (last dose titration visit).
c. Unscheduled visits may be conducted as needed with the option to use telemedicine visit technology if medically indicated. If the participant discontinues treatment early, an unscheduled visit will be conducted at the site with assessments selected by the investigator as clinically appropriate. The unscheduled visit for end of treatment will NOT include a V-EEG since treatment was discontinued prior to start of Maintenance. A feedback interview will be conducted within +5 days of the unscheduled end of treatment visit. If a participant will continue with study visits and assessments after discontinuation of treatment, V-EEGs and interviews beyond the unscheduled end of treatment visit are NOT required.
d. The EOS visit should be conducted at the same visit where the decision to discontinue the participant from study is made or as early as possible following the decision. The Follow-up Visit is only applicable for those participants who discontinue from study (e.g., will not continue into Part B). The Follow-up visit should be conducted 14 days after the last dose of the taper or 14 days after the decision to discontinue from study, whichever is later.
e. It is anticipated that there will be up to 4 dose levels starting with 0.125 mg/kg or matching placebo with the target dose level of 0.75 mg/kg at Titration visit T4. If a participant is unable to escalate to 0.75 mg/kg, they will be discontinued from study treatment.
f. The baseline feedback interview / questionnaire is required and will be conducted during Screening. It must be conducted within 5 days prior to Visit T-1 (including the T-1 visit).
g. A complete physical and neurological examination according to standard of care excluding the genitourinary examination will be performed at Screening and EOS. At all other site visits, a neurological examination and abbreviated or symptom directed physical examination will be performed.
h. Vital signs will be measured after the participant has been in a sitting position for 5 minutes, using an age-appropriate cuff for blood pressure measurements.
i. Height will be measured at the Screening Visit and EOS Visit only. Weight will be measured at the noted visits.
j. Standard 12-lead ECGs will be performed in triplicate after the participant has been supine for at least 5 minutes.
k. Laboratory assessments will include hematology and serum chemistry (see Section 10.3.2.1.1). Screening central laboratory results must be available and assessed by the Investigator before a participant is randomized. Local lab results may be used to evaluate entry criteria and/or any other key lab parameter during the course of the study in certain circumstances, in place of central laboratory results, please consult the medical monitor.
l. Clinical laboratory tests at Visit T-1 should be done locally and are only needed if Screening laboratory results indicate additional assessment or follow-up is required, per investigator judgement, or if the Screening laboratory test is lost (e.g., sample was hemolyzed). If needed, this Visit T-1 laboratory assessment can be done at any time prior to and including at Visit T-1. This sample may also be collected as a home visit.
m. For participants of childbearing potential only, a serum pregnancy test will be conducted at Screening and a serum or urine test at all applicable subsequent visits. A positive urine test will be confirmed with a serum pregnancy test.
n. Participants will be randomized prior to initial receipt of study drug.

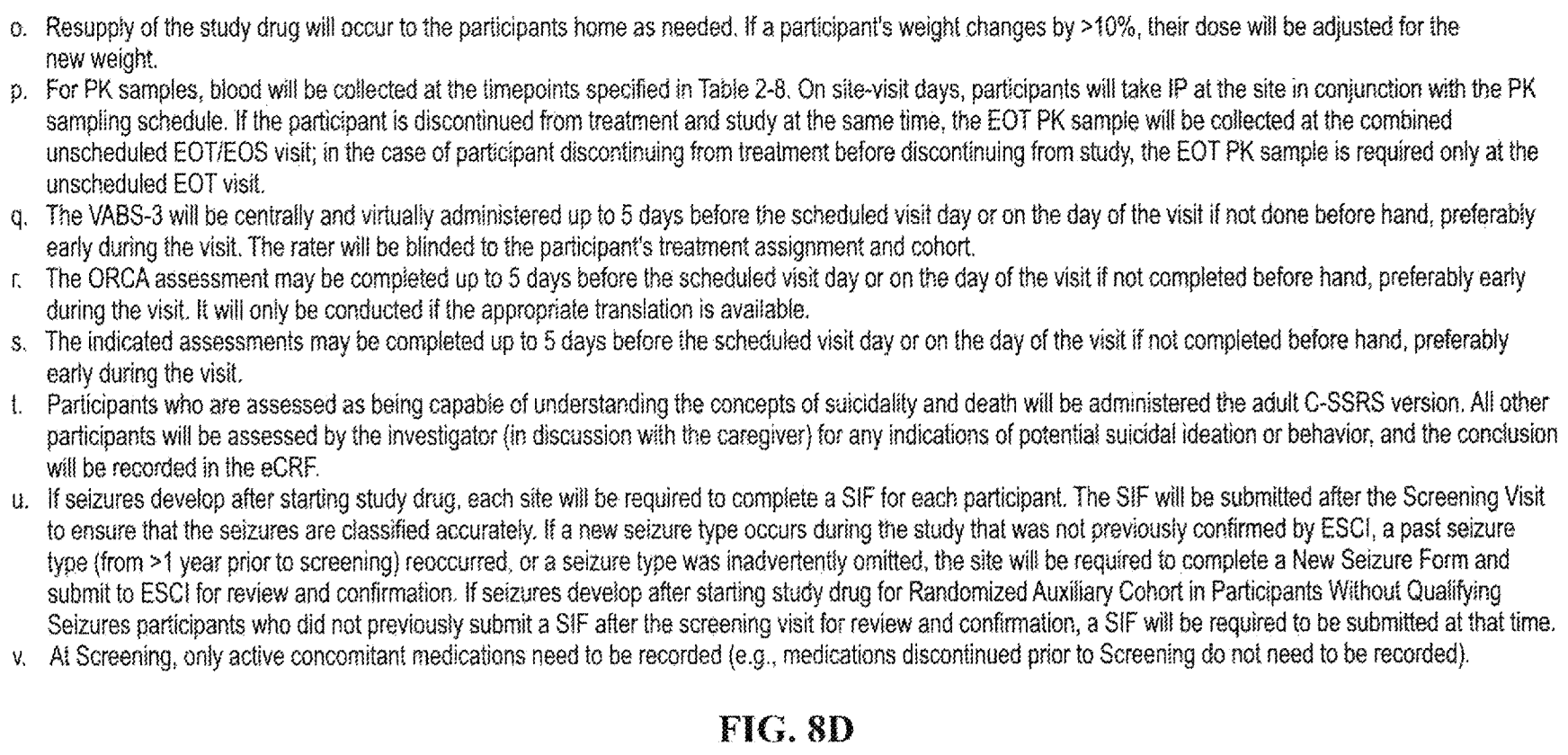

FIG. 8C o. Resupply of the study drug will occur to the participants home as needed. If a participant's weight changes by >10%, their dose will be adjusted for the new weight.
p. For PK samples, blood will be collected at the timepoints specified in Table 2-8. On site-visit days, participants will take IP at the site in conjunction with the PK sampling schedule. If the participant is discontinued from treatment and study at the same time, the EOT PK sample will be collected at the combined unscheduled EOT/EOS visit; in the case of participant discontinuing from treatment before discontinuing from study, the EOT PK sample is required only at the unscheduled EOT visit.
q. The VABS-3 will be centrally and virtually administered up to 5 days before the scheduled visit day or on the day of the visit if not done before hand, preferably early during the visit. The rater will be blinded to the participant's treatment assignment and cohort.
r. The ORCA assessment may be completed up to 5 days before the scheduled visit day or on the day of the visit if not completed before hand, preferably early during the visit. It will only be conducted if the appropriate translation is available.
s. The indicated assessments may be completed up to 5 days before the scheduled visit day or on the day of the visit if not completed before hand, preferably early during the visit.
t. Participants who are assessed as being capable of understanding the concepts of suicidality and death will be administered the adult C-SSRS version. All other participants will be assessed by the investigator (in discussion with the caregiver) for any indications of potential suicidal ideation or behavior, and the conclusion will be recorded in the eCRF.
u. If seizures develop after starting study drug, each site will be required to complete a SIF for each participant. The SIF will be submitted after the Screening Visit to ensure that the seizures are classified accurately. If a new seizure type occurs during the study that was not previously confirmed by ESCI, a past seizure type (from >1 year prior to screening) reoccurred, or a seizure type was inadvertently omitted, the site will be required to complete a New Seizure Form and submit to ESCI for review and confirmation. If seizures develop after starting study drug for Randomized Auxiliary Cohort in Participants Without Qualifying Seizures participants who did not previously submit a SIF after the screening visit for review and confirmation, a SIF will be required to be submitted at that time.
v. At Screening, only active concomitant medications need to be recorded (e.g., medications discontinued prior to Screening do not need to be recorded).

FIG. 8D

| | Maintenance Period[a] | | | | | | | | Follow-up Period[b] |
|---|---|---|---|---|---|---|---|---|---|
| Visit/Week | M1[c] / Week 1 | M1[c] / Week 1 | M1[c] / Week 1 | M1[c] / Week 1 | M1[c] / Week 1 | M1[c] / Week 1 | M1[c] / Week 1 | M8[e,f] / Week 24 or ET[b] | |
| Timeframe [days] | m1+3 | m15±3 | m29±3 | m57±3 | m85±3 | m113±14 | m141±14 | m169±14 | 14 (+7) post last dose |
| Participant feedback interview / questionnaire | | | | | | | | X | X |
| Demographics | | | | | | | | | |
| Physical / neurological examination[g] | | | | | X | | | X | |
| Vital signs (blood pressure and pulse rate)[h] | X | | X | | X | | | X | X |
| Height and weight[i] | X | | X | | X | | | X | |
| ECG[j] | X | | | | X | | | X | |
| V-EEG | | | | | | | | X | |
| Clinical laboratory tests[k] | X | | | | X | | | X | X |
| Pregnancy test[l] | X | | X | | X | | | X | |
| Check participant's eDiary and records and provide eDiary retraining if necessary | X | X | X | X | X | X | X | X | |
| Daily study drug administration[m] | → | | | | | | | | |
| Blood sampling for PK[n] | X | | | | | | | X | |
| Vineland-3[o] | | | | | X | | | X | |
| CGI-C | | | | | X | | | X | |
| ABC-C | | | | | X | | | X | |
| PedsQL | | | | | X | | | X | |
| CaGI-C | | | | | X | | | X | |
| Suicidality assessment[p] | | | | | X | | | X | |
| Submission of SIF to ESCI (if applicable)[q] | → | | | | | | | | |
| Concomitant medications | → | | | | | | | | |
| AEs | → | | | | | | | | |

FIG. 9A

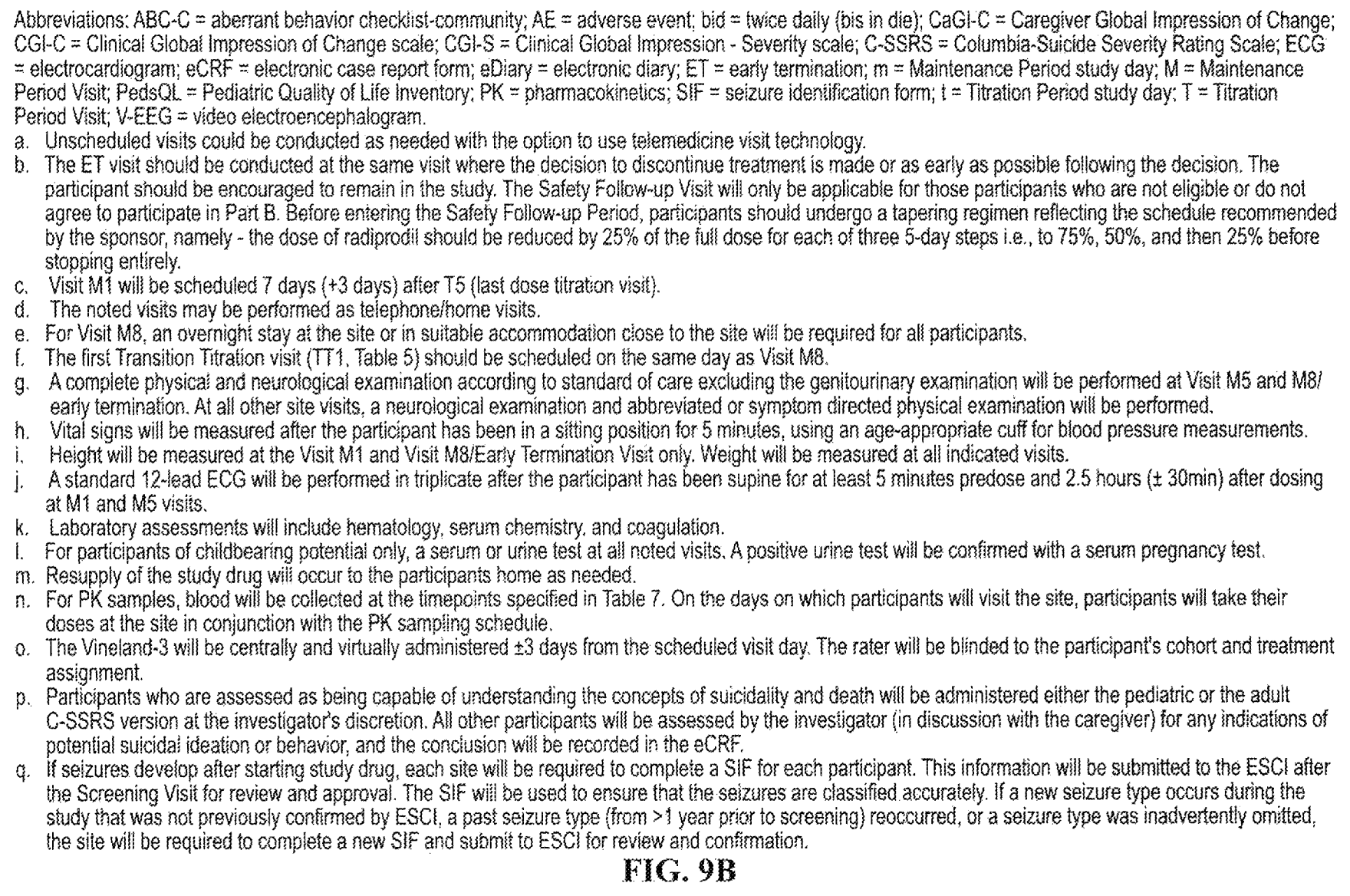

Abbreviations: ABC-C = aberrant behavior checklist-community; AE = adverse event; bid = twice daily (bis in die); CaGI-C = Caregiver Global Impression of Change; CGI-C = Clinical Global Impression of Change scale; CGI-S = Clinical Global Impression - Severity scale; C-SSRS = Columbia-Suicide Severity Rating Scale; ECG = electrocardiogram; eCRF = electronic case report form; eDiary = electronic diary; ET = early termination; m = Maintenance Period study day; M = Maintenance Period Visit; PedsQL = Pediatric Quality of Life Inventory; PK = pharmacokinetics; SIF = seizure identification form; t = Titration Period study day; T = Titration Period Visit; V-EEG = video electroencephalogram.

a. Unscheduled visits could be conducted as needed with the option to use telemedicine visit technology.
b. The ET visit should be conducted at the same visit where the decision to discontinue treatment is made or as early as possible following the decision. The participant should be encouraged to remain in the study. The Safety Follow-up Visit will only be applicable for those participants who are not eligible or do not agree to participate in Part B. Before entering the Safety Follow-up Period, participants should undergo a tapering regimen reflecting the schedule recommended by the sponsor, namely - the dose of radiprodil should be reduced by 25% of the full dose for each of three 5-day steps i.e., to 75%, 50%, and then 25% before stopping entirely.
c. Visit M1 will be scheduled 7 days (+3 days) after T5 (last dose titration visit).
d. The noted visits may be performed as telephone/home visits.
e. For Visit M8, an overnight stay at the site or in suitable accommodation close to the site will be required for all participants.
f. The first Transition Titration visit (TT1, Table 5) should be scheduled on the same day as Visit M8.
g. A complete physical and neurological examination according to standard of care excluding the genitourinary examination will be performed at Visit M5 and M8/ early termination. At all other site visits, a neurological examination and abbreviated or symptom directed physical examination will be performed.
h. Vital signs will be measured after the participant has been in a sitting position for 5 minutes, using an age-appropriate cuff for blood pressure measurements.
i. Height will be measured at the Visit M1 and Visit M8/Early Termination Visit only. Weight will be measured at all indicated visits.
j. A standard 12-lead ECG will be performed in triplicate after the participant has been supine for at least 5 minutes predose and 2.5 hours (± 30min) after dosing at M1 and M5 visits.
k. Laboratory assessments will include hematology, serum chemistry, and coagulation.
l. For participants of childbearing potential only, a serum or urine test at all noted visits. A positive urine test will be confirmed with a serum pregnancy test.
m. Resupply of the study drug will occur to the participants home as needed.
n. For PK samples, blood will be collected at the timepoints specified in Table 7. On the days on which participants will visit the site, participants will take their doses at the site in conjunction with the PK sampling schedule.
o. The Vineland-3 will be centrally and virtually administered ±3 days from the scheduled visit day. The rater will be blinded to the participant's cohort and treatment assignment.
p. Participants who are assessed as being capable of understanding the concepts of suicidality and death will be administered either the pediatric or the adult C-SSRS version at the investigator's discretion. All other participants will be assessed by the investigator (in discussion with the caregiver) for any indications of potential suicidal ideation or behavior, and the conclusion will be recorded in the eCRF.
q. If seizures develop after starting study drug, each site will be required to complete a SIF for each participant. This information will be submitted to the ESCI after the Screening Visit for review and approval. The SIF will be used to ensure that the seizures are classified accurately. If a new seizure type occurs during the study that was not previously confirmed by ESCI, a past seizure type (from >1 year prior to screening) reoccurred, or a seizure type was inadvertently omitted, the site will be required to complete a new SIF and submit to ESCI for review and confirmation.

FIG. 9B

| Timeframe [d] | Transition Titration | Baseline [a] | Screening/ Baseline Phase 1b [b] | Treatment Period [c,d] (to be Repeated for Each Further Year of Study Participation) | | | | | | | | Follow-up Period (EOS/ET) [d] |
|---|---|---|---|---|---|---|---|---|---|---|---|---|
| | | Day 1 | Day 1 [e,g] | Phone Calls (Months 1 and 2) [f] | Month 3 [e] | Phone Calls (Months 4 and 5) [f] | Month 6 [e] | Phone Calls (Months 7 and 8) [f] | Month 9 [e] | Phone Calls (Months 10 and 11) [f] | Month 12 [e] etc. | 14 Days After Last Dose |
| **Visit window [days]** | | - | - | ±14 | ±14 | ±14 | ±14 | ±14 | ±14 | ±14 | ±14 | ±7 |
| Eligibility reconfirmation | | X | X | | | | | | | | | |
| Participant feedback interview / questionnaire | | | | | | | X | | | | | X |
| Demographics | | | | | | | | | | | | |
| Medical / neurological history, including medications and procedures | | X [g] | X | | | | | | | | | |
| Physical / neurological examination | | X [g] | X | | X | | X | | X | | X | |
| Vital signs (blood pressure and pulse rate) [h] | | X [g] | X | | X | | X | | X | | X | X |
| Height, weight [i], and BMI | | X [g] | X | | X | | X | | X | | X | |
| ECG [j] | | X [g] | X | | X | | | | | | | |
| V-EEG [k] | | | X | | X | | | | X | | | X |
| Clinical laboratory tests [l] | | X [g] | X | | X | | X | | X | | X | X |
| Pregnancy test [m] | | X [g] | X | | X | | X | | X | | X | |
| Distribute eDiary | | X | X | | | | | | | | | |

FIG. 10A

| Timeframe [d] | Transition Titration | Baseline [a] | Screening/ Baseline Phase 1b [b] | Treatment Period [c,d] (to be Repeated for Each Further Year of Study Participation) | | | | | | | | Follow-up Period (EOS/ET) [d] |
|---|---|---|---|---|---|---|---|---|---|---|---|---|
| | | Day 1 | Day 1 [e,g] | Phone Calls (Months 1 and 2) [f] | Month 3 [e] | Phone Calls (Months 4 and 5) [f] | Month 6 [e] | Phone Calls (Months 7 and 8) [f] | Month 9 [e] | Phone Calls (Months 10 and 11) [f] | Month 12 [e] etc. | 14 Days After Last Dose |
| **Visit window [days]** | | - | - | ±14 | ±14 | ±14 | ±14 | ±14 | ±14 | ±14 | ±14 | ±7 |
| Check eDiary records / retrain if necessary [n] | | | | X | X | X | X | X | X | X | X | |
| Return of eDiary | | | | | | | | | | | | X |
| Daily study drug dosing [o] | Table 6 | → | | | | | | | | | | |
| Vineland-3 [p] | | X [g] | | | X [k] | | X | | | | X | |
| CGI-C | | X [g] | X | | X [k] | | X | | | | X | |
| ABC-C | | X [g] | X | | X [k] | | X | | | | X | |
| PedsQL | | X [g] | X | | X [k] | | X | | | | X | |
| CaGI-C | | X [g] | X | | X [k] | | X | | | | X | |
| Suicidality assessment [q] | | X [g] | X | | X [k] | | X | | | | X | |
| Submission of SIF to ESCI (if applicable) [r] | | → | | | | | | | | | | |
| Concomitant medications | | X [g] | → | | | | | | | | | |
| AEs | | X [g] | → | | | | | | | | | |

Abbreviations: ABC-C = Aberrant Behavior Checklist-Community; AE = adverse event; bid = twice daily (bis in die); BMI = body mass index; CaGI-C = Caregiver Global Impression of Change; CGI-C = Clinical Global Impression - Change scale; CGI S = Clinical Global Impression - Severity scale; C-SSRS = Columbia Suicide Severity Rating Scale; eDiary = electronic diary; ECG = electrocardiogram; eCRF = electronic case report form; EOS = End of Study; ESCI = Epilepsy Study Consortium; ET = Early Termination; PedsQL = Pediatric Quality of Life Inventory; SIF = seizure identification form; V-EEG = video electroencephalogram

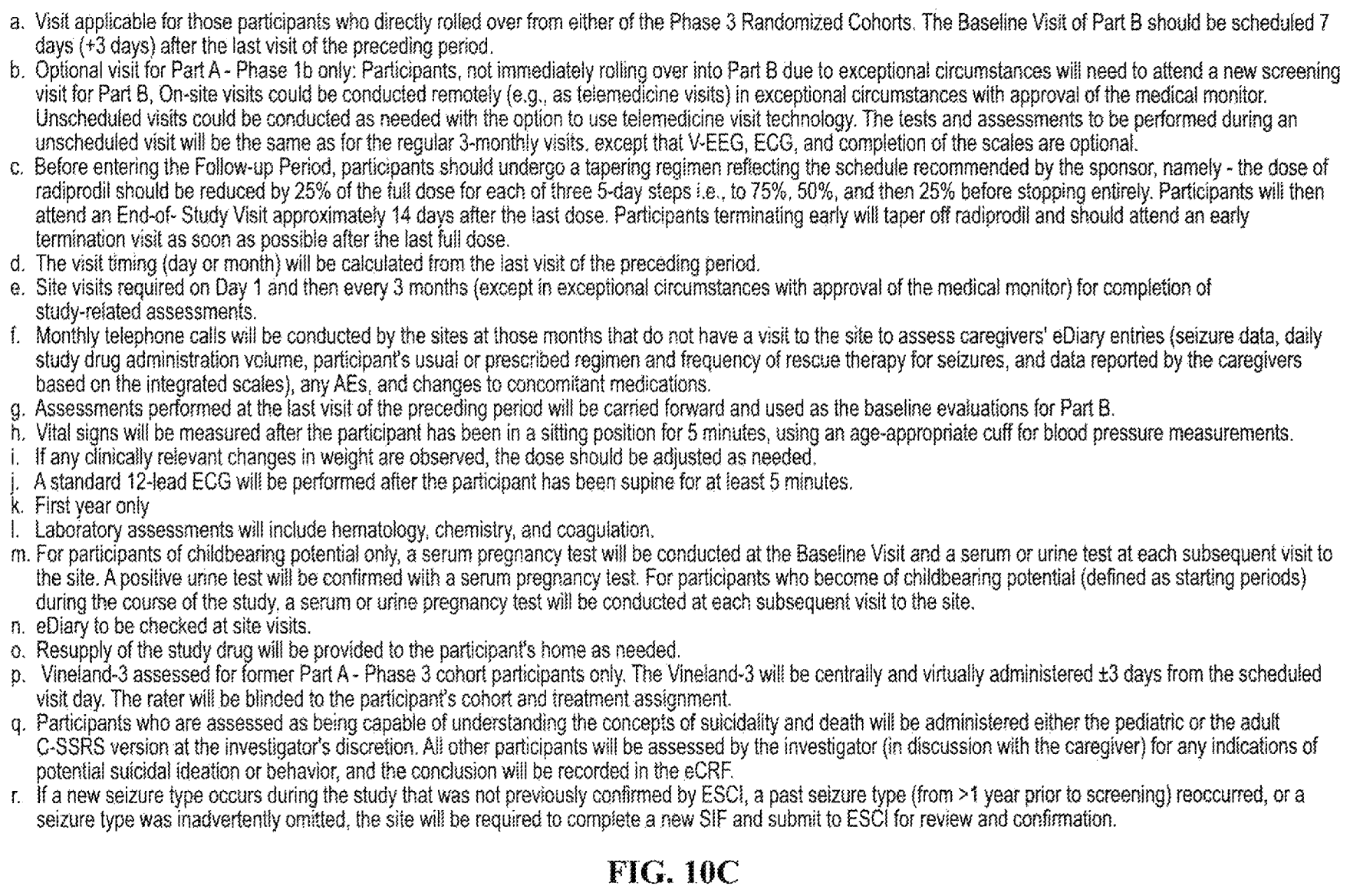

FIG. 10B a. Visit applicable for those participants who directly rolled over from either of the Phase 3 Randomized Cohorts. The Baseline Visit of Part B should be scheduled 7 days (+3 days) after the last visit of the preceding period.
b. Optional visit for Part A - Phase 1b only: Participants, not immediately rolling over into Part B due to exceptional circumstances will need to attend a new screening visit for Part B, On-site visits could be conducted remotely (e.g., as telemedicine visits) in exceptional circumstances with approval of the medical monitor. Unscheduled visits could be conducted as needed with the option to use telemedicine visit technology. The tests and assessments to be performed during an unscheduled visit will be the same as for the regular 3-monthly visits, except that V-EEG, ECG, and completion of the scales are optional.
c. Before entering the Follow-up Period, participants should undergo a tapering regimen reflecting the schedule recommended by the sponsor, namely - the dose of radiprodil should be reduced by 25% of the full dose for each of three 5-day steps i.e., to 75%, 50%, and then 25% before stopping entirely. Participants will then attend an End-of- Study Visit approximately 14 days after the last dose. Participants terminating early will taper off radiprodil and should attend an early termination visit as soon as possible after the last full dose.
d. The visit timing (day or month) will be calculated from the last visit of the preceding period.
e. Site visits required on Day 1 and then every 3 months (except in exceptional circumstances with approval of the medical monitor) for completion of study-related assessments.
f. Monthly telephone calls will be conducted by the sites at those months that do not have a visit to the site to assess caregivers' eDiary entries (seizure data, daily study drug administration volume, participant's usual or prescribed regimen and frequency of rescue therapy for seizures, and data reported by the caregivers based on the integrated scales), any AEs, and changes to concomitant medications.
g. Assessments performed at the last visit of the preceding period will be carried forward and used as the baseline evaluations for Part B.
h. Vital signs will be measured after the participant has been in a sitting position for 5 minutes, using an age-appropriate cuff for blood pressure measurements.
i. If any clinically relevant changes in weight are observed, the dose should be adjusted as needed.
j. A standard 12-lead ECG will be performed after the participant has been supine for at least 5 minutes.
k. First year only
l. Laboratory assessments will include hematology, chemistry, and coagulation.
m. For participants of childbearing potential only, a serum pregnancy test will be conducted at the Baseline Visit and a serum or urine test at each subsequent visit to the site. A positive urine test will be confirmed with a serum pregnancy test. For participants who become of childbearing potential (defined as starting periods) during the course of the study, a serum or urine pregnancy test will be conducted at each subsequent visit to the site.
n. eDiary to be checked at site visits.
o. Resupply of the study drug will be provided to the participant's home as needed.
p. Vineland-3 assessed for former Part A - Phase 3 cohort participants only. The Vineland-3 will be centrally and virtually administered ±3 days from the scheduled visit day. The rater will be blinded to the participant's cohort and treatment assignment.
q. Participants who are assessed as being capable of understanding the concepts of suicidality and death will be administered either the pediatric or the adult C-SSRS version at the investigator's discretion. All other participants will be assessed by the investigator (in discussion with the caregiver) for any indications of potential suicidal ideation or behavior, and the conclusion will be recorded in the eCRF.
r. If a new seizure type occurs during the study that was not previously confirmed by ESCI, a past seizure type (from >1 year prior to screening) reoccurred, or a seizure type was inadvertently omitted, the site will be required to complete a new SIF and submit to ESCI for review and confirmation.

FIG. 10C

| Visit/Week | Transition Titration Period [a,c] | | | | | Early Termination or ET[d] | Follow-up Period[d] 14 (+7) days post last dose |
|---|---|---|---|---|---|---|---|
| | TT1 [g] / Week 1 | TT2 [f] / Week 2 | TT3 [f] / Week 3 | TT4 [e,f] / Week 4 | TT5 / [b] Week 5 | | |
| Timeframe [days] | tt1[g] | (tt1+7) +3 | (tt2+7) +3 | (tt3+7) +3 | (tt4+7) +3 | | |
| Eligibility reconfirmation | X | | | | | | |
| Participant feedback interview / questionnaire | | | | | | X | X |
| Physical and neurological examination [h] | X | | | | | X | |
| Vital signs (blood pressure and pulse rate) [i] | → | → | → | → | → | → | → |
| Height and weight [j] | X | | X | | | X | |
| V-EEG | X | | | | | X | |
| Clinical laboratory tests [k] | → | → | → | → | → | → | → |
| Pregnancy test [l] | X | | | | | X | |
| Check eDiary / records; retrain if necessary | X | X | X | X | X | X | |
| Daily study drug administration [m] | → | → | → | → | → | | |
| Blood sampling for PK [n] | X | | | | | | |
| Vineland-3 [o] | X | | | | | X | |
| CGI-C | X | | | | | X | |
| ABC-C | X | | | | | X | |
| PedsQL | X | | | | | X | |
| CaGI-C | X | | | | | X | |
| Suicidality assessment [p] | X | | | | | X | |
| Submission of SIF to ESCI (if applicable)[q] | → | → | → | → | → | → | → |
| Concomitant medications | → | → | → | → | → | → | → |
| AEs | → | → | → | → | → | → | → |

Abbreviations: ABC-C = aberrant behavior checklist-community; AE = adverse event; bid = twice daily (bis in die); CaGI-C Caregiver Global Impression of Change; CGI-C = Clinical Global Impression of Change scale; CGI-S = Clinical Global Impression - Severity scale; C-SSRS = Columbia-Suicide Severity Rating Scale; ECG = electrocardiogram; eCRF = electronic case report form; eDiary = electronic diary; ET = early termination; m = Maintenance Period study day; M = Maintenance Period Visit; PedsQL = Pediatric Quality of Life Inventory; PK = pharmacokinetics; SIF = seizure identification form; tt = Transition Titration study day; TT = Transition Titration Visit; V-EEG = video electroencephalogram

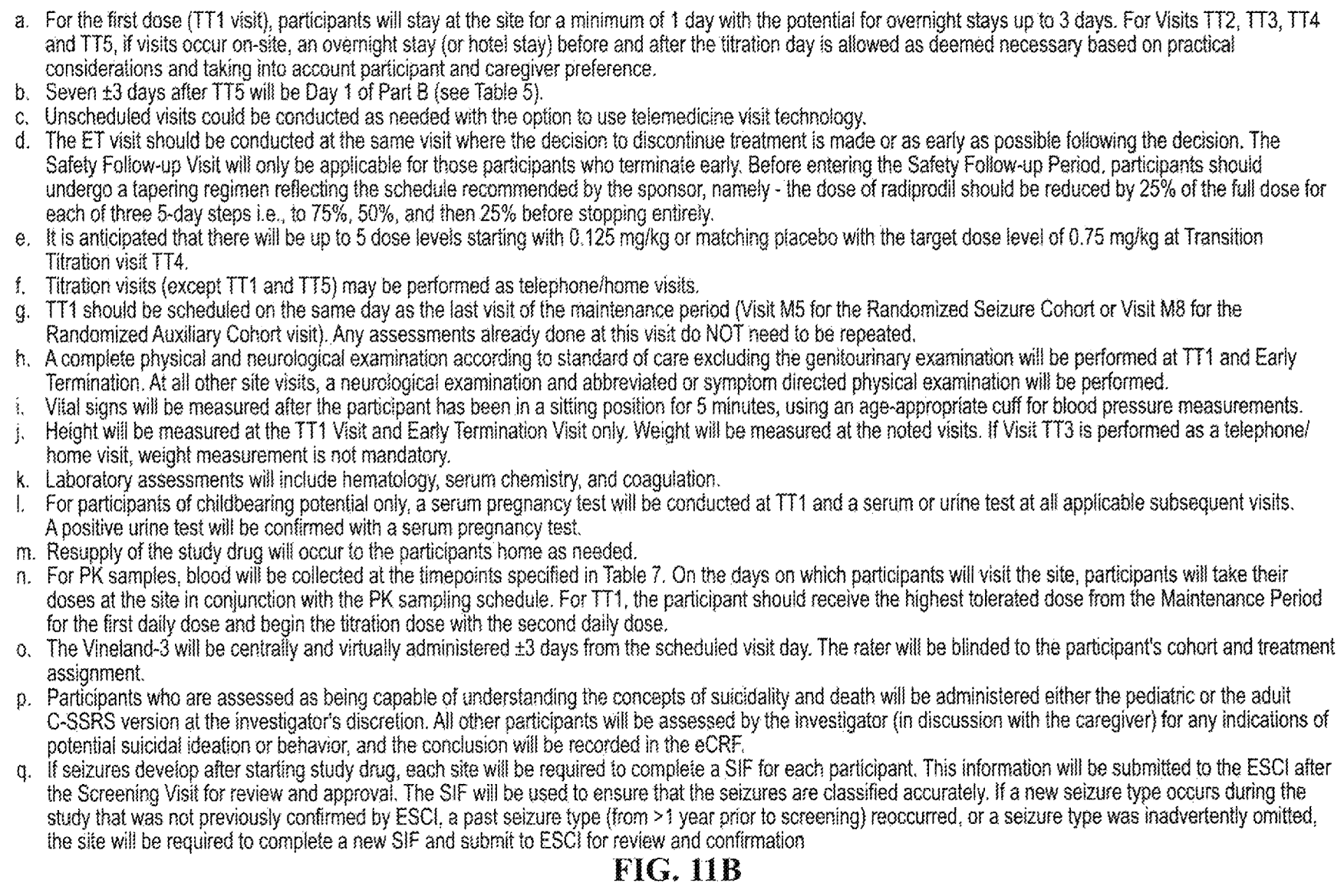

FIG. 11A a. For the first dose (TT1 visit), participants will stay at the site for a minimum of 1 day with the potential for overnight stays up to 3 days. For Visits TT2, TT3, TT4 and TT5, if visits occur on-site, an overnight stay (or hotel stay) before and after the titration day is allowed as deemed necessary based on practical considerations and taking into account participant and caregiver preference.
b. Seven ±3 days after TT5 will be Day 1 of Part B (see Table 5).
c. Unscheduled visits could be conducted as needed with the option to use telemedicine visit technology.
d. The ET visit should be conducted at the same visit where the decision to discontinue treatment is made or as early as possible following the decision. The Safety Follow-up Visit will only be applicable for those participants who terminate early. Before entering the Safety Follow-up Period, participants should undergo a tapering regimen reflecting the schedule recommended by the sponsor, namely - the dose of radiprodil should be reduced by 25% of the full dose for each of three 5-day steps i.e., to 75%, 50%, and then 25% before stopping entirely.
e. It is anticipated that there will be up to 5 dose levels starting with 0.125 mg/kg or matching placebo with the target dose level of 0.75 mg/kg at Transition Titration visit TT4.
f. Titration visits (except TT1 and TT5) may be performed as telephone/home visits.
g. TT1 should be scheduled on the same day as the last visit of the maintenance period (Visit M5 for the Randomized Seizure Cohort or Visit M8 for the Randomized Auxiliary Cohort visit). Any assessments already done at this visit do NOT need to be repeated.
h. A complete physical and neurological examination according to standard of care excluding the genitourinary examination will be performed at TT1 and Early Termination. At all other site visits, a neurological examination and abbreviated or symptom directed physical examination will be performed.
i. Vital signs will be measured after the participant has been in a sitting position for 5 minutes, using an age-appropriate cuff for blood pressure measurements.
j. Height will be measured at the TT1 Visit and Early Termination Visit only. Weight will be measured at the noted visits. If Visit TT3 is performed as a telephone/home visit, weight measurement is not mandatory.
k. Laboratory assessments will include hematology, serum chemistry, and coagulation.
l. For participants of childbearing potential only, a serum pregnancy test will be conducted at TT1 and a serum or urine test at all applicable subsequent visits. A positive urine test will be confirmed with a serum pregnancy test.
m. Resupply of the study drug will occur to the participants home as needed.
n. For PK samples, blood will be collected at the timepoints specified in Table 7. On the days on which participants will visit the site, participants will take their doses at the site in conjunction with the PK sampling schedule. For TT1, the participant should receive the highest tolerated dose from the Maintenance Period for the first daily dose and begin the titration dose with the second daily dose.
o. The Vineland-3 will be centrally and virtually administered ±3 days from the scheduled visit day. The rater will be blinded to the participant's cohort and treatment assignment.
p. Participants who are assessed as being capable of understanding the concepts of suicidality and death will be administered either the pediatric or the adult C-SSRS version at the investigator's discretion. All other participants will be assessed by the investigator (in discussion with the caregiver) for any indications of potential suicidal ideation or behavior, and the conclusion will be recorded in the eCRF.
q. If seizures develop after starting study drug, each site will be required to complete a SIF for each participant. This information will be submitted to the ESCI after the Screening Visit for review and approval. The SIF will be used to ensure that the seizures are classified accurately. If a new seizure type occurs during the study that was not previously confirmed by ESCI, a past seizure type (from >1 year prior to screening) reoccurred, or a seizure type was inadvertently omitted, the site will be required to complete a new SIF and submit to ESCI for review and confirmation

FIG. 11B

| Visit | Timepoint (Hours After First Dose) | Time Window (+ Minutes) |
|---|---|---|
| **Part A – Phase 1b** | | |
| T1 predose | Predose | NA |
| T1 after first dose | 1 | 15 |
| | 2 | 15 |
| | 4 | 60 |
| | 6 | 60 |
| | 8 | 60 |
| | 10 | 60 |
| T1 immediately before second dose | 12 | 60 |
| T2, T3, T4, and $T^N$ (first dose) | Predose | NA |
| | 1 | 15 |
| | 2 | 15 |
| | 5 | 60 |
| M1, M2, and M3 [a] | Predose | NA |
| M4 (first dose) | Predose | NA |
| | 1 | 15 |
| | 2 | 15 |
| | 5 | 60 |
| **Phase 3 Randomized Cohorts** | | |
| T1 | Predose | NA |
| | 2 | 15 |
| M1 | Predose | NA |
| | 1 | 15 |
| | 2 | 15 |
| M5 (first dose) | Predose | NA |
| | 1 | 15 |
| | 2 | 15 |
| | 4 | 60 |
| | 6 | 60 |
| | 8 | 60 |
| | 10 | 60 |
| | 12 (prior to $2^{nd}$ dose) | 60 |

Abbreviations: M = Maintenance Period Visit; NA = not applicable; T = Titration Period Visit a. Samples for analysis of metabolites are collected predose.

b. The Day 1 Visit will only be applicable for those participants who do not immediately roll over into Part B. For participants who immediately roll over into Part B, the PK evaluations performed at the last visit of the preceding period will be carried forward and used as baseline evaluations for Part B if the data were collected within 7 days prior to Day 1 of Part B.

FIG. 12

*Six patients completed CGI baseline and end of maintenance period assessments at the time these analyses were conducted.

METHODS OF USING RADIPRODIL IN THE TREATMENT OF DISORDERS

CROSS-REFERENCE

This application is a continuation of U.S. patent application Ser. No. 19/171,162, filed Apr. 4, 2025, which is a Continuation of International Application No. PCT/US2024/061589, filed Dec. 20, 2024, which claims priority to U.S. Provisional Application No. 63/612,997 filed Dec. 20, 2023, U.S. Provisional Application No. 63/612,998 filed Dec. 20, 2023, U.S. Provisional Application No. 63/691,887 filed Sep. 6, 2024, and U.S. Provisional Application No. 63/691,900 filed Sep. 6, 2024, the contents of each of which are incorporated herein by reference.

BACKGROUND

N-methyl-D-aspartate (NMDA) receptors are ligand-gated cation-channels embedded in the cell membranes of neurons. Overactivation of NMDA receptors by glutamate, their natural ligand, can lead to calcium overload of cells. This triggers a cascade of intracellular events that alters the cell function and ultimately may lead to death of neurons. Modulators of the NMDA receptors may be used for treating many disorders that are accompanied with excess release of glutamate, the main excitatory neurotransmitter in the central nervous system. For example, NR2B subtype selective antagonists of NMDA receptors are expected to possess little or no untoward side effects that are typically caused by the non-selective antagonists of NMDA receptors, namely psychotomimetic effects such as dizziness, headache, hallucinations, dysphoria and disturbances of cognitive and motor function. There is a need for NMDA receptor modulators that are useful for the treatment of disorders.

SUMMARY

The present disclosure provides, in an embodiment, methods of treating disorders in a subject comprising administering radiprodil, or pharmaceutically acceptable salt thereof, to the subject; compositions comprising radiprodil, and methods of use thereof.

In an embodiment, provided herein is a method of treating an epileptic disorder in a pediatric subject in need thereof, the method comprising orally administering to the pediatric subject of a compound of Formula I:

Formula I

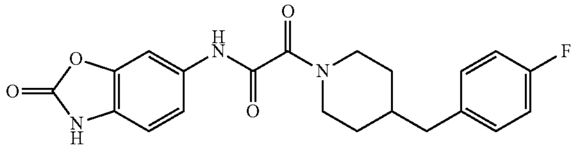

or a pharmaceutically acceptable salt thereof, wherein orally administering comprises: (i) a titration dose comprising:
- administering a first dose of the compound to the subject for a first time period;
- administering a second dose of the compound to the subject for a second time period;
- administering a third dose of the compound to the subject for a third time period; and

- administering a fourth dose of the compound to the subject for a fourth time period; and (ii) a maintenance dose comprising:
- administering a fifth dose of the compound to the subject.

In an embodiment, provided herein is a method of treating a seizure in a pediatric subject suffering from an epileptic disorder, the method comprising orally administering to the pediatric subject of a compound of Formula I:

Formula I

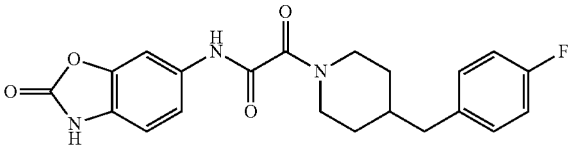 [SMILES: O=C(Nc1ccc2[nH]c(=O)oc2c1)C(=O)N1CCC(Cc2ccc(F)cc2)CC1]

or a pharmaceutically acceptable salt thereof, wherein orally administering comprises:

(i) a titration dose comprising:
- administering a first dose of the compound to the subject for a first time period;
- administering a second dose of the compound to the subject for a second time period;
- administering a third dose of the compound to the subject for a third time period; and
- administering a fourth dose of the compound to the subject for a fourth time period; and (ii) a maintenance dose comprising:
- administering a fifth dose of the compound to the subject.

In an embodiment, provided herein is a method of preventing a seizure in a pediatric subject suffering from an epileptic disorder, the method comprising orally administering to the pediatric subject of a compound of Formula I:

Formula I

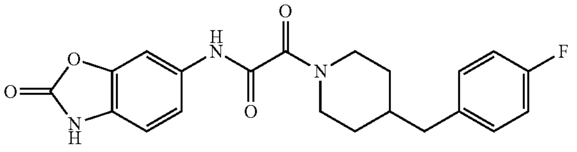

or a pharmaceutically acceptable salt thereof, wherein orally administering comprises:

(i) a titration dose comprising:
- administering a first dose of the compound to the subject for a first time period;
- administering a second dose of the compound to the subject for a second time period;
- administering a third dose of the compound to the subject for a third time period; and
- administering a fourth dose of the compound to the subject for a fourth time period; and (ii) a maintenance dose comprising:
- administering a fifth dose of the compound to the subject.

In an embodiment, provided herein is a method of reducing the risk of a seizure in a pediatric subject suffering from an epileptic disorder, the method comprising orally administering to the pediatric subject of a compound of Formula I:

Formula I

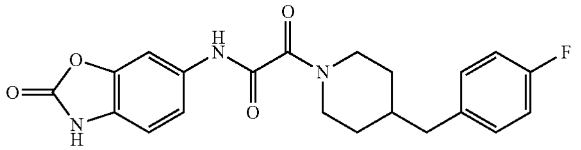

or a pharmaceutically acceptable salt thereof, wherein orally administering comprises: (i) a titration dose comprising:

- administering a first dose of the compound to the subject for a first time period;
  - administering a second dose of the compound to the subject for a second time period;
  - administering a third dose of the compound to the subject for a third time period; and
  - administering a fourth dose of the compound to the subject for a fourth time period; and
- (ii) a maintenance dose comprising:
  - administering a fifth dose of the compound to the subject.

In an embodiment, provided herein is a method of reducing seizure frequency in a pediatric subject suffering from an epileptic disorder, the method comprising orally administering to the pediatric subject of a compound of Formula I:

Formula I

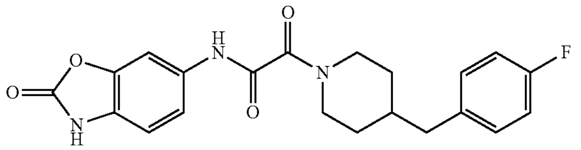

or a pharmaceutically acceptable salt thereof, wherein orally administering comprises:

- (i) a titration dose comprising:
  - administering a first dose of the compound to the subject for a first time period;
  - administering a second dose of the compound to the subject for a second time period;
  - administering a third dose of the compound to the subject for a third time period; and
  - administering a fourth dose of the compound to the subject for a fourth time period; and
- (ii) a maintenance dose comprising:
  - administering a fifth dose of the compound to the subject.

In an embodiment, provided herein is a method of reducing seizure severity in a pediatric subject suffering from an epileptic disorder, the method comprising orally administering to the pediatric subject of a compound of Formula I:

Formula I

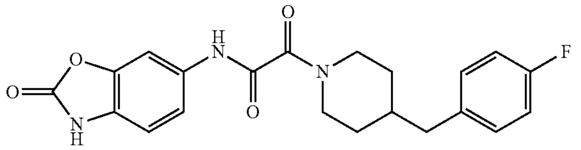

or a pharmaceutically acceptable salt thereof, wherein orally administering comprises: (i) a titration dose comprising:

- administering a first dose of the compound to the subject for a first time period;
- administering a second dose of the compound to the subject for a second time period;
- administering a third dose of the compound to the subject for a third time period; and
- administering a fourth dose of the compound to the subject for a fourth time period; and (ii) a maintenance dose comprising:

- administering a fifth dose of the compound to the subject.

In an embodiment, provided herein is a method of treating a neurobehavioral disorder in a subject in need thereof, the method comprising orally administering to the subject of a compound of Formula I:

Formula I

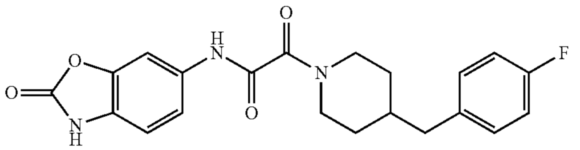

or a pharmaceutically acceptable salt thereof, wherein orally administering comprises:

- (i) a titration dose comprising:
  - administering a first dose of the compound to the subject for a first time period;
  - administering a second dose of the compound to the subject for a second time period;
  - administering a third dose of the compound to the subject for a third time period; and
  - administering a fourth dose of the compound to the subject for a fourth time period; and
- (ii) a maintenance dose comprising:
  - administering a fifth dose of the compound to the subject.

In some embodiments, the first dose is about 0.125 mg/kg of the compound twice a day. In some embodiment, the second dose is about 0.25 mg/kg of the compound twice a day. In some embodiment, the third dose is about 0.5 mg/kg of the compound twice a day. In some embodiment, the fourth dose is about 0.75 mg/kg of the compound twice a day. In some embodiment, the fifth dose is about 0.75 mg/kg of the compound twice a day.

In some embodiment, the method comprises: (i) determining whether the fifth dose is safe for the subject; (ii) if the fifth dose is determined not to be safe for the subject, then the method comprises reducing the fifth dose to a sixth dose that is lower than the fifth dose to the subject; and (iii) the sixth dose is about 0.5 mg/kg of the compound twice a day.

In some embodiments, each of the first time period, second time period, third time period, and fourth time period is seven to ten days.

In some embodiments, the compound is orally administered within one to four hours of the subject eating food. In some embodiments, the compound is orally administered within one to four hours of the subject eating a high-fat meal. In some embodiments, the compound is orally administered within two hours of the subject eating food. In some embodiments, the compound is orally administered within two hours of the subject eating a high-fat meal.

In some embodiments, orally administering the compound achieves a $C_{max}$ greater than 50 ng/mL in the subject. In some embodiments, the compound achieves a $C_{max}$ between 50 to 1400 ng/mL in the subject. In some embodiments, the compound achieves a $C_{max}$ between 100 to 1400 ng/ml in the subject. In some embodiments, the compound achieves a $C_{max}$ between 100 to 1000 ng/mL in the subject. In some embodiments, the compound achieves a $C_{max}$ between 100 to 500 ng/ml in the subject. In some embodiments, the compound achieves a $C_{max}$ between 100 to 200 ng/ml in the subject.

In some embodiments, orally administering the compound achieves an $AUC_{inf}$ greater than 500 hr*ng/mL in the subject. In some embodiments, the compound achieves an $AUC_{inf}$ between 500 to 2000 hr*ng/ml in the subject. In some embodiments, the compound achieves an $AUC_{inf}$ between 800 to 2000 hr*ng/mL in the subject. In some embodiments, the compound achieves an $AUC_{inf}$ between 1000 to 1500 hr*ng/mL in the subject. In some embodiments, the compound achieves an $AUC_{inf}$ between 1000 to 1200 hr*ng/ml in the subject.

In some embodiments, orally administering the compound comprises orally administering to the patient a pharmaceutical composition comprising about 30 weight percent of the compound, and a pharmaceutically acceptable excipient.

In some embodiments, the epileptic disorder is infantile spasm syndrome.

In some embodiments, the subject is less than 18 months old. In some embodiments, the subject is from 2 to 14 months old.

In some embodiments, the disorder is caused by or associated with a mutation in the subject, wherein the mutation is a GRIN2A gain-of-function mutation, a GRIN2B gain-of-function mutation, a GRIN1 gain-of-function mutation, or a GRIN2D gain-of-function mutation. In some embodiments, the disorder is caused by or associated with focal cortical dysplasia in the subject. In some embodiments, the method comprises identifying the focal cortical dysplasia with magnetic resonance imaging (MRI). In some embodiments, the epileptic disorder is caused by or associated with tuberous sclerosis complex in the subject.

In some embodiments, the subject suffers from a motor seizure. In some embodiments, the motor seizure is generalized onset seizure or focal seizure. In some embodiments, the generalized onset seizure is bilateral, tonic, clonic, atonic, myoclonic, or any combination thereof. In some embodiments, the focal seizure is bilateral hyperkinetic or clonic. In some embodiments, the motor seizure is a drop seizure that leads to trunk, or head and leads to a fall, injury, or slumping.

In some embodiments, the subject suffers from a drug-resistant seizure.

In some embodiments, the subject was administered at least one prior therapy to treat the epileptic disorder. In some embodiments, the subject was administered at least two prior therapies to treat the epileptic disorder. In some embodiments, each of the prior therapies to treat the epileptic disorder independently selected from surgery, vagus nerve stimulation, and anti-seizure medication.

In some embodiments, the anti-seizure medication is selected from brivaracetam (Briviact®), cannabidiol oral solution (Epidiolex®), carbamazepine (e.g., carbamazepine-XR), cenobamate, clobazam (Onfi® or Sympazan™ or Frisium), clonazepam, diazepam (e.g., diazepam nasal, diazepam rectal), divalproex sodium (Depakote®), valproic acid (Depakene®), oxcarbazepine (Trileptal® or Oxtellar XR), lamotrigine (Lamictal®), and phenytoin (Dilantin®).

In an embodiment, described herein is a pharmaceutically acceptable composition formulated for oral administration of a compound of Formula I:

Formula I

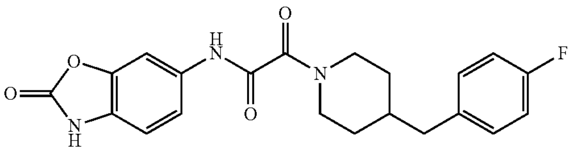

comprising: about 30% by weight of the compound of Formula I based on the total weight of the composition; at least one filler; a disintegrant; a binder; and a surfactant.

In some embodiments, compositions described herein comprise an anhydrous crystalline form of the compound of Formula I. In some embodiments, the anhydrous crystalline form has an X-ray powder diffraction pattern with characteristic peaks between and including the following values of 2θ in degrees: 7.8, 22.0, 23.7, 27.0 and 27.6±0.2° 2θ.

In some embodiments, the pharmaceutical composition comprises about 10% by weight to about 65% by weight of at least one filler based on the total weight of the pharmaceutical composition. In some embodiments, the at least one filler is selected from the group consisting of confectioner's sugar, compressible sugar, dextrates, dextrin, dextrose, lactose, mannitol, microcrystalline cellulose, powdered cellulose, sorbitol, sucrose, talc, and combinations thereof. In some embodiments, the composition comprises two fillers.

In some embodiments, the pharmaceutical composition comprises about 1% by weight to about 10% by weight of the disintegrant based on the total weight of the pharmaceutical composition. In some embodiments, the disintegrant is selected from the group consisting of crospovidone, croscarmellose sodium, sodium starch glycolate, microcrystalline cellulose, pregelatinized starch, and combinations thereof.

In some embodiments, the pharmaceutical composition comprises about 1% by weight to about 10% by weight of the binder based on the total weight of the pharmaceutical composition. In some embodiments, the binder is selected from the group consisting of povidone, starch, gelatin, sugars, natural and synthetic gums, alginates, polyethylene oxide, polyethylene glycol, inorganic calcium salts, silicic acid, polymethacrylates, waxes, water, alcohol, and combinations thereof.

In some embodiments, the pharmaceutical composition comprises about 0.01% by weight to about 5% by weight of the surfactant based on the total weight of the pharmaceutical composition. In some embodiments, the surfactant is selected from the group consisting of polyoxyethylene stearates, polyoxyethylene alkyl ethers, sorbitan fatty acid esters, poloxamers, polyoxyethylene castor oil derivatives, phospholipids, sodium phosphate, polysorbate (polyoxyethylene sorbitan fatty acid esters), and combinations thereof.

In some embodiments, the composition is a granule for an oral solution.

In an embodiment, provided herein is a solid pharmaceutically acceptable composition formulated for oral administration of a compound of Formula I:

Formula I

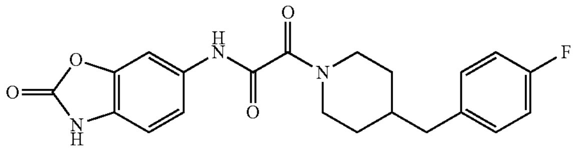

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In some embodiments, the composition comprises not more than about 0.1% to 0.5% of an impurity with respect to the quantity of the compound as measured by HPLC. In some embodiments, the composition comprises not more than about 0.1% to 0.5% of 6-amino-2-benzoxazolone with respect to the quantity of the compound as measured by HPLC.

In an embodiment, described herein is a pharmaceutically acceptable composition formulated for oral administration of a compound of Formula I:

Formula I

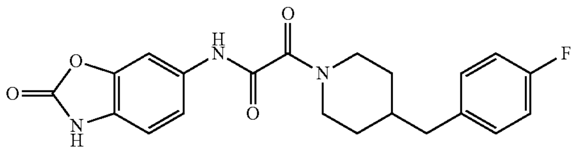

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients.

In some embodiments, compositions described herein comprises not more than about 0.5% of an impurity with respect to the quantity of the compound as measured by HPLC. In some embodiments, compositions described herein comprises not more than about 0.05% of an impurity with respect to the quantity of the compound as measured by HPLC.

In some embodiments, the composition comprises not more than about 0.5% of an impurity with respect to when exposed to 60% relative humidity at 25° C. for about 6 months. In some embodiments, the composition comprises not more than about 0.05% of an impurity with respect to when exposed to 60% relative humidity at 25° C. for about 6 months. In some embodiments, the composition comprises not more than about 0.5% of an impurity with respect to when exposed to 60% relative humidity at 25° C. for about 36 months. In some embodiments, the composition comprises not more than about 0.05% of an impurity with respect to when exposed to 60% relative humidity at 25° C. for about 36 months.

In some embodiments, the composition releases at least 80% of the compound after 10 minutes when the composition is tested in 2000 mL sodium phosphate solution in water using a USPII Paddle Apparatus at 37° C., with a paddle speed of 50 rpm.

In an embodiment, described herein is a pharmaceutically acceptable aqueous suspension for orally delivering about 0.1 mg/kg to 2 mg/kg of a compound of Formula I:

Formula I

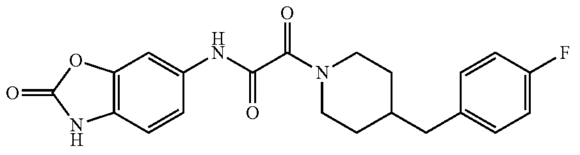

comprising: (i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension for orally delivering about 0.2 mg/kg to 2 mg/kg of a compound of Formula I:

Formula I

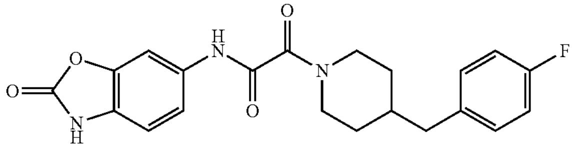

(i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension comprising a pharmaceutically acceptable composition described herein and an aqueous medium. In some embodiments, the aqueous medium comprises a starch-based suspension (e.g., SYRSPEND® SF).

In an embodiment, provided herein is a solid pharmaceutically acceptable composition formulated for oral administration of a compound of Formula I:

Formula I

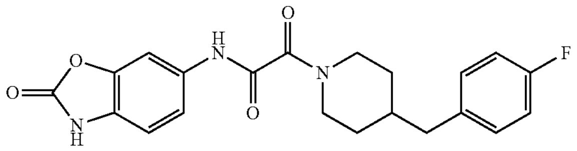

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In an embodiment, described herein is a pharmaceutically acceptable composition formulated for oral administration of a compound of Formula I:

Formula I

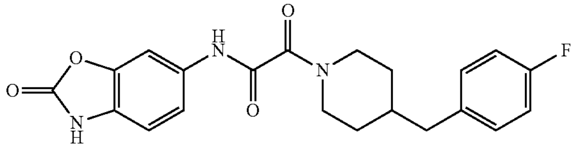

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients.

In an embodiment, described herein is a pharmaceutically acceptable aqueous suspension for orally delivering about 0.1 mg/kg to 2 mg/kg of a compound of Formula I:

Formula I

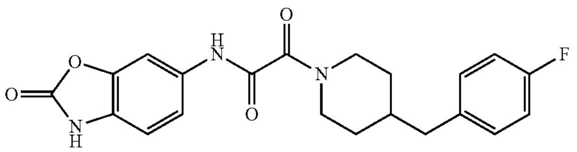

comprising: (i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension for orally delivering about 0.2 mg/kg to 2 mg/kg of a compound of Formula I:

Formula I

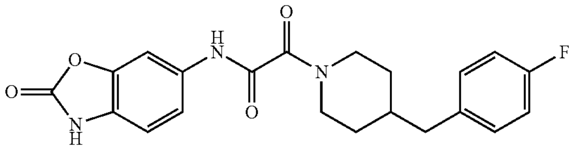

(i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension comprising a pharmaceutically acceptable composition described herein and an aqueous medium. In some embodiments, the aqueous medium comprises a starch-based suspension (e.g., SYRSPEND® SF).

In some embodiments, provided herein is a method of treating a convulsive disorder in a subject in need thereof, the method comprising administering to the subject any of the pharmaceutical compositions disclosed herein. In some embodiments, the convulsive disorder is epilepsy. In some embodiments, the subject is a pediatric subject. In some embodiments, the convulsive disorder is infantile spasm syndrome.

In an embodiment, described herein is a pharmaceutically acceptable composition formulated for oral administration of a compound of Formula I:

Formula I

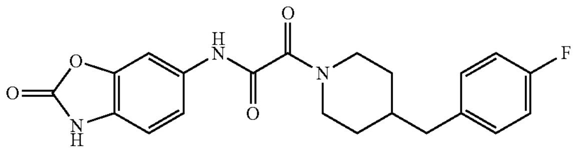

comprising: 30% by weight of the compound of Formula I based on the total weight of the composition; at least one filler; a disintegrant; a binder; and a surfactant.

In some embodiments, compositions described herein comprise an anhydrous crystalline form of the compound of Formula I. In some embodiments, the anhydrous crystalline form has an X-ray powder diffraction pattern with characteristic peaks between and including the following values of 2θ in degrees: 7.8, 22.0, 23.7, 27.0 and 27.6±0.2° 2θ.

In some embodiments, the pharmaceutical composition comprises about 10% by weight to about 65% by weight of at least one filler based on the total weight of the pharmaceutical composition. In some embodiments, the at least one filler is selected from the group consisting of confectioner's sugar, compressible sugar, dextrates, dextrin, dextrose, lactose, mannitol, microcrystalline cellulose, powdered cellulose, sorbitol, sucrose, talc, and combinations thereof. In some embodiments, the composition comprises two fillers.

In some embodiments, the pharmaceutical composition comprises about 1% by weight to about 10% by weight of the disintegrant based on the total weight of the pharmaceutical composition. In some embodiments, the disintegrant is selected from the group consisting of crospovidone, croscarmellose sodium, sodium starch glycolate, microcrystalline cellulose, pregelatinized starch, and combinations thereof.

In some embodiments, the pharmaceutical composition comprises about 1% by weight to about 10% by weight of the binder based on the total weight of the pharmaceutical composition. In some embodiments, the binder is selected from the group consisting of povidone, starch, gelatin, sugars, natural and synthetic gums, alginates, polyethylene oxide, polyethylene glycol, inorganic calcium salts, silicic acid, polymethacrylates, waxes, water, alcohol, and combinations thereof.

In some embodiments, the pharmaceutical composition comprises about 0.01% by weight to about 5% by weight of the surfactant based on the total weight of the pharmaceutical composition. In some embodiments, the surfactant is selected from the group consisting of polyoxyethylene stearates, polyoxyethylene alkyl ethers, sorbitan fatty acid esters, poloxamers, polyoxyethylene castor oil derivatives, phospholipids, sodium phosphate, polysorbate (polyoxyethylene sorbitan fatty acid esters), and combinations thereof.

In some embodiments, the composition is a granule for an oral solution.

In an embodiment, provided herein is a solid pharmaceutically acceptable composition formulated for oral administration of a compound of Formula I:

Formula I

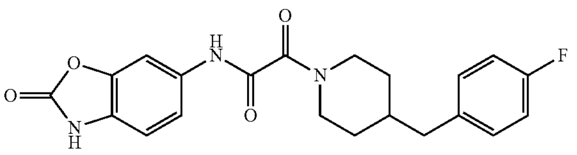

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In some embodiments, the composition comprises not more than about 0.1% to 0.5% of an impurity with respect to the quantity of the compound as measured by HPLC. In some embodiments, the composition comprises not more than about 0.1% to 0.5% of 6-amino-2-benzoxazolone with respect to the quantity of the compound as measured by HPLC.

In an embodiment, described herein is a pharmaceutically acceptable composition formulated for oral administration of a compound of Formula I:

Formula I

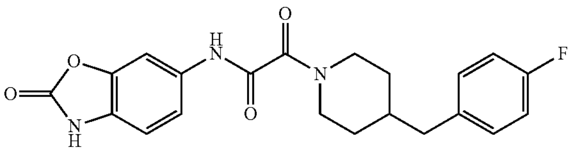

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients.

In some embodiments, compositions described herein comprises not more than about 0.5% of an impurity with respect to the quantity of the compound as measured by HPLC. In some embodiments, compositions described herein comprises not more than about 0.05% of an impurity with respect to the quantity of the compound as measured by HPLC.

In some embodiments, the composition comprises not more than about 0.5% of an impurity with respect to when exposed to 60% relative humidity at 25° C. for about 6 months. In some embodiments, the composition comprises not more than about 0.05% of an impurity with respect to when exposed to 60% relative humidity at 25° C. for about 6 months. In some embodiments, the composition comprises not more than about 0.5% of an impurity with respect to when exposed to 60% relative humidity at 25° C. for about 36 months. In some embodiments, the composition comprises not more than about 0.05% of an impurity with respect to when exposed to 60% relative humidity at 25° C. for about 36 months.

In some embodiments, the composition releases at least 80% of the compound after 10 minutes when the composition is tested in 2000 mL sodium phosphate solution in water using a USPII Paddle Apparatus at 37° C., with a paddle speed of 50 rpm.

In an embodiment, described herein is a pharmaceutically acceptable aqueous suspension for orally delivering about 0.1 mg/kg to 2 mg/kg of a compound of Formula I:

Formula I

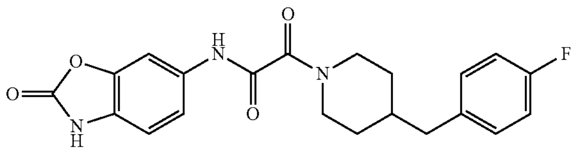

comprising: (i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension for orally delivering about 0.2 mg/kg to 2 mg/kg of a compound of Formula I:

Formula I

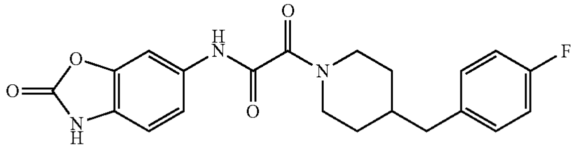

(i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension comprising a pharmaceutically acceptable composition described herein and an aqueous medium. In some embodiments, the aqueous medium comprises a starch-based suspension (e.g., SYRSPEND® SF).

In an embodiment, provided herein is a solid pharmaceutically acceptable composition formulated for oral administration of a compound of Formula I:

Formula I

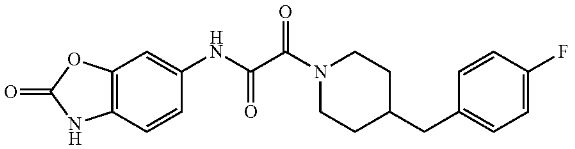

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In an embodiment, described herein is a pharmaceutically acceptable composition formulated for oral administration of a compound of Formula I:

Formula I

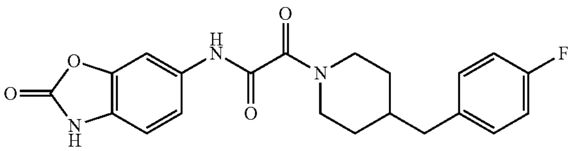

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients.

In an embodiment, described herein is a pharmaceutically acceptable aqueous suspension for orally delivering about 0.1 mg/kg to 2 mg/kg of a compound of Formula I:

Formula I

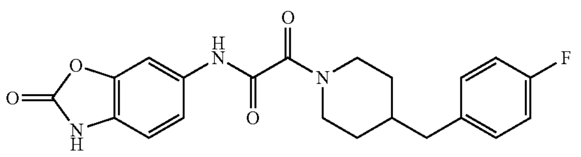

comprising: (i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension for orally delivering about 0.2 mg/kg to 2 mg/kg of a compound of Formula I:

Formula I

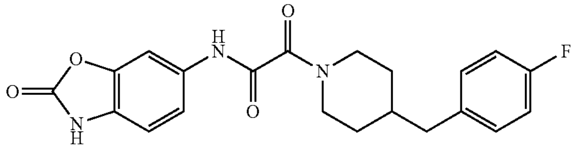

(i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In an embodiment, provided herein is a pharmaceutically acceptable aqueous suspension comprising a pharmaceutically acceptable composition described herein and an aqueous medium. In some embodiments, the aqueous medium comprises a starch-based suspension (e.g., SYRSPEND® SF).

In some embodiments, provided herein is a method of treating a convulsive disorder in a subject in need thereof, the method comprising administering to the subject any of the pharmaceutical compositions disclosed herein. In some embodiments, the convulsive disorder is epilepsy. In some embodiments, the subject is a pediatric subject. In some embodiments, the convulsive disorder is infantile spasm syndrome.

BRIEF DESCRIPTION OF THE DRAWINGS

FIG. 7A-D provides a schedule of events for the randomization qualifying seizure cohort study of Example 5.

FIG. 8A-D provides titration period assessments and timing of the randomized auxiliary cohort of participants without qualifying seizures study of Example 5.

FIG. 9A-B provides maintenance period schedules of the randomized auxiliary cohort of participants without qualifying seizures study of Example 5.

FIG. 10A-C provides an event schedule for the open label extension (OLE) study of Example 5.

FIG. 11A-B provides an event schedule for Part B of Example 5.

FIG. 12 provides a schedule for obtaining blood samples for pharmacokinetic (PK) analysis in the study of Example 5.

DETAILED DESCRIPTION

Figure 1:
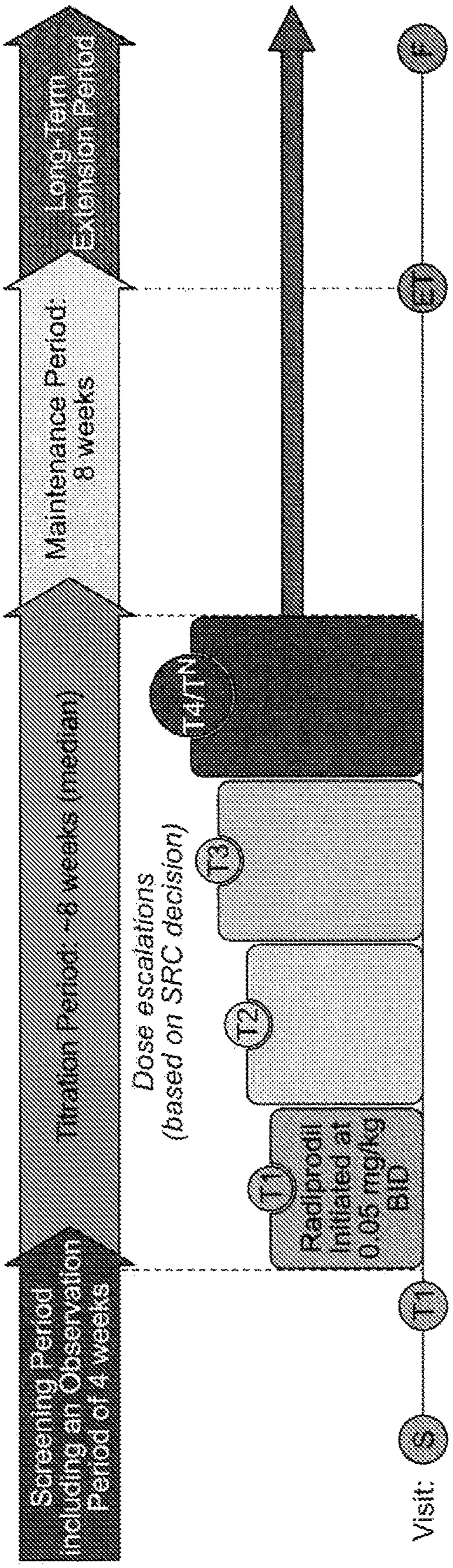
FIG. 1 illustrated the study design of a phase 1B study of radiprodil, as described in Example 4 below.

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

I. Compounds

In one embodiment, provided herein is a compound of the formula:

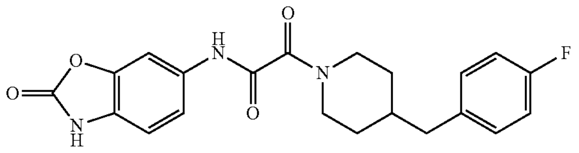

or a pharmaceutically acceptable salt thereof.

II. Pharmaceutical Compositions

In another embodiment, the present disclosure provides a pharmaceutical composition comprising a compound described herein, or pharmaceutically acceptable salt thereof, and a pharmaceutically acceptable excipient. In certain embodiments, the pharmaceutical composition comprises an effective amount of the compound. In certain embodiments, the pharmaceutical composition comprises a therapeutically effective amount of the compound.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Compositions for oral administration can take the form of bulk liquid solutions or suspensions, or bulk powders. In some embodiments, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component with the remainder being various vehicles or excipients and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component with the remainder being the injectable excipient and the like.

Transdermal compositions are typically formulated as a topical ointment or cream containing the active ingredient (s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope of the disclosure provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

In one embodiment, provided herein is a method comprising orally administering to a pediatric subject of a compound of Formula I:

Formula I

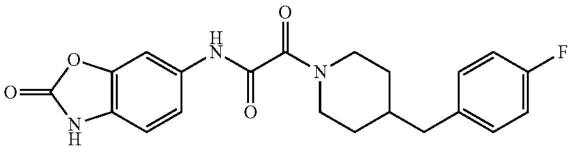

or a pharmaceutically acceptable salt thereof, wherein orally administering comprises:

(i) a titration dose comprising:
  - administering a first dose of the compound to the subject for a first time period;
  - administering a second dose of the compound to the subject for a second time period;
  - administering a third dose of the compound to the subject for a third time period; and
  - administering a fourth dose of the compound to the subject for a fourth time period; and (ii) a maintenance dose comprising:

administering a fifth dose of the compound to the subject.

In some embodiments, the method is for treating an epileptic disorder in a pediatric subject. In some embodiments, the method is for treating a seizure in a pediatric subject suffering from an epileptic disorder. In some embodiments, the method is for preventing a seizure in a pediatric subject suffering from an epileptic disorder. In some embodiments, the method is for reducing the risk of a seizure in a pediatric subject suffering from an epileptic disorder. In some embodiments, the method is for reducing seizure frequency in a pediatric subject suffering from an epileptic disorder. In some embodiments, the method is for reducing seizure severity in a pediatric subject suffering from an epileptic disorder. In some embodiments, the method is for treating a neurobehavioral disorder.

In some embodiment, the method further comprises: (i) the first dose is about 0.125 mg/kg of the compound twice a day; (ii) the second dose is about 0.25 mg/kg of the compound twice a day; (iii) the third dose is about 0.5 mg/kg of the compound twice a day; (iv) the fourth dose is about 0.75 mg/kg of the compound twice a day; and (v) the fifth dose is about 0.75 mg/kg of the compound twice a day.

In some embodiment, the method further comprises: (i) determining whether the fifth dose is safe for the subject; (ii) if the fifth dose is determined not to be safe for the subject, then the method comprises reducing the fifth dose to a sixth dose that is lower than the fifth dose to the subject; and (iii) the sixth dose is about 0.5 mg/kg of the compound twice a day.

In some embodiments, each of the first time period, second time period, third time period, and fourth time period is seven to ten days. In some embodiments, the compound is orally administered within one to four hours of the subject eating food. In some embodiments, the compound is orally administered within one to four hours of the subject eating a high-fat meal. In some embodiments, the compound is orally administered within two hours of the subject eating food. In some embodiments, the compound is orally administered within two hours of the subject eating a high-fat meal.

In some embodiments, orally administering the compound achieves a $C_{max}$ greater than 50 ng/mL in the subject. In some embodiments, the compound achieves a $C_{max}$ between 50 to 1400 ng/mL in the subject. In some embodiments, the compound achieves a $C_{max}$ between 100 to 1400 ng/mL in the subject. In some embodiments, the compound achieves a $C_{max}$ between 100 to 1000 ng/mL in the subject. In some embodiments, the compound achieves a $C_{max}$ between 100 to 500 ng/ml in the subject. In some embodiments, the compound achieves a $C_{max}$ between 100 to 200 ng/ml in the subject.

In some embodiments, orally administering the compound achieves an $AUC_{inf}$ greater than 100 hr*ng/ml (e.g., greater than 100 hr*ng/ml, greater than 150 hr*ng/mL, greater than 200 hr*ng/mL, greater than 250 hr*ng/mL, greater than 300 hr*ng/mL, greater than 100 hr*ng/ml, greater than 350 hr*ng/mL, greater than 400 hr*ng/mL, greater than 450 hr*ng/ml, greater than 500 hr*ng/mL, or greater than 550 hr*ng/ml) in the subject.

In some embodiments, orally administering the compound achieves an $AUC_{inf}$ greater than 500 hr*ng/ml in the subject. In some embodiments, the compound achieves an $AUC_{inf}$ between 500 to 2000 hr*ng/ml in the subject. In some embodiments, the compound achieves an $AUC_{inf}$ between 800 to 2000 hr*ng/ml in the subject. In some embodiments, the compound achieves an $AUC_{inf}$ between 1000 to 1500 hr*ng/ml in the subject. In some embodiments, the compound achieves an $AUC_{inf}$ between 1000 to 1200 hr*ng/ml in the subject.

In some embodiments, orally administering the compound comprises orally administering to the patient a pharmaceutical composition comprising about 30 weight percent of the compound, and a pharmaceutically acceptable excipient.

In some embodiments, the epileptic disorder is infantile spasm syndrome.

In some embodiments, the subject is less than 18 months old. In some embodiments, the subject is from 2 to 14 months old.

In some embodiments, the disorder is caused by or associated with a mutation in the subject, wherein the mutation is a GRIN2A gain-of-function mutation, a GRIN2B gain-of-function mutation, a GRIN1 gain-of-function mutation, or a GRIN2D gain-of-function mutation. In some embodiments, the disorder is caused by or associated with focal cortical dysplasia in the subject, comprising identifying the focal cortical dysplasia with magnetic resonance imaging (MRI). In some embodiments, the epileptic disorder is caused by or associated with tuberous sclerosis complex in the subject.

In some embodiments, the subject suffers from a motor seizure. In some embodiments, the motor seizure is generalized onset seizure or focal seizure. In some embodiments, the generalized onset seizure is bilateral, tonic, clonic, atonic, myoclonic, or any combination thereof. In some embodiments, the focal seizure is bilateral hyperkinetic or clonic. In some embodiments, the motor seizure is a drop seizure that leads to trunk, or head and leads to a fall, injury, or slumping.

In some embodiments, the subject suffers from a drug-resistant seizure.

In some embodiments, the subject was administered at least one prior therapy to treat the epileptic disorder. In some embodiments, the subject was administered at least two prior therapies to treat the epileptic disorder. In some embodiments, each of the prior therapies to treat the epileptic disorder independently selected from surgery, vagus nerve stimulation, and anti-seizure medication.

In some embodiments, the anti-seizure medication is selected from brivaracetam (Briviact®), cannabidiol oral solution (Epidiolex®), carbamazepine (e.g., carbamazepine-XR), cenobamate, clobazam (Onfi® or Sympazan™ or Frisium), clonazepam, diazepam (e.g., diazepam nasal, diazepam rectal), divalproex sodium (Depakote®), valproic acid (Depakene®), oxcarbazepine (Trileptal® or Oxtellar XR), lamotrigine (Lamictal®), and phenytoin (Dilantin®).

The pharmaceutically acceptable compositions described herein may comprise one or more impurities, such as those described herein. Exemplary impurities include compounds listed in Table 15 as provided herein.

In one embodiment, described herein is a pharmaceutically acceptable composition formulated for oral administration of a compound of Formula I:

Formula I

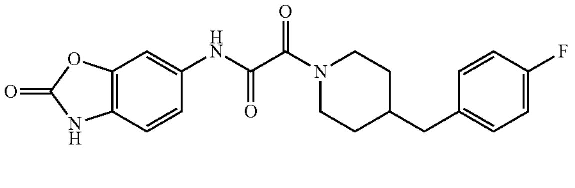

comprising: about 30% by weight of the compound of Formula I based on the total weight of the composition; at least one filler; a disintegrant; a binder; and a surfactant.

In some embodiments, the composition comprises an anhydrous crystalline form of the compound of Formula I. In some embodiments, the anhydrous crystalline form has an X-ray powder diffraction pattern with characteristic peaks between and including the following values of 2θ in degrees: 7.8, 22.0, 23.7, 27.0 and 27.6±0.2° 2θ. In some embodiments, the pharmaceutical composition comprises about 10% by weight to about 65% by weight of at least one filler based on the total weight of the pharmaceutical composition. In some embodiments, the at least one filler is selected from the group consisting of confectioner's sugar, compressible sugar, dextrates, dextrin, dextrose, lactose, mannitol, microcrystalline cellulose, powdered cellulose, sorbitol, sucrose, talc, and combinations thereof. In some embodiments, the composition comprises two fillers. In some embodiments, the pharmaceutical composition comprises about 1% by weight to about 10% by weight of the disintegrant based on the total weight of the pharmaceutical composition. In some embodiments, the disintegrant is selected from the group consisting of crospovidone, croscarmellose sodium, sodium starch glycolate, microcrystalline cellulose, pregelatinized starch, and combinations thereof. In some embodiments, the pharmaceutical composition comprises about 1% by weight to about 10% by weight of the binder based on the total weight of the pharmaceutical composition.

In one embodiment, the binder is selected from the group consisting of povidone, starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and combinations thereof. In some embodiments, the pharmaceutical composition comprises about 0.01% by weight to about 5% by weight of the surfactant based on the total weight of the pharmaceutical composition. In some embodiments, the surfactant is selected from the group consisting of polyoxyethylene stearates, polyoxyethylene alkyl ethers, sorbitan fatty acid esters, poloxamers, polyoxyethylene castor oil derivatives, phospholipids, sodium phosphate, polysorbate (polyoxyethylene sorbitan fatty acid esters), and combinations thereof. In some embodiments, the composition is a granule for an oral solution.

In one embodiment, provided herein is a solid pharmaceutically acceptable composition formulated for oral administration of a compound of Formula I:

Formula I

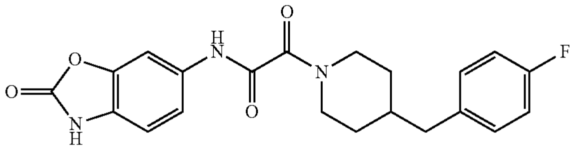

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In one embodiment, the composition comprises not more than about 0.1% to 0.5% (e.g., not more than 0.05%) of an impurity with respect to the quantity of the compound as measured by HPLC. In some embodiments, the composition comprises not more than about 0.1% to 0.5% of 6-amino-2-benzoxazolone with respect to the quantity of the compound as measured by HPLC.

In one embodiment, described herein is a pharmaceutically acceptable composition formulated for oral administration of a compound of Formula I:

Formula I

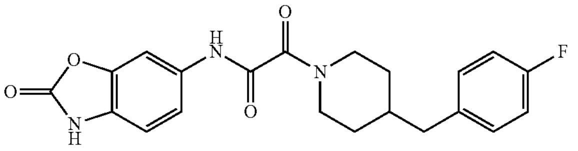

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients.

In one embodiment, provided herein is a solid pharmaceutically acceptable composition formulated for oral administration of a compound of Formula I:

Formula I

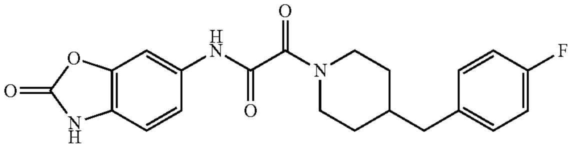

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In one embodiment, described herein is a pharmaceutically acceptable composition formulated for oral administration of a compound of Formula I:

Formula I

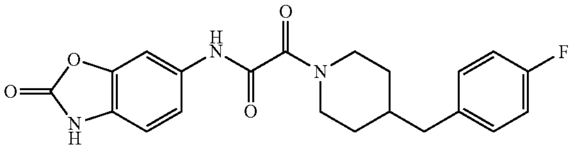

comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients. In some embodiments, the composition comprises not more than about 0.5% of an impurity (e.g., 6-amino-2-benzoxazolone) with respect to the quantity of the compound as measured by HPLC. In some embodiments, the composition comprises not more than about 0.05% of an impurity (e.g., 6-amino-2-benzoxazolone) with respect to the quantity of the compound as measured by HPLC. In some embodiments, the composition comprises not more than about 0.5% of an impurity (e.g., 6-amino-2-benzoxazolone) with respect to when exposed to 60% relative humidity at 25° C. for about 6 months. In some embodiments, the composition comprises not more than about 0.05% of an impurity (e.g., 6-amino-2-benzoxazolone) with respect to when exposed to 60% relative humidity at 25° C. for about 6 months. In some embodiments, the composition comprises not more than about 0.5% of an impurity (e.g., 6-amino-2-benzoxazolone) with respect to when exposed to 60% relative humidity at 25° C. for about 36 months. In some embodiments, the composition comprises not more than about 0.05% of an impurity (e.g., 6-amino-2-benzoxazolone) with respect to when exposed to 60% relative humidity at 25° C. for about 36 months. In some embodiments, the composition releases at least 80% of the compound after 10 minutes when the composition is tested in 2000 mL sodium phosphate solution in water using a USPII Paddle Apparatus at 37° C., with a paddle speed of 50 rpm. In one embodiment, provided herein is a pharmaceutically acceptable aqueous suspension comprising a pharmaceutically acceptable composition described herein and an aqueous medium. In some embodiments, the aqueous medium comprising a starch-based suspension (e.g., SYRSPEND® SF).

In one embodiment, described herein is a pharmaceutically acceptable aqueous suspension for orally delivering about 0.1 mg/kg to 2 mg/kg of a compound of Formula I:

Formula I

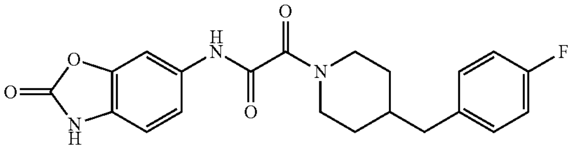

comprising: (i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In one embodiment, provided herein is a pharmaceutically acceptable aqueous suspension for orally delivering about 0.2 mg/kg to 2 mg/kg of a compound of Formula I:

Formula I

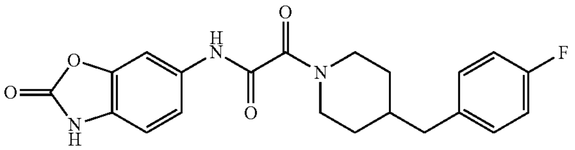

(i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium. In some embodiments, the aqueous medium comprises a starch-based suspension (e.g., SYRSPEND® SF).

In one embodiment, described herein is a pharmaceutically acceptable aqueous suspension for orally delivering about 0.1 mg/kg to 2 mg/kg of a compound of Formula I:

Formula I

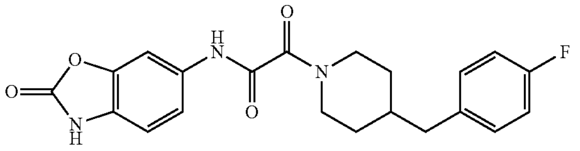

comprising: (i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In one embodiment, provided herein is a pharmaceutically acceptable aqueous suspension for orally delivering about 0.2 mg/kg to 2 mg/kg of a compound of Formula I:

Formula I

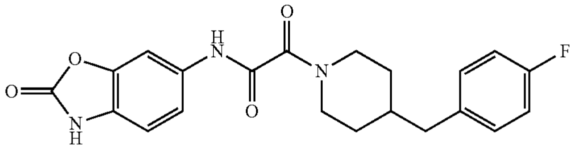

(i) a solid pharmaceutically acceptable composition comprising: about 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium. In some embodiments, the aqueous medium comprises a starch-based suspension (e.g., SYRSPEND® SF).

In one embodiment, described herein is a pharmaceutically acceptable composition formulated for oral administration of a compound of Formula I:

Formula I

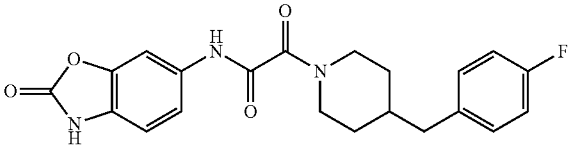

comprising: 30% by weight of the compound of Formula I based on the total weight of the composition; at least one filler; a disintegrant; a binder; and a surfactant.

In some embodiments, the composition comprises an anhydrous crystalline form of the compound of Formula I. In some embodiments, the anhydrous crystalline form has an X-ray powder diffraction pattern with characteristic peaks between and including the following values of 2θ in degrees: 7.8, 22.0, 23.7, 27.0 and 27.6±0.2° 2θ. In some embodiments, the pharmaceutical composition comprises about 10% by weight to about 65% by weight of at least one filler based on the total weight of the pharmaceutical composition. In some embodiments, the at least one filler is selected from the group consisting of confectioner's sugar, compressible sugar, dextrates, dextrin, dextrose, lactose, mannitol, microcrystalline cellulose, powdered cellulose, sorbitol, sucrose, talc, and combinations thereof. In some embodiments, the composition comprises two fillers. In some embodiments, the pharmaceutical composition comprises about 1% by weight to about 10% by weight of the disintegrant based on the total weight of the pharmaceutical composition. In some embodiments, the disintegrant is selected from the group consisting of crospovidone, croscarmellose sodium, sodium starch glycolate, microcrystalline cellulose, pregelatinized starch, and combinations thereof. In some embodiments, the pharmaceutical composition comprises about 1% by weight to about 10% by weight of the binder based on the total weight of the pharmaceutical composition.

In some embodiments, the binder is selected from the group consisting of povidone, starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and combinations thereof. In some embodiments, the pharmaceutical composition comprises about 0.01% by weight to about 5% by weight of the surfactant based on the total weight of the pharmaceutical composition. In some embodiments, the surfactant is selected from the group consisting of polyoxyethylene stearates, polyoxyethylene alkyl ethers, sorbitan fatty acid esters, poloxamers, polyoxyethylene castor oil derivatives, phospholipids, sodium phosphate, polysorbate (polyoxyethylene sorbitan fatty acid esters), and combinations thereof. In some embodiments, the composition is a granule for an oral solution.

In one embodiment, provided herein is a solid pharmaceutically acceptable composition formulated for oral administration of a compound of Formula I:

Formula I

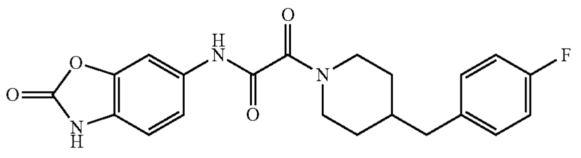

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In some embodiments, the composition comprises not more than about 0.1% to 0.5% (e.g., not more than 0.05%) of an impurity with respect to the quantity of the compound as measured by HPLC. In some embodiments, the composition comprises not more than about 0.1% to 0.5% of 6-amino-2-benzoxazolone with respect to the quantity of the compound as measured by HPLC.

In one embodiment, described herein is a pharmaceutically acceptable composition formulated for oral administration of a compound of Formula I:

Formula I

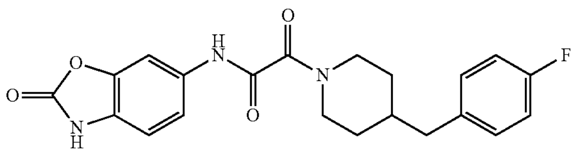

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients.

In one embodiment, provided herein is a solid pharmaceutically acceptable composition formulated for oral administration of a compound of Formula I:

Formula I

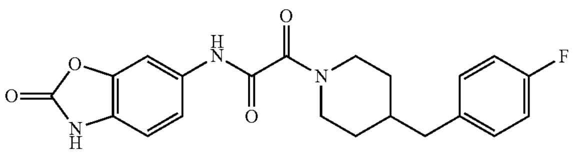

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition.

In one embodiment, described herein is a pharmaceutically acceptable composition formulated for oral administration of a compound of Formula I:

Formula I

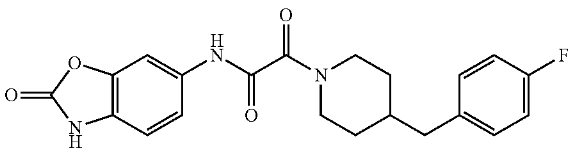

comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; not more than about 0.1% to 0.5% of an impurity (e.g., 6-amino-2-benzoxazolone) with respect to the quantity of the compound as measured by HPLC; and one or more pharmaceutically acceptable excipients. In some embodiments, the composition comprises not more than about 0.5% of an impurity (e.g., 6-amino-2-benzoxazolone) with respect to the quantity of the compound as measured by HPLC. In some embodiments, the composition comprises not more than about 0.05% of an impurity (e.g., 6-amino-2-benzoxazolone) with respect to the quantity of the compound as measured by HPLC. In some embodiments, the composition comprises not more than about 0.5% of an impurity (e.g., 6-amino-2-benzoxazolone) with respect to when exposed to 60% relative humidity at 25° C. for about 6 months. In some embodiments, the composition comprises not more than about 0.05% of an impurity (e.g., 6-amino-2-benzoxazolone) with respect to when exposed to 60% relative humidity at 25° C. for about 6 months. In some embodiments, the composition comprises not more than about 0.5% of an impurity (e.g., 6-amino-2-benzoxazolone) with respect to when exposed to 60% relative humidity at 25° C. for about 36 months. In some embodiments, the composition comprises not more than about 0.05% of an impurity (e.g., 6-amino-2-benzoxazolone) with respect to when exposed to 60% relative humidity at 25° C. for about 36 months. In some embodiments, the composition releases at least 80% of the compound after 10 minutes when the composition is tested in 2000 mL sodium phosphate solution in water using a USPII Paddle Apparatus at 37° C., with a paddle speed of 50 rpm. In one embodiment, provided herein is a pharmaceutically acceptable aqueous suspension comprising a pharmaceutically acceptable composition described herein and an aqueous medium. In some embodiments, the aqueous medium comprising a starch-based suspension (e.g., SYRSPEND® SF).

In one embodiment, described herein is a pharmaceutically acceptable aqueous suspension for orally delivering about 0.1 mg/kg to 2 mg/kg of a compound of Formula I:

Formula I

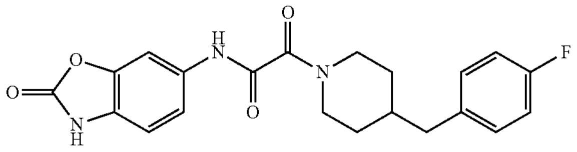

comprising: (i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In one embodiment, provided herein is a pharmaceutically acceptable aqueous suspension for orally delivering about 0.2 mg/kg to 2 mg/kg of a compound of Formula I:

Formula I

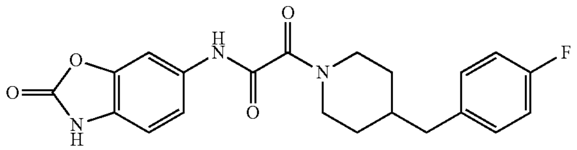

(i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 7.8, 22.0, 23.7, 27.0 and 27.6±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium. In some embodiments, the aqueous medium comprises a starch-based suspension (e.g., SYRSPEND® SF).

In one embodiment, described herein is a pharmaceutically acceptable aqueous suspension for orally delivering about 0.1 mg/kg to 2 mg/kg of a compound of Formula I:

Formula I

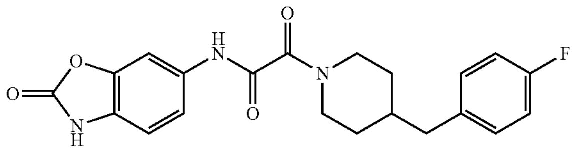

comprising: (i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium.

In one embodiment, provided herein is a pharmaceutically acceptable aqueous suspension for orally delivering about 0.2 mg/kg to 2 mg/kg of a compound of Formula I:

Formula I

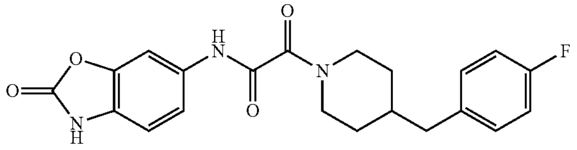

(i) a solid pharmaceutically acceptable composition comprising: 30% by weight of an anhydrous crystalline form of the compound of Formula I based on the total weight of the composition, wherein the anhydrous crystalline form has an X-ray powder diffraction pattern with characteristic peaks between and including the following values of 2θ in degrees: 6.4, 13.7, and 25.8±0.2° 2θ; about 50% to 60% by weight of a filler selected from the group consisting of mannitol, microcrystalline cellulose, and a combination thereof, based on the total weight of the composition; about 5% by weight of crospovidone based on the total weight of the composition; about 4% of povidone based on the total weight of the composition; and about 1% of a polysorbate based on the total weight of the composition; and (ii) an aqueous medium. In some embodiments, the aqueous medium comprises a starch-based suspension (e.g., SYRSPEND® SF).

III. Methods of Use

The present disclosure provides, in an embodiment, methods of treating disorders in a subject comprising administering radiprodil, or pharmaceutically acceptable salt thereof, to the subject; compositions comprising radiprodil, and methods of use thereof.

In some embodiments, the disorder is an epileptic disorder. In some embodiments, the disorder is infantile spasm syndrome. In some embodiments, the disorder is a brain disorder characterized by a trait or state overactive glutamatergic transmission that include genetic disorders characterized by mutations in the NMDA glutamate receptor subunits as GRIN2B, GRIN2A, GRIN1 and GRIN2D, or other epileptic disorders determined by malformation of cortical development (e.g. Focal Cortical Dysplasia and Tuberous Sclerosis Complex) characterized by overexpression of the NDMA receptor subunit NR2B. In some embodiments, the overexpression of the NDMA receptor subunit NR2B is mediated by mutations in genes regulating PI3K, Akt, or mTOR pathways.

In some embodiments, the subject is a pediatric subject. In some embodiments, the method comprises orally administering radiprodil, or a pharmaceutically acceptable salt thereof, to the subject.

In an embodiment, provided herein is a method of treating an epileptic disorder in a pediatric subject in need thereof, the method comprising orally administering to the pediatric subject of a compound of Formula I:

Formula I

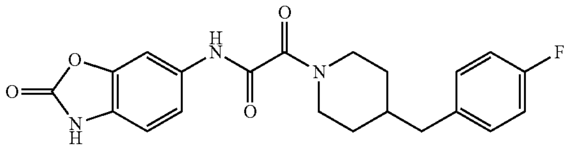

or a pharmaceutically acceptable salt thereof, wherein orally administering comprises:

(i) a titration dose comprising:
- administering a first dose of the compound to the subject for a first time period;
- administering a second dose of the compound to the subject for a second time period;
- administering a third dose of the compound to the subject for a third time period; and
- administering a fourth dose of the compound to the subject for a fourth time period; and (ii) a maintenance dose comprising:
- administering a fifth dose of the compound to the subject.

In an embodiment, provided herein is a method of treating a seizure in a pediatric subject suffering from an epileptic disorder, the method comprising orally administering to the pediatric subject of a compound of Formula I:

Formula I

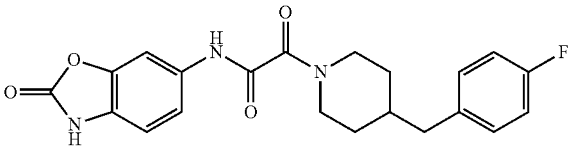

or a pharmaceutically acceptable salt thereof, wherein orally administering comprises:

(i) a titration dose comprising:
- administering a first dose of the compound to the subject for a first time period;
- administering a second dose of the compound to the subject for a second time period;
- administering a third dose of the compound to the subject for a third time period; and
- administering a fourth dose of the compound to the subject for a fourth time period; and (ii) a maintenance dose comprising:
- administering a fifth dose of the compound to the subject.

In an embodiment, provided herein is a method of preventing a seizure in a pediatric subject suffering from an epileptic disorder, the method comprising orally administering to the pediatric subject of a compound of Formula I:

Formula I

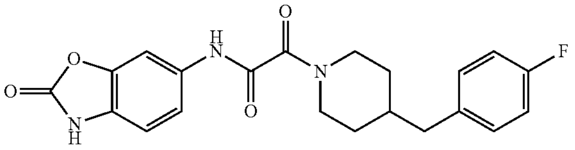

or a pharmaceutically acceptable salt thereof, wherein orally administering comprises:

(i) a titration dose comprising:
- administering a first dose of the compound to the subject for a first time period;
- administering a second dose of the compound to the subject for a second time period;
- administering a third dose of the compound to the subject for a third time period; and
- administering a fourth dose of the compound to the subject for a fourth time period; and (ii) a maintenance dose comprising:
- administering a fifth dose of the compound to the subject.

In an embodiment, provided herein is a method of reducing the risk of a seizure in a pediatric subject suffering from an epileptic disorder, the method comprising orally administering to the pediatric subject of a compound of Formula I:

Formula I

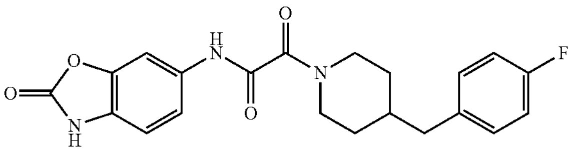

or a pharmaceutically acceptable salt thereof, wherein orally administering comprises:

(i) a titration dose comprising:

administering a first dose of the compound to the subject for a first time period;

administering a second dose of the compound to the subject for a second time period;

administering a third dose of the compound to the subject for a third time period; and administering a fourth dose of the compound to the subject for a fourth time period; and (ii) a maintenance dose comprising:

administering a fifth dose of the compound to the subject.

In an embodiment, provided herein is a method of reducing seizure frequency in a pediatric subject suffering from an epileptic disorder, the method comprising orally administering to the pediatric subject of a compound of Formula I:

Formula I

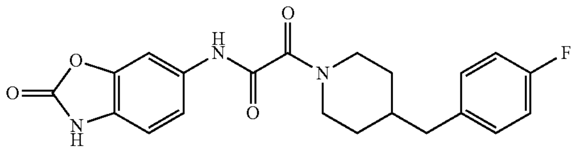

or a pharmaceutically acceptable salt thereof, wherein orally administering comprises:

(i) a titration dose comprising:

administering a first dose of the compound to the subject for a first time period;

administering a second dose of the compound to the subject for a second time period;

administering a third dose of the compound to the subject for a third time period; and administering a fourth dose of the compound to the subject for a fourth time period; and (ii) a maintenance dose comprising:

administering a fifth dose of the compound to the subject.

In an embodiment, provided herein is a method of reducing seizure severity in a pediatric subject suffering from an epileptic disorder, the method comprising orally administering to the pediatric subject of a compound of Formula I:

Formula I

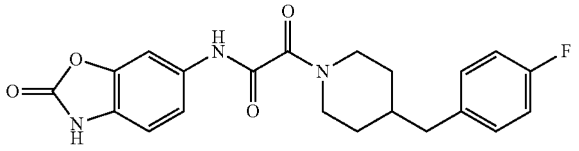

or a pharmaceutically acceptable salt thereof, wherein orally administering comprises:

(i) a titration dose comprising:

administering a first dose of the compound to the subject for a first time period;

administering a second dose of the compound to the subject for a second time period;

administering a third dose of the compound to the subject for a third time period; and administering a fourth dose of the compound to the subject for a fourth time period; and (ii) a maintenance dose comprising:

administering a fifth dose of the compound to the subject.

In some embodiments, the first dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the second dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the third dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the fourth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the fifth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the sixth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, each of the first dose, the second dose, the third dose, the fourth dose, the fifth dose, or the sixth dose is about 0.05 mg/kg to about 0.75 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, or about 0.75 mg/kg,) of the compound of Formula I, or a pharmaceutically acceptable salt thereof.

In an embodiment, the method further comprises: (i) determining whether the fifth dose is safe for the subject; (ii) if the fifth dose is determined not to be safe for the subject, then the method comprises reducing the fifth dose to a sixth dose that is lower than the fifth dose to the subject; and (iii) the sixth dose is about 0.5 mg/kg of the compound twice a day.

In some embodiments, the third dose does not exceed twice the amount of the first dose and the fourth dose does not exceed twice the amount of the second dose. In some embodiments, the third dose does not exceed 2.5 times the amount of the first dose and the fourth dose does not exceed 2.5 times the amount of the second dose.

In some embodiments, the fifth dose does not exceed twice the amount of the third dose and the sixth dose does not exceed twice the amount of the fourth dose.

In some embodiments, the first period of time is at least 7 days (e.g., 7 to 11 days). In some embodiments, the second period of time at least 7 days 7 days (e.g., 7 to 11 days). In some embodiments, the third period of time is at least 7 days (e.g., 7 to 11 days). In some embodiments, the fourth period of time is at least 7 days (e.g., 7 to 11 days).

In some embodiments, the first dose and the second dose are administered simultaneously. In some embodiments, the third dose and the fourth dose are administered simultaneously. In some embodiments, the fifth dose and the sixth dose are administered simultaneously.

In some embodiments, the compound is orally administered within one to four hours of the subject eating food; in some embodiments, the compound is orally administered within one to four hours of the subject eating a high-fat meal; in some embodiments, the compound is orally administered within two hours of the subject eating food; and in some embodiments, the compound is orally administered within two hours of the subject eating a high-fat meal.

In some embodiments, orally administering the compound achieves a $C_{max}$ greater than 50 ng/ml in the subject. In some embodiments, the compound achieves a $C_{max}$ between 50 to 1400 ng/mL in the subject. In some embodiments, the compound achieves a $C_{max}$ between 100 to 1400 ng/ml in the subject. In some embodiments, the compound achieves a $C_{max}$ between 100 to 1000 ng/mL in the subject. In some embodiments, the compound achieves a $C_{max}$ between 100 to 500 ng/mL in the subject. In some embodiments, the compound achieves a $C_{max}$ between 100 to 200 ng/ml in the subject.

In some embodiments, orally administering the compound achieves an $AUC_{inf}$ greater than 500 hr*ng/mL in the subject. In some embodiments, the compound achieves an $AUC_{inf}$ between 500 to 2000 hr*ng/mL in the subject. In some embodiments, the compound achieves an $AUC_{inf}$ between 800 to 2000 hr*ng/ml in the subject. In some embodiments, the compound achieves an $AUC_{inf}$ between 1000 to 1500 hr*ng/ml in the subject. In some embodiments, the compound achieves an $AUC_{inf}$ between 1000 to 1200 hr*ng/mL in the subject.

In some embodiments, orally administering the compound comprises orally administering to the patient a pharmaceutical composition comprising about 30 weight percent of the compound, and a pharmaceutically acceptable excipient.

In some embodiments, the epileptic disorder is infantile spasm syndrome.

In some embodiments, the pediatric subject is 2-12 years old. In some embodiments, the pediatric subject is from about 0-2 years old. In some embodiments, the pediatric subject is from 2-4 years old. In some embodiments, the pediatric subject is from 4 to 12 years old. In some embodiments, the pediatric subject is from 12-18 years old.

In some embodiments, the pediatric subject is up to 18 months old. In some embodiments, the pediatric subject is less than 18 months old. In some embodiments, the pediatric subject is from 2 to 14 months old.

In some embodiments, the epileptic disorder is caused by or associated with a mutation in the pediatric patient, wherein the mutation is a GRIN2A gain-of-function mutation, a GRIN2B gain-of-function mutation, a GRIN1 gain-of-function mutation, or a GRIN2D gain-of-function mutation. In some embodiments, the epileptic disorder is a GRIN-related epilepsy. In some embodiments, the epileptic disorder is a GRIN2B-related epilepsy. In some embodiments, the epileptic disorder is an early-onset epilepsy.

In some embodiments, the epileptic disorder is caused by or associated with focal cortical dysplasia (e.g., focal cortical dysplasia type I or focal cortical dysplasia type II) in the pediatric subject.

In some embodiments, the method comprises identifying the focal cortical dysplasia (e.g., focal cortical dysplasia type I or focal cortical dysplasia type II) with magnetic resonance imaging (MRI).

In some embodiments, the epileptic disorder is caused by or associated with tuberous sclerosis complex in the pediatric subject.

In some embodiments, the pediatric subject suffers from a motor seizure. In some embodiments, the motor seizure is generalized onset seizure or focal seizure.

In some embodiments, the generalized onset seizure is bilateral, tonic, clonic, atonic, myoclonic, or any combination thereof. In some embodiments, the generalized onset seizure is tonic, clonic, atonic, myoclonic. In some embodiments, the generalized onset seizure is tonic and clonic. In some embodiments, the generalized onset seizure is myoclonic and atonic. In some embodiments, the generalized onset seizure is tonic, clonic, and myoclonic.

In some embodiments, the generalized onset seizure is bilateral.

In some embodiments, the focal seizure is bilateral hyperkinetic or clonic.

In some embodiments, the motor seizure is a drop seizure that leads to trunk, or head and leads to a fall, injury, or slumping.

In some embodiments, the pediatric subject suffers from a drug-resistant seizure.

In some embodiments, the pediatric subject was administered at least one prior therapy to treat the epileptic disorder. In some embodiments, the pediatric subject was administered at least two prior therapies to treat the epileptic disorder.

In some embodiments, each of the therapies administered to treat the epileptic disorder is independently selected from surgery, vagus nerve stimulation, and anti-seizure medication.

In some embodiments, the anti-seizure medication is selected from brivaracetam (Briviact®), cannabidiol oral solution (Epidiolex®), carbamazepine (e.g., carbamazepine-XR), cenobamate, clobazam (Onfi® or Sympazan™ or Frisium), clonazepam, diazepam (e.g., diazepam nasal, diazepam rectal), divalproex sodium (Depakote®), valproic acid (Depakene®), oxcarbazepine (Trileptal® or Oxtellar XR), lamotrigine (Lamictal®), and phenytoin (Dilantin®).

In some embodiments, the method results in a reduction of seizure frequency of about 50%, about 55%, about 60%, about 65%, about 70%, about 75%, about 80%, about 85%, about 90%, about 95%, about 96%, about 97%, about 98%, or about 99% from baseline. In some embodiments, the method eliminates seizures.

The Clinical Global Impression Change (CGI-C) scale is a clinician measure of a change of a symptom or condition, using a single item, 7-point-scale. The CGI-C scale ranges from 1 ("Very much improved") to 7 ("Very much worse"). Clinicians rate change based on the totality of a clinical examination. In some embodiments, an improvement in a CGI-C score is a change toward 1 ("Very much improved"). In some embodiments, the method results in an improvement from baseline based on a Clinical Global Impression of Change (CGI-C).

The Caregiver Global Impression of Change (CaGI-C) scale is a 7-point caregiver rated scale ranging from 1 ("Very much improved") to 7 ("Very much worse"). In some embodiments, an improvement in a CaGI-C score is a change toward 1 ("Very much improved"). In some embodiments, the method results in an improvement from baseline based on a Caregiver Global Impression of Change (CaGI-C).

In some embodiments, the disorder is a neurobehavioral disorder. In some embodiments, the neurobehavioral disorder is caused by or associated with aberrant or abnormal expression (e.g., overexpression) of the NDMA receptor subunit NR2B. In some embodiments, the aberrant or abnormal expression (e.g., overexpression) of the NDMA receptor subunit NR2B is mediated by mutations in genes regulating PI3K, Akt, or mTOR pathways. In some embodiments, wherein the neurobehavioral disorder is caused by or associated with a mutation in the subject, wherein the mutation is a GRIN2A gain-of-function mutation, a GRIN2B gain-of-function mutation, a GRIN1 gain-of-function mutation, or a GRIN2D gain-of-function mutation. In some embodiments, the neurobehavioral disorder is a GRIN-related neurobehavioral disorder. In some embodiments, the neurobehavioral disorder is a GRIN2B-related neurobehavioral disorder.

In an embodiment, provided herein is a method of treating a neurobehavioral disorder in a subject in need thereof, the method comprising administering to the subject a therapeutically effective amount of a compound of Formula I:

Formula I

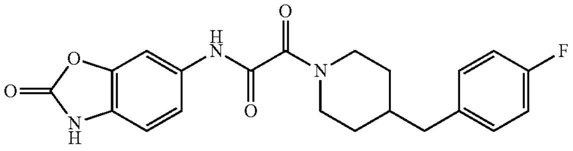

or a pharmaceutically acceptable salt thereof.

In some embodiments, the subject suffers from an encephalopathy. In some embodiments, the subject previously suffered from an encephalopathy. In some embodiments, the neurobehavioral disorder is a symptom caused by or associated with an encephalopathy.

In some embodiments, the encephalopathy is caused by or associated with brain injury (e.g., traumatic brain injury, e.g., chronic traumatic brain injury), infection (e.g., bacterial, viral, or prion), metabolic dysfunction, mitochondrial dysfunction, seizure (e.g., epileptic seizure), exposure to toxin (e.g., solvent, metal, or radiation), or trauma.

In some embodiments, the compound of Formula I, or a pharmaceutically acceptable salt thereof, is administered orally.

In an embodiment, the method further comprises: (i) determining whether the fifth dose is safe for the subject; (ii) if the fifth dose is determined not to be safe for the subject, then the method comprises reducing the fifth dose to a sixth dose that is lower than the fifth dose to the subject; and (iii) the sixth dose is about 0.5 mg/kg of the compound twice a day.

In some embodiments, the first dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the second dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the third dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the fourth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the fifth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the sixth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, each of the first dose, the second dose, the third dose, the fourth dose, the fifth dose, or the sixth dose is about 0.05 mg/kg to about 0.75 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, or about 0.75 mg/kg,) of the compound of Formula I, or a pharmaceutically acceptable salt thereof.

In some embodiments, the third dose does not exceed twice the amount of the first dose and the fourth dose does not exceed twice the amount of the second dose. In some embodiments, the third dose does not exceed 2.5 times the amount of the first dose and the fourth dose does not exceed 2.5 times the amount of the second dose.

In some embodiments, the fifth dose does not exceed twice the amount of the third dose and the sixth dose does not exceed twice the amount of the fourth dose.

In some embodiments, the first period of time is at least 7 days (e.g., 7 to 11 days). In some embodiments, the second period of time at least 7 days 7 days (e.g., 7 to 11 days). In some embodiments, the third period of time is at least 7 days (e.g., 7 to 11 days). In some embodiments, the fourth period of time is at least 7 days (e.g., 7 to 11 days).

In some embodiments, the first dose and the second dose are administered simultaneously. In some embodiments, the third dose and the fourth dose are administered simultaneously. In some embodiments, the fifth dose and the sixth dose are administered simultaneously.

In some embodiments, the subject is a pediatric subject.

In some embodiments, the pediatric subject is 2-12 years old. In some embodiments, the pediatric subject is from about 0-2 years old. In some embodiments, the pediatric subject is from 2-4 years old. In some embodiments, the pediatric subject is from 4 to 12 years old. In some embodiments, the pediatric subject is from 12-18 years old.

In some embodiments, the pediatric subject is up to 18 months old. In some embodiments, the pediatric subject is less than 18 months old. In some embodiments, the pediatric subject is from 2 to 14 months old.

In some embodiments, the neurobehavioral disorder is irritability, mood disorder, movement disorder, sleep disorder, or self-injurious behavior. In some embodiments, the neurobehavioral is self-injurious behavior, an inappropriate behavior, elopement, or a tantrum.

In some embodiments, the neurobehavioral disorder is caused by or associated with focal cortical dysplasia (e.g., focal cortical dysplasia type I or focal cortical dysplasia type II). In some embodiments, the neurobehavioral disorder is caused by or associated with tuberous sclerosis complex.

The Clinical Global Impression Change (CGI-C) scale is a clinician measure of a change of a symptom or condition, using a single item, 7-point-scale. The CGI-C scale ranges from 1 ("Very much improved") to 7 ("Very much worse"). Clinicians rate change based on the totality of a clinical examination. In some embodiments, an improvement in a CGI-C score is a change toward 1 ("Very much improved"). In some embodiments, the method results in an improvement from baseline based on a Clinical Global Impression of Change (CGI-C).

The Caregiver Global Impression of Change (CaGI-C) scale is a 7-point caregiver rated scale ranging from 1 ("Very much improved") to 7 ("Very much worse"). In some embodiments, an improvement in a CaGI-C score is a change toward 1 ("Very much improved"). In some embodiments, the method results in an improvement from baseline based on a Caregiver Global Impression of Change (CaGI-C).

In some embodiments, the subject is a pediatric subject. In some embodiments, the method comprises orally administering radiprodil, or a pharmaceutically acceptable salt thereof, to the subject.

In an embodiment, provided herein is a method of treating an epileptic disorder in a pediatric subject in need thereof, the method comprising orally administering to the pediatric subject a first dose and a second dose of a compound of Formula I:

Formula I

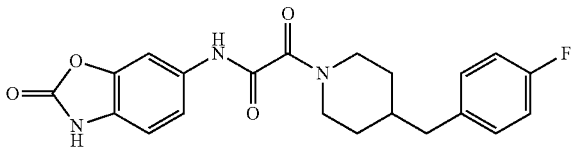

or a pharmaceutically acceptable salt thereof, wherein each of the first dose and the second dose is administered daily; wherein each of the first dose and the second does not exceed 2 mg/kg; and wherein the total amount of the compound of Formula I administered daily to the pediatric subject does not exceed 135 mg.

In an embodiment, provided herein is a method of treating a seizure in a pediatric subject suffering from an epileptic disorder, the method comprising orally administering to the pediatric subject a first dose and a second dose of a compound of Formula I:

Formula I

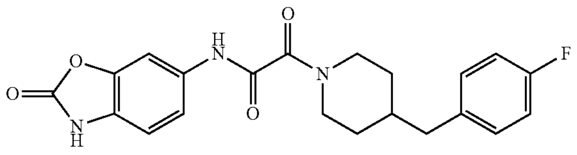

or a pharmaceutically acceptable salt thereof, wherein each of the first dose and the second dose is administered daily; wherein each of the first dose and the second does not exceed 2 mg/kg; and wherein the total amount of the compound of Formula I administered daily to the pediatric subject does not exceed 135 mg.

In an embodiment, provided herein is a method of preventing a seizure in a pediatric subject suffering from an epileptic disorder, the method comprising orally administering to the pediatric subject a first dose and a second dose of a compound of Formula I:

Formula I

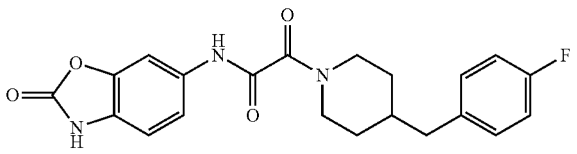

or a pharmaceutically acceptable salt thereof, wherein each of the first dose and the second dose is administered daily; wherein each of the first dose and the second does not exceed 2 mg/kg; and wherein the total amount of the compound of Formula I administered daily to the pediatric subject does not exceed 135 mg.

In an embodiment, provided herein is a method of reducing the risk of a seizure in a pediatric subject suffering from an epileptic disorder, the method comprising orally administering to the pediatric subject a first dose and a second dose of a compound of Formula I:

Formula I

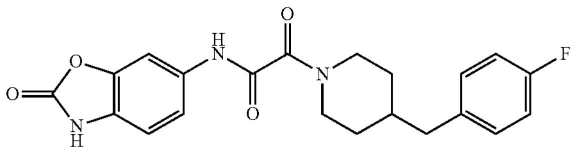

or a pharmaceutically acceptable salt thereof, wherein each of the first dose and the second dose is administered daily; wherein each of the first dose and the second does not exceed 2 mg/kg; and wherein the total amount of the compound of Formula I administered daily to the pediatric subject does not exceed 135 mg.

In an embodiment, provided herein is a method of reducing seizure frequency in a pediatric subject suffering from an epileptic disorder, the method comprising orally administering to the pediatric subject a first dose and a second dose of a compound of Formula I:

Formula I

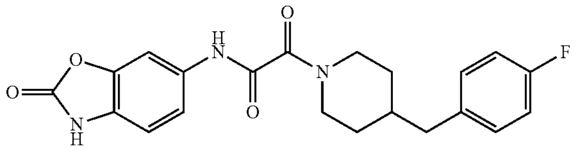

or a pharmaceutically acceptable salt thereof, wherein each of the first dose and the second dose is administered daily; wherein each of the first dose and the second does not exceed 2 mg/kg; and wherein the total amount of the compound of Formula I administered daily to the pediatric subject does not exceed 135 mg. In an embodiment, provided herein is a method of reducing seizure severity in a pediatric subject suffering from an epileptic disorder, the method comprising orally administering to the pediatric subject a first dose and a second dose of a compound of Formula I:

Formula I

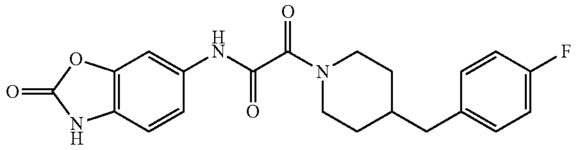

or a pharmaceutically acceptable salt thereof, wherein each of the first dose and the second dose is administered daily; wherein each of the first dose and the second does not exceed 2 mg/kg; and wherein the total amount of the compound of Formula I administered daily to the pediatric subject does not exceed 135 mg.

In some embodiments, the first dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the second dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the third dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the fourth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the fifth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the sixth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the seventh dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the eighth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the ninth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, the tenth dose is about 0.05 mg/kg to about 2 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1 mg/kg, about 1.05 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 1 mg/kg, or about 2 mg/kg) of a compound of Formula I, or a pharmaceutically acceptable salt thereof.

In some embodiments, each of the first dose, the second dose, the third dose, the fourth dose, the fifth dose, the sixth dose, the seventh dose, the eighth dose, the ninth dose, or the tenth dose is about 0.05 mg/kg to about 0.4 mg/kg (e.g., about 0.05 mg/kg, about 0.06 mg/kg, about 0.07 mg/kg, about 0.08 mg/kg, about 0.09 mg/kg, about 0.1 mg/kg, about 0.125 mg/kg, about 0.15 mg/kg, about 0.175 mg/kg, about 0.2 mg/kg, about 0.225 mg/kg, about 0.25 mg/kg, about 0.3 mg/kg, about 0.35 mg/kg, or about 0.4 mg/kg) of the compound of Formula I, or a pharmaceutically acceptable salt thereof.

In an embodiment, the method further comprises: (i) determining whether the first dose and the second dose are effective and safe for and tolerated by the pediatric subject after each of the first dose and the second dose is administered daily to the pediatric subject for a first period of time; and (ii) if each of the first dose and the second dose is determined to be safe for and tolerated by the pediatric subject, changing the first dose to a third dose of a compound of Formula I, or a pharmaceutically acceptable salt thereof, and changing the second dose to a fourth dose of a compound of Formula I, or a pharmaceutically acceptable salt thereof, and orally administering the third dose and the fourth dose to the pediatric subject, wherein each of the third dose and the fourth dose is administered daily; wherein each of the third dose and the fourth does not exceed 2 mg/kg; and wherein the total amount of the compound of Formula I administered daily to the pediatric subject does not exceed 135 mg.

In an embodiment, the method further comprises: (iii) determining whether the third dose and the fourth dose are effective and safe for and tolerated by the pediatric subject after each of the third dose and the fourth dose is administered daily to the pediatric subject for a second period of time; and (iv) if each of the third dose and the fourth dose is determined to be safe for and tolerated by the pediatric subject, changing the third dose to a fifth dose of a compound of Formula I, or a pharmaceutically acceptable salt thereof, and changing the fourth dose to a sixth dose of a compound of Formula I, or a pharmaceutically acceptable salt thereof, and orally administering the fifth dose and the sixth dose to the pediatric subject, wherein each of the fifth dose and the sixth dose is administered daily; wherein each of the fifth dose and the sixth dose does not exceed 2 mg/kg; and wherein the total amount of the compound of Formula I administered daily to the pediatric subject does not exceed 135 mg.

In an embodiment, the method further comprises: (v) determining whether the fifth dose and the sixth dose are effective and safe for and tolerated by the pediatric subject after each of the third dose and the fourth dose is administered daily to the pediatric subject for a third period of time; and (vi) if each of the fifth dose and the sixth dose is determined to be safe for and tolerated by the pediatric subject, changing the fifth dose to a seventh dose of a compound of Formula I, or a pharmaceutically acceptable salt thereof, and changing the sixth dose to an eighth dose of a compound of Formula I, or a pharmaceutically acceptable salt thereof, and orally administering the seventh dose and the eighth dose to the pediatric subject, wherein each of the seventh dose and the eighth dose is administered daily; wherein each of the seventh dose and the eighth dose does not exceed 2 mg/kg; and wherein the total amount of the compound of Formula I administered daily to the pediatric subject does not exceed 135 mg.

In an embodiment, the method further comprises: (vii) determining whether the seventh dose and the eighth dose are effective and safe for and tolerated by the pediatric subject after each of the third dose and the fourth dose is administered daily to the pediatric subject for a fourth period of time; and (viii) if each of the seventh dose and the eighth dose is determined to be safe for and tolerated by the pediatric subject, changing the seventh dose to a ninth dose of a compound of Formula I, or a pharmaceutically acceptable salt thereof, and changing the eighth dose to an tenth dose of a compound of Formula I, or a pharmaceutically acceptable salt thereof, and orally administering the ninth dose and the tenth dose to the pediatric subject, wherein each of the ninth dose and the tenth dose is administered daily; wherein each of the ninth dose and the tenth dose does not exceed 2 mg/kg; and wherein the total amount of the compound of Formula I administered daily to the pediatric subject does not exceed 135 mg.

In some embodiments, the third dose does not exceed twice the amount of the first dose and the fourth dose does not exceed twice the amount of the second dose. In some embodiments, the third dose does not exceed 2.5 times the amount of the first dose and the fourth dose does not exceed 2.5 times the amount of the second dose.

In some embodiments, the fifth dose does not exceed twice the amount of the third dose and the sixth dose does not exceed twice the amount of the fourth dose.

In some embodiments, the seventh dose does not exceed 1.5 times the amount of the fifth dose and the eighth dose does not exceed 1.5 times the amount of the sixth dose.

In some embodiments, the ninth dose does not exceed 1.5 times the amount of the seventh dose and the tenth dose does not exceed 1.5 times the amount of the eighth dose.

In some embodiments, the first period of time is at least 7 days (e.g., 7 to 11 days). In some embodiments, the second period of time at least 7 days 7 days (e.g., 7 to 11 days). In some embodiments, the third period of time is at least 7 days (e.g., 7 to 11 days). In some embodiments, the fourth period of time is at least 7 days (e.g., 7 to 11 days).

In some embodiments, the first dose and the second dose are administered simultaneously. In some embodiments, the third dose and the fourth dose are administered simultaneously. In some embodiments, the fifth dose and the sixth dose are administered simultaneously. In some embodiments, the seventh dose and the eighth dose are administered simultaneously. In some embodiments, the ninth dose and the tenth dose are administered simultaneously.

In some embodiments, the epileptic disorder is infantile spasm syndrome.

In some embodiments, the pediatric subject is 2-12 years old. In some embodiments, the pediatric subject is from about 0-2 years old. In some embodiments, the pediatric subject is from 2-4 years old. In some embodiments, the pediatric subject is from 4 to 12 years old. In some embodiments, the pediatric subject is from 12-18 years old.

In some embodiments, the pediatric subject is up to 18 months old. In some embodiments, the pediatric subject is less than 18 months old. In some embodiments, the pediatric subject is from 2 to 14 months old.

In some embodiments, the epileptic disorder is caused by or associated with a mutation in the pediatric patient, wherein the mutation is a GRIN2A gain-of-function mutation, a GRIN2B gain-of-function mutation, a GRIN1 gain-of-function mutation, or a GRIN2D gain-of-function mutation. In some embodiments, the epileptic disorder is a GRIN-related epilepsy. In some embodiments, the epileptic disorder is a GRIN2B-related epilepsy. In some embodiments, the epileptic disorder is an early-onset epilepsy.

In some embodiments, the epileptic disorder is caused by or associated with focal cortical dysplasia (e.g., focal cortical dysplasia type I or focal cortical dysplasia type II) in the pediatric subject.

In some embodiments, the method comprises identifying the focal cortical dysplasia (e.g., focal cortical dysplasia type I or focal cortical dysplasia type II) with magnetic resonance imaging (MRI).

In some embodiments, the epileptic disorder is caused by or associated with tuberous sclerosis complex in the pediatric subject.

In some embodiments, the pediatric subject suffers from a motor seizure. In some embodiments, the motor seizure is generalized onset seizure or focal seizure.

In some embodiments, the generalized onset seizure is bilateral, tonic, clonic, atonic, myoclonic, or any combination thereof. In some embodiments, the generalized onset seizure is tonic, clonic, atonic, myoclonic. In some embodiments, the generalized onset seizure is tonic and clonic. In some embodiments, the generalized onset seizure is myoclonic and atonic. In some embodiments, the generalized onset seizure is tonic, clonic, and myoclonic.

In some embodiments, the generalized onset seizure is bilateral.

In some embodiments, the focal seizure is bilateral hyperkinetic or clonic.

In some embodiments, the motor seizure is a drop seizure that leads to trunk, or head and leads to a fall, injury, or slumping.

In some embodiments, the pediatric subject suffers from a drug-resistant seizure.

In some embodiments, the pediatric subject was administered at least one prior therapy to treat the epileptic disorder. In some embodiments, the pediatric subject was administered at least two prior therapies to treat the epileptic disorder.

In some embodiments, each of the therapies administered to treat the epileptic disorder is independently selected from surgery, vagus nerve stimulation, and anti-seizure medication.

In some embodiments, the anti-seizure medication is selected from brivaracetam (Briviact®), cannabidiol oral solution (Epidiolex®), carbamazepine (e.g., carbamazepine-XR), cenobamate, clobazam (Onfi® or Sympazan™ or Frisium), clonazepam, diazepam (e.g., diazepam nasal, diazepam rectal), divalproex sodium (Depakote®), valproic acid (Depakene®), oxcarbazepine (Trileptal® or Oxtellar XR), lamotrigine (Lamictal®), and phenytoin (Dilantin®).

In some embodiments, the method results in a reduction of seizure frequency of about 50%, about 55%, about 60%, about 65%, about 70%, about 75%, about 80%, about 85%, about 90%, about 95%, about 96%, about 97%, about 98%, or about 99% from baseline. In some embodiments, the method eliminates seizures.

The Clinical Global Impression Change (CGI-C) scale is a clinician measure of a change of a symptom or condition, using a single item, 7-point-scale. The CGI-C scale ranges from 1 ("Very much improved") to 7 ("Very much worse"). Clinicians rate change based on the totality of a clinical examination. In some embodiments, an improvement in a CGI-C score is a change toward 1 ("Very much improved"). In some embodiments, the method results in an improvement from baseline based on a Clinical Global Impression of Change (CGI-C).

The Caregiver Global Impression of Change (CaGI-C) scale is a 7-point caregiver rated scale ranging from 1 ("Very much improved") to 7 ("Very much worse"). In some embodiments, an improvement in a CaGI-C score is a change toward 1 ("Very much improved"). In some embodiments, the method results in an improvement from baseline based on a Caregiver Global Impression of Change (CaGI-C).

IV. Neurobehavioral Disorders

Neurobehavioral disorders relate to behavioral disorders or symptoms associated with brain function or structure. Examples of neurobehavioral disorders include, but are not limited to, irritability, mood disorder, movement disorder, sleep disorder, or self-injurious behavior.

Neurobehavioral disorders may be a symptom caused by or associated with encephalopathy, a disease of the brain that alters brain function or structure. Encephalopathy may be caused by or associated with brain injury (e.g., traumatic brain injury, e.g., chronic traumatic brain injury), infection (e.g., bacterial, viral, or prion), metabolic dysfunction, mitochondrial dysfunction, seizure (e.g., epileptic seizure), exposure to toxin (e.g., solvent, metal, or radiation), or trauma.

GRIN1, GRIN2A, GRIN2B, and GRIN2D genes have been identified in individuals with various neurodevelopmental disorders. Individuals with these GRIN variants present with conditions such as behavioral disorders (e.g., neurobehavioral disorders).

The GRIN genes encode for subunits of the ionotropic N-methyl-D-aspartate (NMDA) glutamate receptor, which is widely expressed in the central nervous system (CNS) and critical to normal brain development and activity-dependent synaptic plasticity. Glutamate is the major excitatory neurotransmitter in the mammalian CNS and is responsible for synaptic transmission in approximately half of the synapses in the forebrain. The hetero-tetrameric NMDA receptor is composed of 4 subunits; typically 2 glutamate NMDA receptor subunits 1 (GluN1, also known as NR1; coded by GRIN1) and 2 GluN2 subunits (also known as NR2; coded by GRIN2), of which there are 4 distinct isoforms A-D. Under physiological conditions the subunits bind their respective ligands glycine and glutamate and result in membrane depolarization. Aberrant or abnormal expression (e.g., overexpression) of proteins (e.g., the NDMA receptor subunit NR2B) may cause or be associated with neurobehavioral disorders or symptoms thereof.

There are no specific treatments available that have shown to be effective in treating neurobehavioral symptoms that are often observed in patients with GRIN-related disorder. These symptoms can include irritability, self-injurious behavior, and other typical autism spectrum disorder symptoms such as social communication impairment and restricted interests and repetitive behaviors that often fully meet diagnostic criteria for autism spectrum disorder.

Definitions

The term "about" refers to a value that is within 10% above or below the nominal value. For example, the term "about 100 mg" indicates a range of from 90 mg to 110 mg.

The term "AUC" refers to the area under the time versus plasma concentration after administration of a compound (e.g., radiprodil or a pharmaceutically acceptable salt thereof). The term "$AUC_{0-24h}$" denotes the area under the time versus plasma concentration curve from timepoint 0 to 24 hours. The term "$AUC_{inf}$" denotes the area under the time versus plasma concentration curve from timepoint 0 to infinity. AUC values can be determined by known methods in the art.

The term "$C_{max}$" refers to the maximum serum concentration of a compound (e.g., radiprodil or a pharmaceutically acceptable salt thereof) following administration of the compound.

Disease, disorder, and condition are used interchangeably herein.

In general, the "effective amount" of a compound refers to an amount sufficient to elicit the desired biological response. As will be appreciated by those of ordinary skill in this art, the effective amount of a compound of the present disclosure may vary depending on such factors as the desired biological endpoint, the pharmacokinetics of the compound, the disease being treated, the mode of administration, and the age, health, and condition of the subject.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^-(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

The term "$t_{max}$" refers to the timepoint where $C_{max}$ is achieved following administration of a compound (e.g., radiprodil or a pharmaceutically acceptable salt thereof).

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

Alternative Embodiments

The present disclosure, in an alternative embodiment, also embraces isotopically labeled compounds which are identical to those recited herein, except that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}p$, $^{35}S$, $^{18}F$, and $^{36}Cl$, respectively. For example, a compound of the disclosure may have one or more H atom replaced with deuterium.

"Radiprodil" refers to the compound of Formula I as described herein and has the structure:

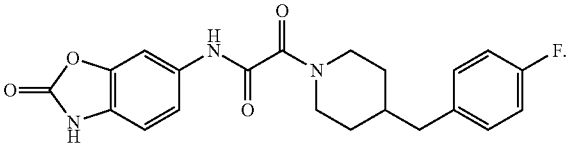 [SMILES: O=C(Nc1ccc2[nH]c(=O)oc2c1)C(=O)N1CCC(Cc2ccc(F)cc2)CC1]

Radiprodil is a negative allosteric modulator of the NMDA (N-methyl D-aspartate) receptor.

A person of skill in the art would understand that any reference to radiprodil, whether in the present application or a prior related application, corresponds to the compound having the following structure:

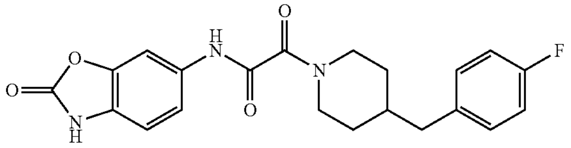 [SMILES: O=C(Nc1ccc2[nH]c(=O)oc2c1)C(=O)N1CCC(Cc2ccc(F)cc2)CC1]

as is known in the art. For the sake of clarity, all prior representations of radiprodil, whether in the present application or a prior related application, should be replaced with the above structure.

EXAMPLES

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Example 1. Synthesis of Radiprodil

An exemplary synthesis of radiprodil is provided in WO2003/010159, which is incorporated herein by reference.

Example 2. A Clinical Study of Radiprodil in the Treatment of Infantile Spasms This is a clinical study of radiprodil in the treatment of pediatric patients having infantile spasm disorders. The clinical study includes the determination in each patient of a dose that should not be exceeded to avoid unjustified safety risks and poorer tolerability. Such a dose limit of radiprodil is identified by determining, in each patient, the dose of Radiprodil associated with a plasma concentration known to saturate the NR2B receptor.

Efficacy will be determined on the effect on seizure frequency where a reduction of seizure severity and frequency of a certain level (generally 50%) will be considered relevant.

For example, each patient's starting dose is set at 0.1 mg/kg as the minimal effective dose. If the patient does not show a sign of efficacy, and no tolerability or safety issues are observed after two weeks, a dose increment to the next dose level of 0.21 mg/kg will be made. If a lack of efficacy and good safety and tolerability is exhibited by the patient, the dose will be escalated up to the top dose of 2 mg/kg. This is the dose expected to be associated with 80% to 100% target occupancy of NR2B by Radiprodil.

Example 3. A Clinical Study of Radiprodil in the Treatment of Drug-Resistant Seizures Investigational Product (IP): Radiprodil. This example describes an open-label, multicenter phase 1B study being conducted to evaluate the safety, tolerability, and pharmacokinetics (PK) of multiple individually titrated doses of radiprodil and to assess the treatment effect on seizures in participants with drug-resistant seizures caused by gain-of-function (GoF) variants in the GRIN1, GRIN2A, GRIN2B, or GRIN2D genes (GRIN2B GoF variants in the US only).

Objectives and Endpoints

The primary objectives of this study are to determine the safety and tolerability of multiple individually titrated doses of radiprodil as an add-on therapy to standard of care (SOC) in pediatric participants; establish a safe and well-tolerated dose; and to determine the pharmacokinetics (PK) and plasma exposure of radiprodil. Endpoints of these primary objectives include: adverse events (AEs), serious adverse events (SAEs), and adverse drug reactions (ADRs) (frequency, type, severity, and duration); changes in vital signs; physical examination findings; 12-lead electrocardiogram (ECG) findings; clinically significant changes in laboratory parameters; emergence of new seizure types; occurrence of suicidal ideation or behavior; determination of the maximum tolerated dose of radiprodil based on safety and tolerability data; and plasma concentrations of radiprodil.

Additional objectives of this study are to include evaluating initial signs of efficacy on frequency and severity of epileptic seizures in those participants with seizures; to evaluate initial signs of efficacy of radiprodil on additional central nervous system (CNS) features including motor symptoms, sleep, and quality of life; and to determine the PK and the plasma exposure of radiprodil major metabolites obtained at different doses. Endpoints of these additional objectives include: change from baseline to end of treatment in seizure frequency from daily seizure electronic diary (eDiary); percent change from baseline to end of treatment in video electroencephalogram (V-EEG) seizure burden (e.g., seizure type, severity, and frequency recorded during V-EEGs); seizure free days and longest period with no seizures; change from baseline to end of treatment in behavioral features as measured by aberrant behavior checklist-community (ABC-C); disorder features as measured by gross motor function measure (GMFM), sleep disturbance scale for children (SDSC), quality of life (Pediatric Quality of Life Inventory [PedsQL]), Caregiver Burden Inventory (CBI), and global impression (Caregiver Global Impression of Change [CaGI-C]), and Clinical Global Impression of Change [CGI-C] scales); and plasma concentrations of the 2 major metabolites of radiprodil.

Study Design

Overall Study Design and Plan

This is a global, open-label, multicenter, phase 1B study to evaluate the safety, tolerability, and PK of multiple individually titrated doses of radiprodil and to assess the treatment effect on seizures and behavioral symptoms in 2 cohorts of pediatric participants: 1 cohort of participants with drug resistant seizures (with or without behavioral symptoms) (Cohort 1) and 1 cohort of participants with behavioral symptoms (but no qualifying seizures) (Cohort 2) caused by GoF variants in the GRIN1, 2A, 2B, or 2D genes (GRIN2B GoF variants only in the US). These GoF variants are gene mutations that cause an increased sensitivity of NMDA receptors to glutamate or through decreased inhibition by magnesium, altered affinity to glycine, or other relevant changes considered to increase NMDA transmission. Drug-resistant seizures are defined as a failure to respond to at least 2 antiseizure medication (ASM) therapies taken at adequate doses for an appropriate duration with assured medication adherence as determined by the treating physician. Participants with seizures to be enrolled in the first cohort should have at least 1 observable motor seizure per week and ≥4 observable motor seizures in the prospective 4-week Observation Period.

Behavioral symptoms as well as motor function, sleep, and developmental delays will be documented and quantified using the following scales and assessments: ABC C, GMFM, SDSC, PedsQL, CBI, Clinical Global Impression—Severity scale (CGI-S), CGIC, and CaGI-C. Participants with behavioral symptoms to be enrolled in the second cohort should have a CGI-S score ≥4 at the Screening Visit and Day −1 of Visit T1.

In the US, the study will open Cohort 1 first. At sites that are not located in the US, the 2 cohorts will be run simultaneously, and participants will be enrolled in each of them based on their meeting the respective entry criteria for each cohort.

After the first 4 participants (sentinel participants) have completed at least their last titration visit (i.e., the end of Titration Period), the SRC will review the available safety and seizure type and frequency data of the participants as well as EEG data. The decision to proceed with the same dose until the end of the Maintenance Period will be made after review of the safety data by the SRC and the sponsor. This will also allow for SRC and DSMB review and approval of the enrollment of any GRIN2B participants in the US with a behavioral/motor phenotype who do not qualify based upon seizure requirements for Cohort 1 but otherwise meet entry criteria for Cohort 2. It must also approve the start of dosing of the 5th and subsequent participants and will discuss the recommendation with the DSMB.

All participants will be encouraged to remain on their stable SOC for the duration of the study. However, adjustments to SOC are permitted as determined by the investigator and must be captured within the electronic case report form (eCRF).

Globally, the goal is to obtain at least 24 evaluable participants (12 in Cohort 1 and 12 in Cohort 2 inclusive of study participants in the global Phase 1B protocol). To achieve at least 12 evaluable participants in each of the 2 study cohorts, it is planned to screen a sufficient number of participants with characterized GRIN1, 2A, 2B, or 2D genes GoF variants. In the US, eligible participation is limited to participants with GRIN2B GoF variants.

Participants can be rescreened only once in exceptional cases at the discretion of the investigator and with approval from the medical monitor.

Participants who discontinue the study early may be replaced as appropriate; therefore, the total sample size may exceed 24 participants in order to ensure an appropriate evaluable dataset. Should the study safety, PK, and initial efficacy objectives be met with fewer than 12 participants in each of the 2 cohorts globally, then recruitment may be halted early for 1 of the 2 cohorts or both. In Cohort 1, participant's must have had at least 1 observable motor seizure per week and ≥4 observable motor seizures (generalized or focal) during the prospective 4-week Observation Period and failed to obtain adequate seizure control with at least 2 ASMs used at appropriate dose and duration with assured medication adherence. Participants will be excluded if they have any clinically relevant medical, neurologic, or psychiatric condition and/or behavioral disorder that would preclude or jeopardize the participant's safe participation or the conduct of the study according to the judgement of the investigator. Outside of the US, participants will not be eligible if they have any clinically significant laboratory or ECG abnormalities or severe hepatic dysfunction (Child-Pugh grade C). In the US, participants are not eligible if they have any clinically significant laboratory or ECG abnormalities, moderate or severe hepatic dysfunction (Child-Pugh grade B or C), or severe renal impairment.

In the US, the study will consist of the following periods: A Screening Period of up to 35 days, including a prospective Observation Period of 4 weeks (to assess baseline seizure frequency and type and severity of behavioral symptoms), a Titration Period of up to 53 days, a Maintenance Period on the highest tolerated dose of up to 41 days, and a tapering period of up to 15 days (recommended to be based on 3 steps of 5 days each at doses representing a reduction of 25% of the full dose—i.e., 75%, 50%, and then 25%—according to the evaluation by the investigator) to reduce the drug exposure prior to study completion.

At the end of the Maintenance Period, US participants will taper off the investigational product (IP). The duration of the Maintenance and Tapering Periods will be adjusted based on the duration of the Titration Period, which will result in a total treatment duration including the anticipated tapering period of no more than 13 weeks. After tapering from the IP, participants will complete a Safety Follow up Period of 2 weeks. At sites that are not located in the US, after completing the Maintenance Period, eligible participants may have the option to continue with radiprodil treatment during a long-term extension period of the study. Participants who choose not to participate or are not eligible for the long-term extension period will taper off the IP.

After signing the informed consent form (ICF) (consent by the caregivers and assent by the participants, as applicable and according to local regulatory requirements) at the Screening Visit, participants will enter the Screening Period. During the Observation Period, observable seizures with motor component will be calculated from the eDiary. Identification of prevalent observable motor seizures will be determined for each participant with seizures. Caregivers will also record other, non-motor seizure types and possible seizure-related phenomena in the eDiary. Participants meeting all eligibility criteria on Day −1 of Visit T1 will enter the Titration Period and be admitted to the site for Visit T1. Participants will visit the site for a minimum of 1 day, with the potential for overnight stays up to 3 days. Administration of the IP, radiprodil, orally twice daily (bis in die [bid]), will start on Day t1 of Visit T1.

Participants will either visit the site for each of the subsequent titration visits T2 (Day t8+4 days), T3 (Day t15+4 days), T4 (Day t22+4 days), and T5 (Day 29+4 days) or undergo the titration procedure at home, under the remote supervision of the investigator. An overnight stay (or hotel stay) before and after a site-based titration day is allowed as deemed necessary based on practical considerations and taking into account participant and caregiver preference.

Participants will continue to receive radiprodil at home in addition to their SOC treatments. During the Titration Period, participants will take their assigned radiprodil dose for 7 to 11 days until a dose escalation may be performed at the next visit (Visits T2, T3, T4, and T5), again subject to logistical/travel considerations.

During the Titration Period, adaptive criteria based on physiologically-based pharmacokinetic (PBPK) modelling will be used to determine the individual dose escalation. In the US, a maximum of 4 dose escalations beyond the starting dose level of 0.05 mg/kg are expected to be made during the Titration Period. For sites located not in the US, a maximum of 3 dose escalations will be considered for each participant during the Titration Period. The decision on the dose escalation, the escalated dose, and continuation of the maximum tolerable dose will be made by the safety review committee (SRC). This decision will be based on the safety/tolerability profile observed in each individual participant and their radiprodil plasma concentration as measured at the current dose level.

In the US, based on the dedicated PBPK model, the increment will be a dose expected to give no more than a 2-fold higher plasma concentration according to the dedicated PBPK model for the first 2 dose escalations. The subsequent dose increment will be based on a 1.5-fold increment that is also based on the plasma concentrations and the derived dose based on the PBPK model. The last escalation to the top dose that is approaching the PK study limit will be with a fold increase that will be determined appropriately for not exceeding the exposures at the NOAEL in the 13-week dog study for both $C_{max}$ and AUC achieved at a dose 1.5 mg/kg/day.

The decision to move on to the next dose level will be decided by the SRC, based on the observed PK data and the absence of clinically relevant safety and tolerability events as determined by the escalation/stopping criteria described further below. In the US, the highest dose to be given to each of the participants will be capped at radiprodil concentrations expected to achieve a $C_{max}$ of 722 ng/ml and $AUC_{0-24h}$ of 3751 ng×hour/mL (±90% confidence interval). In addition, at all sites globally, the top dose will not exceed either a total daily dose of 135 mg or 2 mg/kg bid (4 mg/kg daily) for participants <33 kg (participants weighing ≥33 kg will be restricted to the 135 mg/day limit).

At the sites outside of the US, at the second and subsequent Titration Visits, SRC will meet prior to dose escalation to decide whether to proceed to the next dose level and (if so) the increment to be adopted, based on the following criteria:

- The previous dose was sufficiently well tolerated to suggest that the next planned dose has a reasonable likelihood of being acceptably tolerable (i.e., if an AE that is likely to be closely correlated to dose level occurred with moderate or severe intensity at the previous dose, then any further escalation should be minimal, or should not occur);
- The next dose will be expected to give no more than a 2.5-fold higher plasma concentration according to the PBPK model;
- The next dose is predicted not to exceed the exposure anticipated to produce an approximately 80% (±5%) NR2B receptor occupancy;
- The next dose is predicted to be below the plasma exposure at the no observed adverse effect level plasma concentration observed in the 4-week juvenile rat study (i.e., a $C_{max}$ of 1404 ng/ml and $AUC_{0-24h}$ of 9,555 ng×h/mL); and
- The next dose will not exceed either of: A total daily dose of 135 mg or 2 mg/kg bid (4 mg/kg daily) for participants <33 kg (participants weighing ≥33 kg will be restricted to the 135 mg/day limit).

Based on these criteria, the top exposure limit is currently perceived to be the highest acceptable benefit-risk ratio. After the first 4 participants (sentinel participants) have completed at least their last titration visit (i.e., the end of Titration Period), the SRC will review the available safety and seizure type and frequency data of the participants as well as EEG data. The decision to proceed with the same dose until the end of the Maintenance Period will be made after review of the safety data by the SRC and the sponsor. This will also allow for SRC and DSMB review and approve the enrollment of any GRIN2B participants in the US with a behavioral/motor phenotype who do not qualify based upon seizure requirements for Cohort 1 but otherwise meet entry criteria for Cohort 2. It must also approve the start of dosing of the 5th and subsequent participants and will discuss the recommendation with the DSMB. If a participant does not tolerate the IP after a dose escalation, a dose reduction is allowed. All dose changes by the investigator during the Titration Period should be communicated and discussed with the medical monitor first, provided the safety of the participant allows. If tolerability improves sufficiently to permit consideration of a return to the previous higher dose level, this can be implemented at the discretion of the investigator, again following discussion with the medical monitor. In general, however, if participant safety permits, any other deviations from the planned dosing schedule should be approved by the SRC before implementation. It is to be noted that such additional titration steps may extend the duration of the participant's Titration Period and overall study participation, but the total treatment duration is not to exceed 13 weeks in the US.

Once the appropriate tolerated dose level for a participant has been identified and thus the participant has completed the Titration Period, they will continue to take this dose through the Maintenance Period. However, should tolerability issues emerge, the dose level may be reduced to improve tolerability and (if appropriate) returned to the established dose as and when tolerability improves again. Such adjustments should be discussed with the SRC and/or sponsor and promptly recorded in the eDiary/eCRF to ensure appropriate IP supply management.

At the sites that are not located in the US, participants will visit the site at Visit M1 (Day m1) and receive telephone calls from the site staff at Visits M2 (Day m15±3 days) and M3 (Day m29±3 days) to assess caregivers' eDiary entries (seizure data, daily IP administration volume, participant's usual or prescribed regimen and frequency of rescue therapy for seizures, and data reported by the caregivers based on the integrated scales), any AEs, and changes to concomitant medications. Predose PK samples at Visits M2 and M3 may either be collected at the participants home or optionally at a hotel/hospital, based on the travel distance. The assessments scheduled for Visit M4 (Day m50±3 days) will also be performed at the site for participants who terminate the study early.

In the US, the study visits will be scheduled as follows: If the last dose escalation occurs at Visit T5 (highest dose), Visit M1 will be scheduled 7 days (±2 days) after Visit T5. If the highest tolerated dose for a participant is reached earlier (which can occur at Visits T2, T3, T4, or T5), the Titration Period will end, and the same visit will then become Visit M1 of the subsequent Maintenance Period.

Participants will visit the site at Visit M1 (Day m1) and receive a telephone call from the site staff at Visit M2 (Day m18±3 days) to assess caregivers' eDiary entries (seizure data [if applicable], daily IP administration volume, participant's usual or prescribed regimen and frequency of rescue therapy for seizures, and data reported by the caregivers based on the integrated scales), any AEs, and changes to concomitant medications. Predose PK samples at Visit M2 will either be collected at the participant's home or optionally at a hotel/hospital, based on the travel distance. The assessments scheduled for the End-of-Treatment Visit (Visit M3, Day m39±3 days) will also be performed at the site for participants who terminate the study early. The participants will then taper off the IP and then visit the site again at the Safety Follow-up Visit, 2 weeks after the last dose.

During the Titration and Maintenance Periods, caregivers will record the volume of IP administered on each treatment day in the eDiary. Caregivers will also enter the number and type of seizures on a daily basis, including other, nonmotor seizure types and possible seizure-related phenomena. At the Screening Visit, caregivers will be trained to identify, count, and report the participant's seizures and on the use of the eDiary. Seizures confirmed by EEG or V-EEG recording by the investigator will be determined for each participant and analyzed as a secondary outcome. The number, type, and severity of behavioral symptoms will be assessed using the ABC-C, GMFM, and SDSC; other disorder features will be assessed by PedsQL, CBI, and CGIC, and caregivers will assess seizures, and overall condition using the CaGI-C.

Blood samples for PK will be obtained at Visits T1 (predose and 1, 2, 4, 6, 8, 10, and 12 hours after the first dose, with the 12-hour sample taken immediately before the administration of the second dose), T2, T3, T4, T5 (predose and 1, 2, and 5 hours after the first dose), M1, M2 (predose), and M3/early termination (predose and 1, 2, and 5 hours after the first dose). The timepoints and frequency of sampling may be adjusted based on the SRC evaluation on the minimum data needed to protect participant safety and comfort and to fulfill the study objectives. On the days on which participants will visit the site, participants will take their doses at the site in conjunction with the PK sampling schedule.

The plasma concentrations measured at the visits during the Titration Period will be considered for dose escalations. After administration of the first radiprodil dose in all participants, a rapid assay of the PK levels will allow the verification of exposure to radiprodil against the projected levels. If necessary, dosing adjustments by the SRC may be made if the measured exposure parameters (Cmax and AUC) indicate that the measured exposure exceeds the PK study limits. The exact timing and frequency of PK sampling may also be adjusted by the SRC based on emerging PK data from the first participants.

The starting dose for each participant enrolled in the study is set at 0.05 mg/kg and is expected to have a theoretical NR2B occupancy of approximately 25%. The required dose increments will be determined based on individual PK plasma levels (both AUC and $C_{max}$) collected at each visit during the Titration Period.

In the US, based on the dedicated PBPK model, the increment will be a dose expected to give no more than a 2-fold higher plasma concentration according to the dedicated PBPK model for the first 2 dose escalations. The subsequent dose increment will be based on a 1.5-fold increment that is also based on the plasma concentrations and the derived dose based on the PBPK model. The last escalation to the top dose that is approaching the PK study limit will be with a fold increase that will be determined appropriately for not exceeding the exposures at the NOAEL in the 13-week dog study for both $C_{max}$ and AUC achieved at a dose 1.5 mg/kg/day.

The highest dose to be given to each of the participants will be capped at radiprodil concentrations determined as PK study limit ($C_{max}$ of 722 ng/ml and $AUC_{0-24}$ h of 3751 ng×hour/mL (±90% confidence interval).

At sites located not in the US, based on the dedicated PBPK model, the increment will be a dose expected to give no more than a 2.5-fold higher plasma concentration. Each site will be required to complete a seizure identification form (SIF) for each participant. This information will be submitted to the Epilepsy Study Consortium, Inc. (ESCI) after the Screening Visit for review and approval. The SIF will be used to ensure that the seizures are classified accurately. If a new seizure type occurs during the study that was not previously approved by ESCI, a past seizure type (from >1 year prior to screening) reoccurred, or a seizure type was inadvertently omitted, the site will be required to complete a new SIF and submit to ESCI for review and approval.

For V-EEG evaluation, PK sampling, and dose escalations at Visits T1, M1 (US only), and M3, an overnight stay at the site or in suitable accommodation close to the site will be required for all participants. At Visits T2, T3, T4, T5 (US only), and M2, overnight stays will be permitted for site-based visits in accordance with the investigator's evaluation of participant safety and the convenience of the participant and their caregivers and if required to ease an EEG assessment. Dependent upon geography and convenience, Visits T2, T3, T4, T5, M2, and the Safety Follow-up Visit may occur at the site, the participant's home, or at a suitable accommodation close to the site, with the support of appropriately qualified staff.

In the US, a maximum of 4 dose escalations will be considered for each participant, based on the individual radiprodil plasma concentration, safety, and tolerability. If a participant does not tolerate the IP dose after a dose escalation, reductions are allowed. Re-escalation may be permitted once the AE has remitted. Subsequent re-escalation is permitted at a later Titration Visit, if clinically indicated (additional Titration Visits may occur—to be numbered sequentially—to accommodate such circumstances). All dose changes by the investigator should be communicated and discussed with the medical monitor or an SRC member, if possible.

The SRC (including the principal investigator or designee, the PK subject matter expert, and the sponsor's physician/medical monitor) will meet prior to each dose escalation to discuss the PK data and clinical findings and to evaluate the appropriateness of the dosing schedule for each participant. Confirmation by the SRC will not be required prior to a re-escalation to a previously administered higher dose.

After the first 4 participants (sentinel participants) have completed at least their last titration visit (i.e., the end of Titration Period), the SRC will review the available safety and seizure type and frequency data of the participants as well as EEG data. The decision to proceed with the same dose until the end of the Maintenance Period will be made after review of the safety data by the SRC and the sponsor. This will also allow for SRC and DSMB review and approve the enrollment of any GRIN2B participants in the US with a behavioral/motor phenotype who do not qualify based upon seizure requirements for Cohort 1 but otherwise meet entry criteria for Cohort 2. It must also approve the start of dosing of the 5th and subsequent participants and will discuss the recommendation with the DSMB. Multichannel 8- to 24-hour V-EEG will be performed at Visits T1, M1 (US only), and M3, with the priority of obtaining overnight recordings. The results will be reviewed by the investigator and an independent expert EEG reviewer.

The DSMB will meet at least every 3 months to review the data with a focus on safety and tolerability, to assess the risk benefit profile or as required to consider other emerging safety issues, and to determine whether continuation of the study is appropriate.

Participant Withdrawal from the Study and Stopping Rules:

The sponsor or an investigator may discontinue or withdraw a participant from the study for the following reasons:

- Decision by the investigator;
- Decision by the sponsor;
- Decision by regulatory authority;
- Caregiver/participant request;
- Change in compliance with any inclusion/exclusion criterion that is clinically relevant and affects the participant safety, as determined by the investigator, or the integrity of the study data;
- Protocol deviation that is considered to potentially compromise the safety of the participant or the integrity of the study data;
- Unacceptable noncompliance with any relevant study interventions or assessments;
- Any clinically relevant sign or symptom that in the opinion of the investigator warrants participant removal from study intervention;
- Disease progression that compromises the ability of the participant to safely continue in the study, with particular reference to any unexpected worsening of seizures or behavioral symptoms assessed as related to the IP; or
- Pregnancy.

In the US, if a participant discontinues/is withdrawn prematurely (i.e., before the last visit of the Maintenance Period Visit M3), the IP will be tapered off (unless for an emergent safety issue), and an early termination visit will be conducted as soon as possible after the last full dose with the procedures scheduled for Visit M3 and the Safety Follow up Visit if possible. At sites that are not located in the US, any participant whose dosing is permanently discontinued will taper off the IP (unless for an emergent safety issue) and will be encouraged to complete the study or have at least the assessments scheduled for Visit M4 and the Safety Follow-up Visit if possible. Participants who are withdrawn for non-IP related reasons (including coronavirus disease 2019 infection or restrictions) may be replaced following discussion between the investigator and the sponsor and a decision by the SRC.

Participants withdrawn as a result of AEs thought to be related to the IP, as determined by the investigator, may be replaced if study stopping rules have not been triggered. The decision regarding the replacement of participants will be made by the SRC and fully documented. The reason for participant discontinuation or withdrawal from the study will be recorded on the appropriate eCRF.

Study Stopping Criteria:

Dosing across the study will be suspended and an urgent SRC review will occur within 24 hours if either of the following study stopping criteria are met:

- Any SAEs considered at least possibly related to the IP (as judged by investigator) in 2 or more participants, where those SAEs occur in the same body system; or
- Any severe nonserious adverse reaction (i.e., severe nonserious AEs considered at least possibly related to the IP as judged by investigator) in 3 or more participants, where those severe AEs occur in the same body system and lead to the withdrawal of the affected participant.

This decision will be made by the SRC and fully documented. Dosing may only be resumed with the agreement of the DSMB. At this urgent review, the SRC will confirm whether the above criteria have been met and, if so, whether cessation of dosing of all participants within the study should be temporary or permanent.

Thereafter, the DSMB (which will include independent external members) will need to approve any subsequent resumption of dosing and whether any amendments to the study are needed to support this.

Individual Participant Criteria for Withdrawal from IP:

Administration of the IP will be stopped in any individual participant who develops a medical condition (or laboratory abnormality or ECG change) that, in the opinion of the investigator, compromises the participant's ability to participate in the study or the participant's safety. This will include occurrence of any SAE considered at least possibly related to study treatment with specific attention to the onset of new seizure types and to an increased frequency.

If any of the above circumstances occur, the participant should be followed until the condition has resolved, as agreed by the investigator and the sponsor's physician/medical monitor. If a participant discontinues the IP, restarting may be allowed but only after review and approval by the SRC.

In the US, any participant whose dosing is permanently discontinued will be encouraged to complete the study or have at least the assessments scheduled for Visit M3 and the Safety Follow-up Visit if possible. At sites that are not located in the US, any participant whose dosing is permanently discontinued will be encouraged to complete the study or have at least the assessments scheduled for Visit M4 and the Safety Follow-up Visit if possible. The dosing schedule is detailed in Table 1.

TABLE 1

Dosing schedule of individual participants in the US

| Schedule | | Study Day | Proceeds at Dose 1 | Proceeds at Dose 2 | Proceeds at Dose 3 | Proceeds at Dose 4 | Proceeds at Dose 5 |
|---|---|---|---|---|---|---|---|
| Titration | T1 | t1 | 0.05 | 0.05 | 0.05 | 0.05 | 0.05 |
| | T2 | t8 + 4 | 0.05 | Dose 2 | Dose 2 | Dose 2 | Dose 2 |
| | T3 | t15 + 4 | — | Dose 2 | Dose 3 | Dose 3 | Dose 3 |
| | T4 | t22 + 4 | — | — | Dose 3 | Dose 4 | Dose 4 |
| | T5 | t29 + 4 | — | — | — | Dose 4 | Dose 5 |
| | M1 | m1 ± 2 | 0.05 | Dose 2 | Dose 3 | Dose 4 | Dose 5 |
| | M2 | m18 ± 3 | 0.05 | Dose 2 | Dose 3 | Dose 4 | Dose 5 |
| | M3 (EoT) | M39 ± 3 | 0.05 | Dose 2 | Dose 3 | Dose 4 | Dose 5 |

Tapering Recommendation

If a participant is stopping the IP for any reason (premature discontinuation), they should undergo a tapering regimen reflecting the following recommended schedule, namely—the dose of radiprodil should be reduced by 25% of the full dose for each of three 5-day steps i.e., to 75%, 50%, and then 25% before stopping entirely. However, this schedule may be modified at the discretion of the investigator to suit the clinical circumstances, e.g., if a participant is already taking a low dose.

Preclinical Efficacy and NR2B Receptor Occupancy

In-vivo preclinical data have indicated that radiprodil anticonvulsant effects correlate with plasma concentration and NR2B RO. Therefore, this relationship may help guide the definition of the expected therapeutic range.

Radiprodil anticonvulsant efficacy was specifically tested in rats at different time points during postnatal development, using pentylenetetrazole (PTZ) as a convulsant, to induce generalized clonic-tonic seizures. The activity of radiprodil in this juvenile PTZ rat model was tested up to 30 mg/kg, showing efficacy at a dose of 1 mg/kg. The calculated free plasma fraction of an orally administered 1 mg/kg dose is expected to give around 60% occupancy of the NR2B receptor, based on an ex-vivo occupancy study in rodents and assuming a 1:1 brain to plasma ratio, see below for further details. At a dose of 10 mg/kg, roughly corresponding to 90% NR2B occupancy, radiprodil completely blocked the tonic phases of PTZ-induced convulsions in postnatal day 12 and postnatal day 18 rats. The anticonvulsant efficacy of radiprodil was also assessed in an audiogenic seizure model (generalized seizures) in adult mice, showing anticonvulsant activity in the same range of doses/exposures.

Although the in vivo efficacy models used so far to evaluate the anticonvulsant effects of radiprodil are not specific to GRIN2B-related disorder, the data suggest that such effects correlate with NR2B occupancy.

Starting Dose

The starting dose for each participant enrolled in the study will be set at 0.05 mg/kg bid. This dose is expected to have a theoretical NR2B occupancy of approximately 25% and is felt to be an appropriate starting dose because of the following reasons:

- The associated exposure level is more than 20-fold lower (in terms of total $C_{max}$ and AUC) than the NOAEL exposure in the completed juvenile rat toxicology study (100 mg/kg/day);
- It has already been administered to 3 infants for treatment of resistant infantile spasms, in whom radiprodil treatment for up to 34 days was found to be safe and well tolerated.20 In this previous study in infants, 2 participants received doses up to 0.2 mg/kg bid, and plasma exposure both in terms of $C_{max}$ (up to 208 ng/mL), and $AUC_{0-t}$ (up to 1036 ng×h/mL) increased in a linear fashion as expected, based on the PBPK modeling; or.
- It is well below the exposure levels associated with the safe and well tolerated single and multiple doses in adult healthy volunteers. In patients with neuropathic pain, a total daily dose of 135 mg (45 mg tid) up to 14 weeks has been previously administered. The plasma exposures corresponded to a $C_{max}$ of 487±129 ng/ml and an AUC of 9000±2387 ng×h/mL.

Dose Escalation

During the Titration Period, adaptive criteria based on PBPK modelling will be used to determine the individual dose escalation. Individualized predictions including mean and 5th and 95th percentiles will be performed for the first day(s) of low dose therapy, and measured concentration-time data will be superimposed. A decision tree will then be followed regarding the dose escalation strategy based on observed plasma concentrations in relation to predicted values and dose changes necessary to give the required exposures; each dose increase will be contingent on review of the measured concentration-time data for the previous dose. A maximum of 3 dose escalations beyond the starting dose level of 0.05 mg/kg are expected to be made during the Titration Period at the sites not located in the US, and there will be a maximum of 4 dose escalations for the participants at the US sites. Dose escalation will be based on the safety/tolerability profile observed in each individual participant and their radiprodil plasma concentration as measured at the current dose level.

For the sites not located in the US, based on the dedicated PBPK model, the increment will be a dose expected to give no more than a 2.5-fold higher plasma concentration. The PK study limit will be set below the plasma level observed at the NOAEL in the 4-week juvenile rat study (i.e., $C_{max}$ of 1404 ng/ml and $AUC_{0-24}$ h of 9,555 ng×h/mL).

In the US, the increment will be a dose expected to give no more than a 2 fold higher plasma concentration according to the dedicated PBPK model for the first 2 dose escalations. The subsequent dose increment will be based on a 1.5-fold increment that is also based on the plasma concentrations and the derived dose based on the PBPK model. The last escalation to the top dose that is approaching the PK study limit will be with a fold increase that will be determined appropriately for not exceeding the exposures at the NOAEL (1.5 mg/kg/day) in the 13-week dog study for both $C_{max}$ (722 ng/ml) and $AUC_{0-24h}$ (3,751 ng×hour/mL). This exposure is approximately 2-fold lower than the average $AUC_{0-24h}$ (7,063.5 ng×hour/mL) observed at 6-months in the 9-month dog toxicology study (1.5 mg/kg/day) and up to which time no seizures or convulsions were observed.

The decision to move on to the next dose level will be decided by the SRC, based on the observed PK data and the absence of clinically relevant safety and tolerability events as determined by the escalation/stopping criteria.

In addition, at all sites globally, the top dose will not exceed either a total daily dose of 135 mg or 2 mg/kg bid (4 mg/kg daily) for participants <33 kg (participants weighing ≥33 kg will be restricted to the 135 mg/day limit).

If a participant does not tolerate the IP after a dose escalation, a dose reduction is allowed. All dose changes by the investigator during the Titration Period should be communicated and discussed with the medical monitor first, provided that the safety of the participant allows. If tolerability improves sufficiently to permit consideration of a return to the previous higher dose level, this can be implemented at the discretion of the investigator, again following discussion with the medical monitor. In general, however, if participant safety permits, any other deviations from the planned dosing schedule should be approved by the SRC before implementation. It is to be noted that such additional titration steps may extend the duration of the participant's Titration Period and, for non-US locations, overall study participation.

Inclusion Criteria

A participant will be eligible for study participation if they meet all of the following criteria:

- Pediatric participants aged ≥6 months to ≤12 years with GRIN1, 2A, 2B, or 2D gene variants known to result in GoF of the NMDA receptor. In the US, participants need to be aged ≥4 years to ≤12 years with GRIN2B gene variants known to result in GoF of the NMDA receptor

- Participant to be enrolled in the first cohort experiences the following
  - At least 1 observable motor seizure per week and ≥4 observable motor seizures (generalized or focal) during the prospective 4-week Observation Period; or
  - Has failed to obtain adequate seizure control with at least 2 ASMs used at appropriate dose and duration with assured medication adherence (if applicable);
- Participant to be enrolled in the second cohort experiences the following
  - Significant behavioral and/or motor symptoms based on caregiver report with a CGI-S score ≥4 at the Screening Visit and Day −1 of Visit T1;
- Current therapies need to be on a stable dose for at least 4 weeks prior to Screening and should be maintained stable throughout the whole study duration.
- Nonpharmacological treatments such as ketogenic diet should be kept as stable as possible during screening and participation in the study. Changes in antiseizure medication should be discussed with the sponsor in consultation with the investigator;
- Participant's caregivers have signed informed consent and participant has signed assent (if applicable);
- Participant's caregivers are willing and able to complete entries in the eDiary on a daily basis; and
- Participant is 1 of the following:
  - Not of childbearing potential (premenarchal or male/not in possession of a uterus);
  - If of childbearing potential, is nonpregnant (negative serum pregnancy test results at Screening), nonlactating, and practicing 1 of the following medically acceptable methods of birth control:
    - Abstinence from heterosexual intercourse as a lifestyle choice;
    - Hormonal methods such as oral, implantable, injectable, or transdermal contraceptives for a minimum of 1 full cycle (based on the participant's usual menstrual cycle period) before IP administration; or
    - Intrauterine device; or
  - If male, is willing to use a highly effective method of contraception throughout the study period (if sexually active).

Exclusion Criteria

A participant will be excluded from the study if they meet any of the following criteria:

- Participant with any other clinically relevant medical, neurologic, or psychiatric condition and/or behavioral disorder unrelated to GRIN2B that would preclude or jeopardize participant's safe participation or the conduct of the study according to the judgement of the investigator;
- Participant with a body weight <10 kg on Day −1 of Visit T1 for whom a gastric tube is the only possibility for radiprodil dosing;
- Participant with any clinically significant laboratory or ECG abnormalities;
- Participant has severe hepatic dysfunction (Child-Pugh grade C) (in the US: moderate to severe hepatic dysfunction [Child-Pugh grade B and C]);
- Participant has severe renal impairment (in the US only);
- Participants are receiving or have received concomitant administration of strong cytochrome P450 3A4 inducers or inhibitors within 1 month prior to Screening (in the US only);
- Participant has a history of brain surgery for epilepsy or any other reason;
- Participant with any contraindications to radiprodil or with known hypersensitivity to the active substance or the excipients or other chemically closely related substances;
- Participant receiving treatment with contraindicated concomitant drugs such as agonists or antagonists of the glutamate receptor, including but not limited to felbamate, memantine, and perampanel;
- Participant is on treatment with hormonal therapy such as adrenocorticotrophic hormone or prednisolone;
- Participant has participated in any other investigational clinical study within 3 months of Screening; or
- Participant has previously been enrolled in the current study.

Premature Participant Withdrawal

All participants will be advised that they are free to withdraw from participation in this study at any time, for any reason, and without prejudice. The investigator should make every reasonable attempt to keep participants in the study. However, participants must be withdrawn from the study if they withdraw consent to participate. Investigators must attempt to contact participants who fail to attend scheduled visits by telephone or other means to exclude the possibility of an AE being the cause of withdrawal. Should this be the cause, the AE must be documented, reported, and followed as described herein.

The sponsor reserves the right to request the withdrawal of a participant due to protocol deviations or other reasons. The investigator also has the right to withdraw participants from the study at any time for lack of therapeutic effect that is intolerable or otherwise unacceptable to the participant, for intolerable or unacceptable AEs, intercurrent illness, noncompliance with study procedures, administrative reasons, or in the investigator's opinion, to protect the participant's best interest.

If a participant is withdrawn before completing the study, the reason for withdrawal and the date of discontinuation will be recorded on the appropriate page of the eCRF. Whenever possible and reasonable, the evaluations that were to be conducted at Visit M3 in the US or Visit M4 outside of the US, respectively, and the Safety Follow-up Visit of the study should be performed at the time of premature discontinuation.

Discontinuation of Study Intervention

Discontinuation from the IP does not mean discontinuation from the study, and remaining study procedures should be completed as indicated by the study protocol. If a clinically significant finding is identified (including, but not limited to, changes from Baseline) after enrollment, the investigator or qualified designee will determine if any change in participant management is needed. Any new clinically relevant finding will be reported as an AE.

Administration of the IP will be stopped if the participant develops a medical condition (or laboratory abnormality or ECG change) that, in the opinion of the investigator, compromises the participant's ability to participate or the participant's safety. This will include occurrence of any SAE considered at least possibly related to study treatment.

If any of the above circumstances occur, the participant should be followed until the condition has resolved, as agreed by the investigator and the sponsor's physician/medical monitor. If a participant discontinues the IP, restarting may be allowed, but only after review and approval by the SRC. The data to be collected at the time of study intervention discontinuation will include the following: A PK sample (ideally at trough) and safety laboratory panels.

Participant Discontinuation/Withdrawal from the Study

Participants are free to withdraw from participation in the study at any time upon request. In the US, any participant whose dosing is permanently discontinued will taper off the IP (unless for an emergent safety issue) and will be encouraged to complete the study or have at least the assessments scheduled for Visit M3 and the Safety Follow-up Visit if possible. At sites that are not located in the US, any participant whose dosing is permanently discontinued will taper off the IP (unless for an emergent safety issue) and will be encouraged to complete the study or have at least the assessments scheduled for Visit M4 and the Safety Follow-up Visit if possible.

Dosing across the study will be suspended if any of the general stopping criteria described herein. This decision will be made by the SRC and fully documented. Dosing may only be resumed with the agreement of the DSMB.

Additionally, an investigator may discontinue or withdraw a participant from the study for the following reasons:

- Decision by the investigator;
- Decision by the sponsor;
- Decision by regulatory authority;
- Caregiver/participant request;
- Change in compliance with any inclusion/exclusion criterion that is clinically relevant and affects the participant safety, as determined by the investigator, or the integrity of the study data;
- Protocol deviation that is considered to potentially compromise the safety of the participant or the integrity of the study data;
- Unacceptable noncompliance with any relevant study interventions or assessments;
- Any clinically relevant sign or symptom that in the opinion of the investigator warrants participant removal from study intervention;
- Disease progression that compromises the ability of the participant to safely continue in the study, with particular reference to any unexpected worsening of seizures or behavioral symptoms assessed as related to the IP;
- Pregnancy Participants who are withdrawn for non-IP-related reasons (including coronavirus disease 2019 infection or restrictions) may be replaced following discussion between the investigator and the sponsor and a decision by the SRC. Participants withdrawn as a result of AEs thought to be related to the IP, as determined by the investigator, may also be replaced if study stopping rules have not been triggered. The decision regarding the replacement of participants will be made by the SRC and fully documented. The reason for participant discontinuation or withdrawal from the study will be recorded on the appropriate eCRF.

Participants whose caregivers sign an ICF but do not receive the IP may be replaced. Participants whose caregivers sign the ICF, receive the IP, and subsequently withdraw or are withdrawn or discontinued from the study, may be replaced, depending upon whether they have provided sufficient data to support the objectives of the study-which will be determined by the SRC.

A participant will be considered lost to follow-up if they fail to return for scheduled visits and is unable to be contacted by the study site staff. The following actions must be taken if a participant fails to return to the clinic for a required study visit:

- The site will attempt to contact the participant and reschedule the missed visit and counsel the caregivers on the importance of maintaining the assigned visit schedule and ascertain if the participant wishes to and/or should continue in the study;
- Before a participant is deemed lost to follow-up, the investigator or designee will make every effort to regain contact with the caregivers (where possible, 3 telephone calls and, if necessary, a certified letter to the participant's caregivers' last known mailing address or local equivalent methods). These contact attempts should be documented in the participant's medical record or study file; and
- Should the participant's caregivers continue to be unreachable, they will be considered to have withdrawn from the study with a primary reason of lost to follow-up.

Participant Replacement Criteria

Participants who are withdrawn from the study may be replaced in accordance with the criteria described herein. If a substantial number of participants are withdrawn from the study, the sponsor will evaluate the need for developing replacement criteria.

Enrolled participants withdrawn from the study may not reenter. The participant number for a withdrawn participant will not be reassigned to another participant.

Study Stopping Criteria

After the first 4 participants (sentinel participants) have completed at least their last titration visit (i.e., the end of Titration Period), the SRC will review the available safety and seizure type and frequency data of the participants as well as EEG data. The decision to proceed with the same dose until the end of the Maintenance Period will be made after review of the safety data by the SRC and the sponsor. This will also allow for SRC and DSMB review and approve the enrollment of any GRIN2B participants in the US with a behavioral/motor phenotype who do not qualify based upon seizure requirements for Cohort 1 but otherwise meet entry criteria for Cohort 2. It must also approve the start of dosing of the 5th and subsequent participants and will discuss the recommendation with the DSMB. An urgent SRC review will also occur within 24 hours if any of the following study stopping criteria are met:

- Any SAEs considered at least possibly related to the IP (as judged by investigator) in 2 or more participants, where those SAEs occur in the same body system;
- Any severe nonserious adverse reaction (i.e., severe nonserious AEs considered at least possibly related to the IP as judged by investigator) in 3 or more participants, where those severe AEs occur in the same body system and lead to the withdrawal of the affected participant; or.
- If the duration of an individual seizure or the duration of a cluster of seizures for a participant changes by the following categories:

| Baseline seizure duration | Post-treatment seizure duration |
|---|---|
| <5 minutes | 11-30 minutes |
| 5-10 minutes | >30 minutes |
| 11-30 minutes | >30 minutes |

For example, If the seizure duration is <5 minutes for an individual participant and the duration changes to 11-30 minutes, treatment would be stopped. Similarly, if a participant with seizure duration of 5-10 minutes changes to >30 minutes, treatment would be stopped. Treatment will be stopped if a participant's seizure duration increases to >30 minutes.

At this urgent review, the SRC will confirm whether the above criteria have been met and, if so, whether cessation of dosing of all participants within the study should be temporary or permanent.

Thereafter, the DSMB (which will include independent external members) will need to approve any subsequent resumption of dosing and whether any amendments to the study are needed to support this. The DSMB will, in any case, meet at least approximately every 3 months to review the data with a focus on safety and tolerability, to assess the risk benefit profile or as required to consider other emerging safety issues, and to determine whether continuation of the study is appropriate.

The decision of the DSMB on the need for cessation will take into account the risk/benefit evaluation for each participant and the potential for harm from the sudden withdrawal of a neuroactive medication in this population. Whatever the decision of the DSMB, it will be submitted to the local health authority and IRB as soon as possible within 7 days for their review. Other stopping rules that will result in temporary hold or termination of the study:

- The sponsor decides to terminate the study and no further dosing is scheduled; or
- A health authority or IRB requests a hold on dosing or study termination

Example 4. Results from a Clinical Study of Radiprodil in the Treatment of Drug-Resistant Seizures Results from an open-label, multicenter phase 1B study, as described in the previous Example, are described below.

A seizure cohort of patients from 6 months to 12 years of age with known GoF variants confirmed via method described in Myers, et al., Hum Mol Genetics. 2023, 32:2857-2871, was enrolled. The patients had drug-resistant seizures with or without behavioral symptoms. Patients also had ≥1 weekly countable motor seizure (CMS) with ≥4 generalized or focal seizures during the observation period. Motor seizures included drop seizures; generalized onset seizures included tonic-clonic, tonic, bilateral clonic, atonic, myoclonic-atonic, and myoclonic-tonic-clonic seizures; and focal seizures included seizures with bilateral hyperkinetic motor features and clonic seizures.

There was a high level of seizure activity at baseline in the seizure cohort with a mean of 37.0 and a median of 25.5 CMS per patient (range of 4.8 to 85.9).

Primary endpoints included safety, tolerability, and radiprodil plasma concentrations. Key secondary endpoints (aka, change from baseline in observable daily CMS frequency using an electronic diary (eDiary)), included ≥50%, ≥90%, and 100% reductions from baseline in seizure frequency; proportion of seizure-free days; and Clinical Global Impressions of Change (CGI-C) and Caregiver Global Impressions of Change (CaGI-C), from baseline to the end of the maintenance period.

Study Design: Radiprodil was initiated at 0.05 mg/kg twice daily (BID) and incrementally increased based on the observed exposure determined by a dedicated physiologically based pharmacokinetic model, predicted receptor occupancy, and safety, and tolerability as assessed by the safety review committee (SRC), as shown in FIG. 1.

- Part A: ≤5-week screening period, an individualized dose escalation phase, and an 8-week maintenance period.

- Part B: Assessment of the long-term safety of radiprodil.
- Radiprodil doses during the Maintenance Period ranged from 0.25 to 1.96 mg/kg (median: 0.783 mg/kg) administered BID orally or by feeding tube.
- The range of the titration period was 5.1 to 21.6 weeks (median: 8.5 weeks).

Results: Baseline demographic and disease characteristics were generally representative of the target population. A predefined data cut was performed when 12 patients completed Part A. Patients had a high degree of seizure activity at baseline despite being treated with multiple ASMs.

TABLE 2

Baseline demographic and disease characteristics

| Baseline Characteristics | Seizure Cohort (n = 8) |
|---|---|
| Age, years, mean (SD) | 5.1 (3.3) |
| Sex, n (%) | |
| Female | 5 (62.5) |
| GRIN Type, n (%) | |
| GRIN1 GoF | 3 (37.5) |
| GRIN2A GoF | 3 (37.5) |
| GRIN2B GoF | 2 (25.0) |
| Baseline 28-day CMS frequency, median (min, max)[a] | 25.5 (5, 86) |
| Clinical Global Impression-Severity, n (%) | |
| Most extremely ill (7) | 4 (50.0) |
| Severely ill (6) | 4 (50.0) |
| Markedly ill (5) | 0 |
| Number of Concomitant ASMs[b], mean (SD) | 3.0 (1.8) |

ASM, antiseizure medication.

[a]28-day seizure frequency is calculated as: (No. of seizures)/(No. of days seizures were assessed) × 28 days.

[b]Antiseizure medications are defined as medications with World Health Organization Anatomical Therapeutic Chemical Classification System level 2 of N03.

Treatment emergent adverse event (TEAE): Radiprodil treatment appeared to be generally well-tolerated. Pyrexia, diarrhoea, and respiratory tract infection were the most common TEAEs. Three patients experienced SAEs, all unrelated to radiprodil treatment. One each of adenovirus infection, bronchiolitis, and viral pneumonia

TABLE 3

Treatment emergent adverse event (TEAE)

| TEAEs, n (%)[a] | Seizure Cohort (n = 8) |
|---|---|
| Any TEAE | 8 (100) |
| Pyrexia | 4 (50.0) |
| Diarrhoea | 2 (25.0) |
| Respiratory tract infection | 2 (25.0) |
| Abnormal behavior | 1 (12.5) |
| Agitation | 1 (12.5) |
| Cough | 2 (25.0) |
| Dystonia | 2 (25.0) |
| Fatigue | 1 (12.5) |
| Gastroenteritis | 2 (25.0) |

Figure 2:
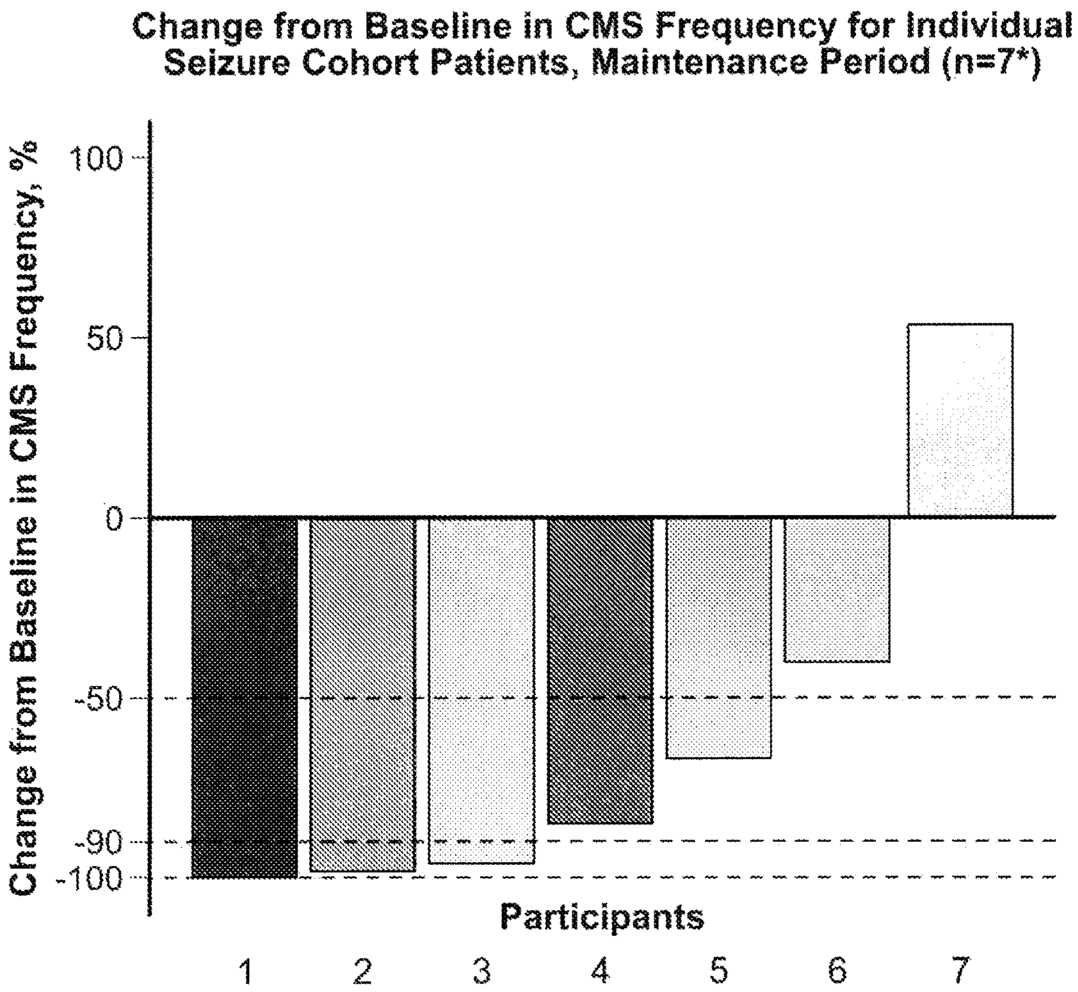
FIG. 2 is a graph illustrating the reduction from baseline in CMS frequency observed for 6 of the 7 seizure cohort patients, as described in Example 4 below.
Figure 3:
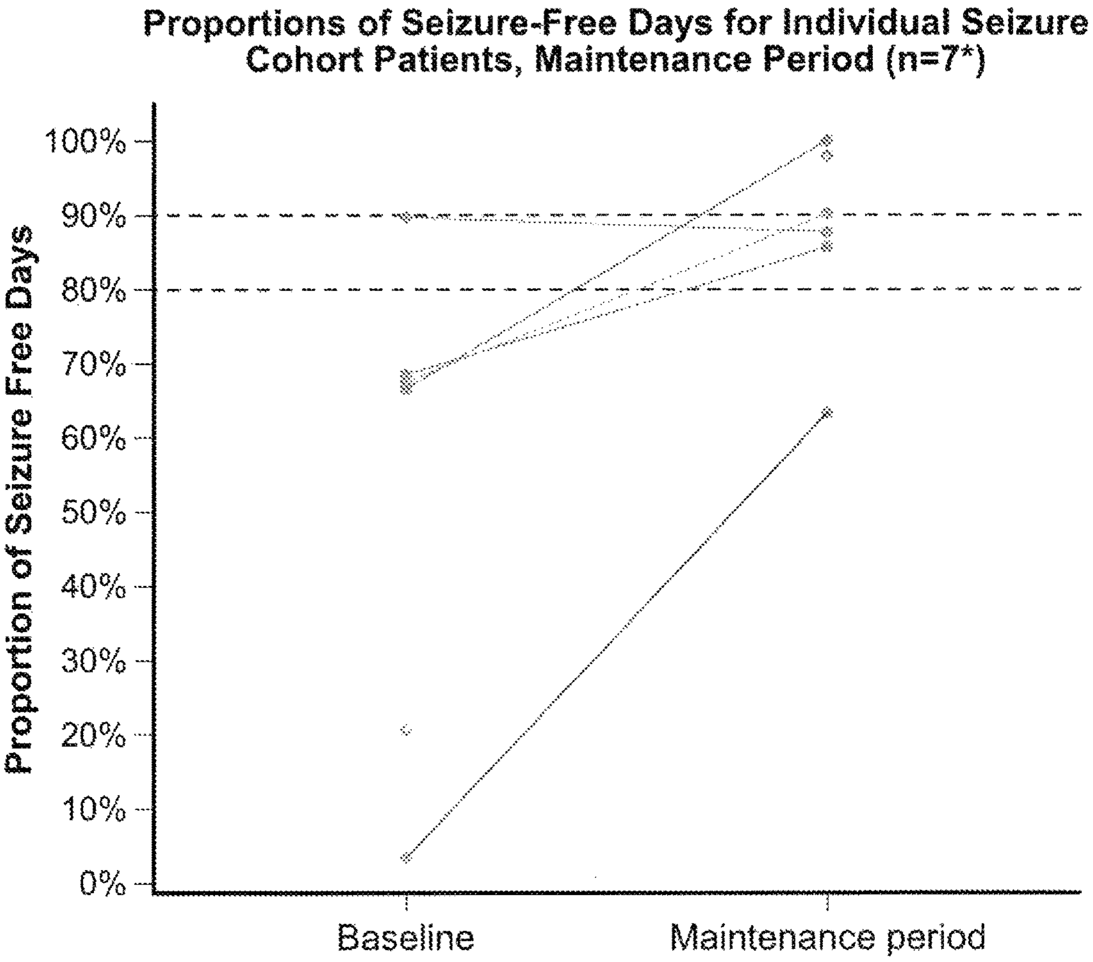
FIG. 3 is a graph illustrating the seizure-free patients in the seizure cohort during 80% of days of the 8-week maintenance period after radiprodil treatment, as described in Example 4 below.

CMS Frequency: 6 of 7 seizure cohort patients experienced reductions from baseline in CMS frequency after radiprodil treatment (FIG. 2). Median reduction in CMS was nearly 86% during the 8-week maintenance period. 71.4%, 42.9%, and 14.3% of patients saw reductions in CMS of ≥50%, ≥90%, and 100%, respectively, during the same period. Additionally, 6 of 7 patients were seizure-free during 80% of days of the 8-week maintenance period after radiprodil treatment (FIG. 3).

Figure 4:
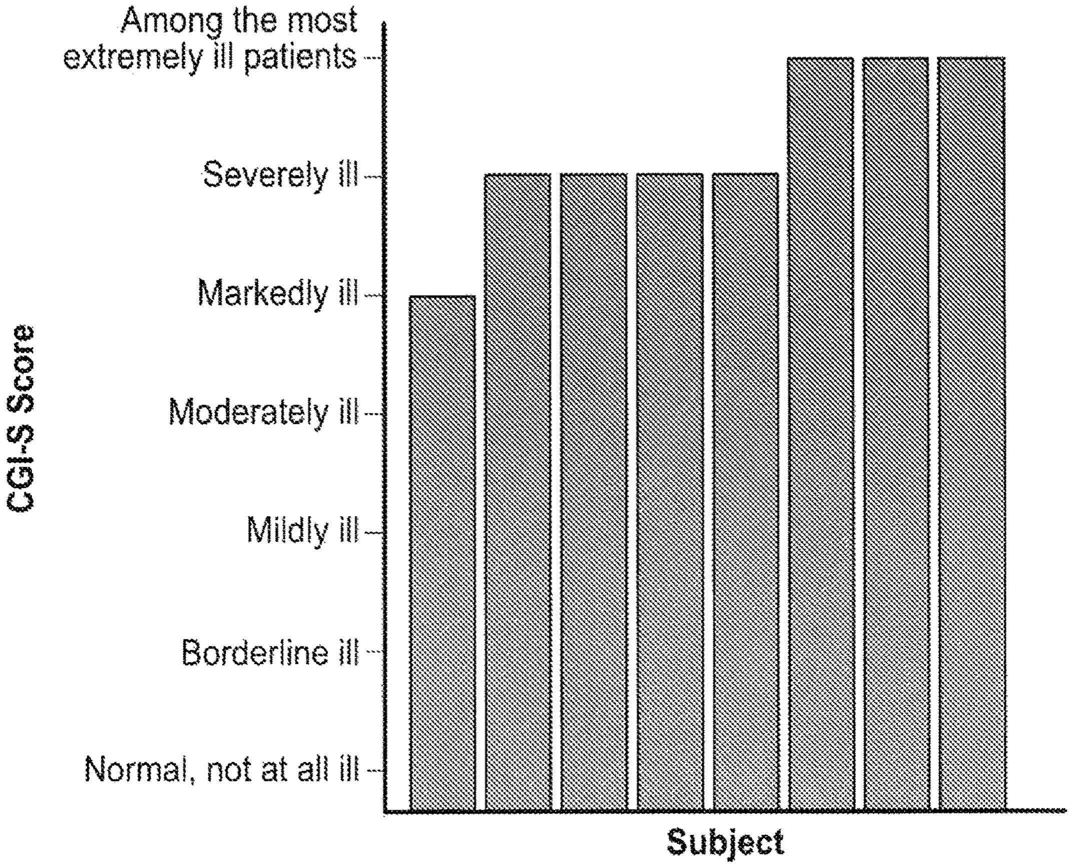
FIG. 4 is a graph illustrating the baseline Clinical Global Impressions of Change (CGI-C) scores observed by clinicians in the phase 1B study of radiprodil, as described in Example 4 below.

Global Impressions of Change: Baseline Clinical Global Impressions of Change (CGI-C) scores are shown in FIG. 4.

Figure 5:
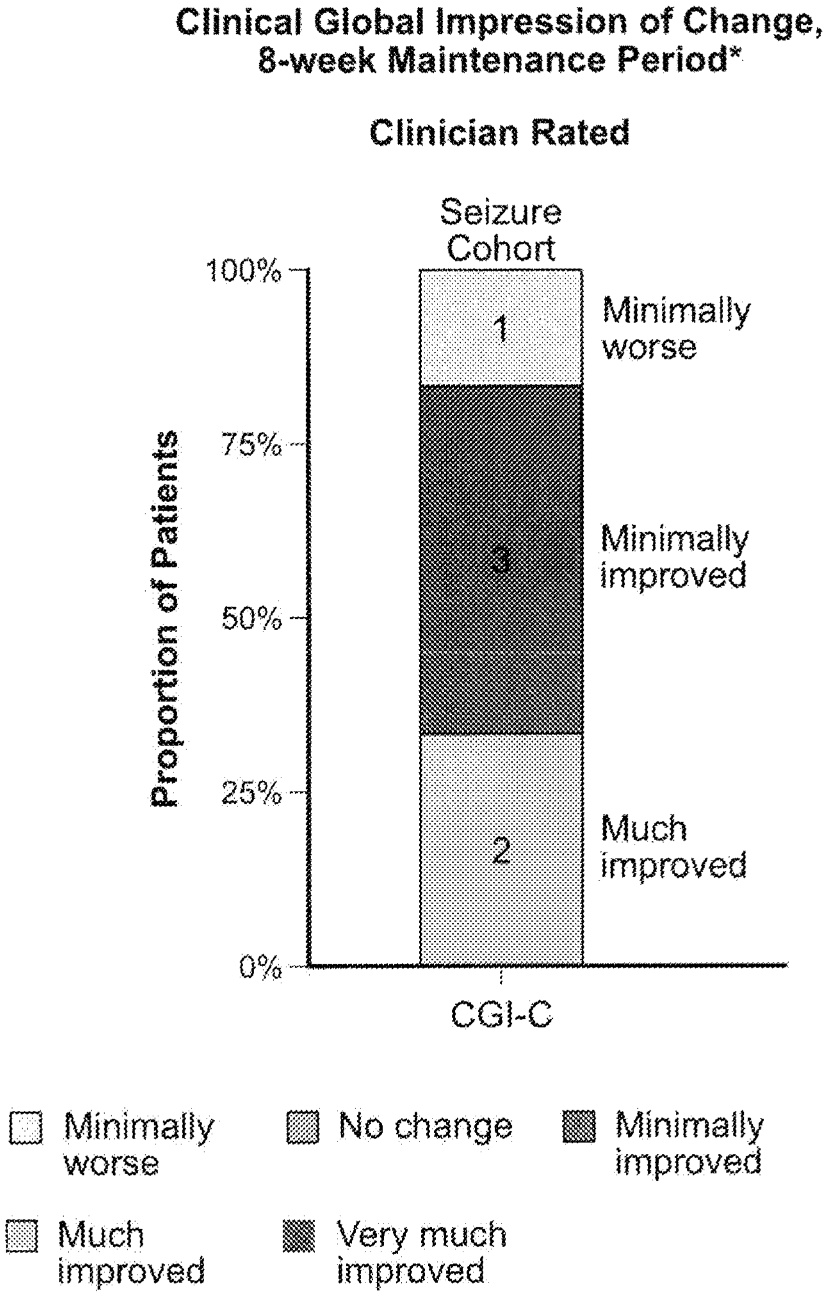
FIG. 5 is a graph illustrating the Clinical Global Impressions of Change (CGI-C) observed during the 8-week maintenance period of a phase 1B study of radiprodil, as described in Example 4 below.
Figure 6:
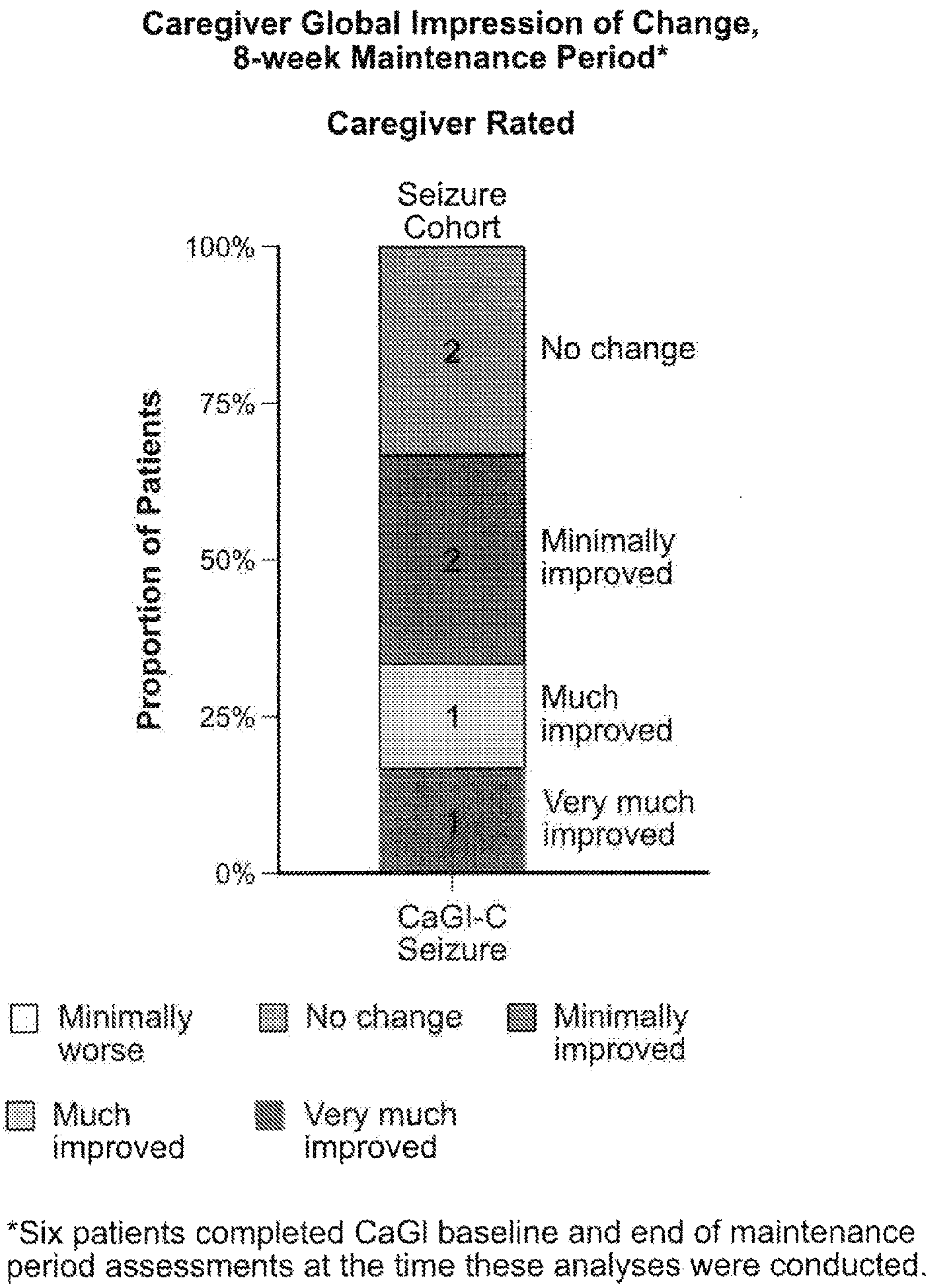
FIG. 6 is a graph illustrating the Caregiver Global Impressions of Change (CaGI-C) observed during the 8-week maintenance period of a phase 1B study of radiprodil, as described in Example 4 below.

Both clinicians and caregivers described clinical improvement in most patients over the course of the study using the Clinical Global Impressions of Change (CGI-C) and Caregiver Global Impressions of Change (CaGI-C), respectively (FIG. 5 and FIG. 6).

Conclusions: Radiprodil appeared to be generally well-tolerated in patients with GRIN-related neurodevelopmental disorder and GoF variants. Most common TEAEs were associated with infection or underlying disease symptoms. A median reduction of nearly 86% in CMS was observed during the 8-week maintenance period in the seizure cohort. Most patients had at least a 50% reduction in CMS frequency, and 6 of 7 patients were seizure-free during 80% of days of the 8-week maintenance period. Both clinicians and caregivers described clinical improvement in most patients using the Clinical and Caregiver Global Impressions of Change Improvements. These results support advancing radiprodil into the next phase of development as a potential treatment for GRIN-related neurodevelopmental disorders.

Example 5. A Phase 3 Study of the Treatment of Seizures

Part A-Randomized Qualifying Seizure Cohort
General

This is a Phase 3 Randomized Qualifying Seizure Cohort study with 1:1 randomization (radiprodil and placebo). Randomization will be stratified by age: less than 2 years old, 2 to 12 years old, and greater than or equal to 13 years old. All patients are required to have a documented mutation in the GRIN1, GRIN2A, GRIN2B, or GRIN2D genes as determined by genetic testing that is known to be a GoF variant as determined by functional characterization (established variant or determined).

Participants with GRIN-related neurodevelopmental disorder who have qualifying seizures will be enrolled in this cohort. Participants must have CMS (with or without neurodevelopmental symptoms) to be considered for enrollment. CMS includes the following seizure types: generalized tonic-clonic; clonic bilateral; tonic bilateral (with likely fall); atonic (with likely fall); focal to bilateral tonic-clonic; focal motor observable (intact, impaired or unknown awareness).

To be randomized, participants must have at least 1 CMS per week and ≥4 CMSs (generalized or focal) during a prospective ≥4-week Observation Period and also to have previously failed to obtain adequate seizure control with at least 2 ASMs. All inclusion and exclusion criteria are provided in the Study Entry Criteria Section for this cohort.

Each site will be required to complete a SIF for each participant. This information will be submitted to ESCI after the Screening Visit for review. The SIF will be used to ensure that the seizures are classified accurately. If a new seizure type occurs during the study that was not previously confirmed by ESCI, a past seizure type (from >1 year prior to screening) reoccurred, or a seizure type was inadvertently omitted, the site will be required to complete a new SIF and submit to ESCI for review and confirmation.

Forty participants that meet eligibility criteria will be randomized based on a 1:1 ratio to radiprodil and matching placebo. Randomization will be stratified by age: <2 years old, 2 to 12 years old, and >=13 years old. The number randomized may be adjusted based on the planned interim analysis which includes a sample size re-estimation. Additional details are provided in the Statistical Methods Section for this cohort.

This cohort consists of a Screening Period, a Titration Period, a Maintenance Period on the highest tolerated dose, and a Safety Follow-up Period (if not entering Part B-OLE Study). The duration of each period is provided in the Study Duration section.

Following completion of the Maintenance Period, eligible participants will undergo a transition titration (approximately 5 weeks) as part of Part B-OLE Study. The purpose of the transition titration is to maintain the blind for the Titration and Maintenance Periods of the Phase 3 cohorts.
Titration and Maintenance Dosing The following dose escalation regimen (twice a day, b.i.d.) will be used:

Starting dose: 0.125 mg/kg or matching placebo
Intermediate dose 1:0.25 mg/kg or matching placebo
Intermediate dose 2:0.5 mg/kg or matching placebo
Target dose: 0.75 mg/kg or matching placebo
Maximum dose: 1.0 mg/kg or matching placebo Study drug administration will start on Day 1 of Visit T1. Subsequent titration visits T2-5 may occur at the site or at home under the remote supervision of the investigator. During the Titration Period, participants will take their assigned titration dose level with 7 to 10 days between titration visits.

Titration visits will be conducted as per FIG. 7A-D with the goal to escalate participants to the target dose level by T4. If the participant is tolerating that dose level and the investigator believes there could be clinical benefit with a higher dose, the investigator may titrate up to the maximum dose level (1.0 mg/kg b.i.d.) at T5. The investigator should make every effort to escalate to and maintain patients at a dose level of at least 0.75 mg/kg b.i.d. However, if necessary for patient safety, the investigator may reduce the dose level to 0.5 mg/kg b.i.d. and notify the medical monitor of this change. If this dose level is not tolerated, the patient must discontinue study drug but is encouraged to remain in the study for safety monitoring.

After identification of an adequate and tolerated dose, participants will continue taking that dose throughout the Maintenance Period. Visit M1 will be scheduled 7 days (+3 days) after the last visit of the Titration Period. Maintenance visits will be conducted as per FIG. 7A-D. Blood samples for PK analysis will be obtained as scheduled in FIG. 12.
Safety Administration of study drug will be stopped for a participant who develops a medical condition (or laboratory abnormality or ECG change) that, in the opinion of the investigator, compromises the participant's ability to participate or compromises the participant's safety. The participant should be followed until the condition has resolved. Study drug may then be potentially restarted, as determined by the investigator in consultation with the sponsor's physician/medical monitor).

Any participant whose study drug is permanently discontinued will be encouraged to complete the study, including all relevant assessments. Participants withdrawing from the study will be encouraged to have at least the assessments scheduled for Visit M5 and the Safety Follow-up.

Additionally, an investigator may discontinue or withdraw a participant from the study for the following reasons: Decision by the investigator; Decision by the sponsor; Decision by regulatory authority; Caregiver/participant request; Change in compliance with any inclusion/exclusion criterion that is clinically relevant and affects the participant safety, as determined by the investigator, or the integrity of the study data; Protocol deviation that is considered to potentially compromise the safety of the participant or the integrity of the study data; Unacceptable noncompliance with any relevant study interventions or assessments; Any clinically relevant sign or symptom that in the opinion of the investigator warrants participant removal from study intervention; Disease progression that compromises the ability of the participant to safely continue in the study, with particular reference to any unexpected worsening of seizures or behavioral symptoms assessed as related to the study drug; Pregnancy.

Participants who are withdrawn for reasons unrelated to study drug (including coronavirus disease 2019 infection or restrictions) or withdrawn as a result of AEs thought to be related to study drug, as determined by the investigator, may be replaced.

The Data and Safety Monitoring Board (DSMB) will meet periodically as determined by rate of study recruitment to: review the data with a focus on safety and tolerability; assess the risk-benefit profile; consider other emerging safety issues; determine whether continuation of the study is appropriate, and oversee the planned interim analysis.

If a participant discontinues prematurely (i.e., before the last visit of the Maintenance Period Visit M5), the study drug will be tapered off, and an early termination visit will be conducted as soon as possible after the last full dose, with the procedures scheduled for Visit M5 and the Safety Follow up Visit if possible. Any participant whose study drug is permanently discontinued will be encouraged to complete the study, including all relevant assessments.

Participants who choose not to participate or are not eligible for Part B based upon entry criteria will taper off study drug and enter a 2-week Safety Follow up Period after the last dose.

Part A—Randomized Auxiliary Cohort of Participants without Qualifying Seziures

Participants with GRIN-related neurodevelopmental disorder who do not have qualifying seizures will be enrolled in this cohort. To be randomized, participants must experience significant neurodevelopmental symptoms based on caregiver report with a CGI-S score ≥4 at the Screening Visit and on Day −1. All inclusion and exclusion criteria are provided in the Study Entry Criteria Section for this cohort.

Each site will be required to complete a SIF for each participant. This information will be submitted to ESCI after the Screening Visit for review. If a participant in this cohort experiences seizures, the SIF will be used to ensure that the seizures are classified accurately. If a new seizure type occurs during the study that was not previously confirmed by ESCI, a past seizure type (from >1 year prior to screening) reoccurred, or a seizure type was inadvertently omitted, the site will be required to complete a new SIF and submit to ESCI for review and confirmation.

Up to 40 participants that meet eligibility criteria will be randomized based on a 1:1 ratio to radiprodil and matching placebo. Randomization will be stratified by age: <2 years old, 2 to 12 years old, and >=13 years old. It is planned to screen a sufficient number of participants with characterized GRIN1, GRIN2A, GRIN2B, or GRIN2D GoF variants. Additional details are provided in the Statistical Methods Section for this cohort. All other aspects of the design are identical to Part A—Phase 3 Randomized Qualifying Seizure Cohort. Titration Period assessments and timing are provided in FIG. 8A-C. Maintenance Period visits will be conducted as per FIG. 9A-B. Blood samples for PK analysis will be obtained as scheduled in FIG. 12.

Part B-Open Label Extension (OLE) Study

Following completion in Part A, eligible participants will begin the transition titration in Part B which mirrors the initial Titration Period in the number and timing of visits, assessments conducted, and dose titration procedure (FIG. 11A-B). The purpose of this transition titration is to maintain study blind while ensuring that participants previously receiving radiprodil remain at their tolerated dose, and those previously receiving placebo are titrated up to a tolerated dose of radiprodil. The safety, tolerability, and efficacy data collected at their last visit in Part A will be used as their Baseline data in Part B (collected within 7 days prior to Part B Day 1).

During the Maintenance Period of Part B, participants will continue to receive their previous established dose of radiprodil or dose determined in transition titration (for those participants who received placebo in the randomized cohorts) and should also plan to remain on their stable SOC for the study duration, which will be determined based upon an assessment of benefit-risk. However, adjustments to the SOC are permitted as determined by the investigator in consultation with the medical monitor.

Study drug administration will be stopped if a participant develops a medical condition (or laboratory abnormality or ECG change) that, in the opinion of the investigator or sponsor, compromises the participant's ability to participate or compromises the participant's safety. This may include occurrence of any SAE considered at least possibly related to study drug.

If a participant is not allowed to restart, study drug will be tapered off, and the participant will be encouraged to attend an early termination visit as soon as possible after the last dose. Patients should be encouraged to remain in the study for safety follow-up.

Participants will visit the site every 3 months, undergoing the assessments as detailed in FIG. 10A-C with the option for an overnight stay, dependent upon geography and convenience. Visits where V-EEG is not mandated may be conducted remotely (e.g., as telemedicine visits) in exceptional circumstances with approval of the medical monitor.

Electrocardiogram assessments and multichannel 8- to 24-hour V-EEG will be performed as detailed in FIG. 10A-C. The V-EEG results will be reviewed by an independent expert EEG reviewer. For visits including V-EEG evaluation, an overnight stay at the site or in suitable accommodation close to the site will be permitted—in accordance with—the investigator's evaluation of participant safety and the convenience of the participant and their caregivers.

Caregivers will continue to record the volume of study drug taken every day. Caregivers will also continue to record the number and type of seizures each day for the first year. The number, type, and severity of behavioral symptoms and other disorder features will be assessed using the ABC-C, Vineland-3 (participants from the Phase 3 cohorts only), CGI-C, CGI-S, and CaGI-C, as well as quality of life as measured by PedsQL.

Telephone calls will be conducted by the sites every month, except on the months with scheduled visits every 3 months, to assess caregivers' eDiary entries (seizure data, daily study drug volume, use of rescue medication for seizures, and data reported by the caregivers based on the integrated scales), any AEs, and changes to concomitant medications (including ASMs).

Unscheduled visits could be conducted as needed with the option to use telemedicine visit technology. The tests and assessments to be performed during an unscheduled visit will be the same as for the regular 3-monthly visits, except that in the case of a telemedicine visit, V-EEG and ECG are only as required to assess the participant's clinical status.

Participation in Part B will continue until one of the following occurs: the participant withdraws/is withdrawn from the study, study termination as determined by assessment of the benefit-risk of radiprodil for this indication, market access to radiprodil is available in the country where the participant lives, Study drug may be discontinued for reasons that may include (but are not limited to) unacceptable safety concerns/tolerability issues, apparent lack or loss of efficacy, participant/caregiver choice, or sponsor decision. Under these circumstances and following consultation with the study medical monitor, radiprodil treatment will be tapered off over a suitable period. If possible, an Early Termination Visit should occur prior to initiating the taper (see FIG. 10A-C). Participants should be encouraged to remain in the study for safety follow-up.

The long-term safety and tolerability of radiprodil will be assessed by evaluating AEs, SAEs, and ADRs (frequency, type, severity, and duration), together with changes in vital signs, physical examination findings, 12-lead ECG findings, clinically significant changes in laboratory parameters, suicidal ideation or behavior (for participants ≥6 years of age), seizure frequency, and emergence of new seizure types, if applicable. All AEs observed by the study personnel or reported by the participant or caregivers during the study (from the time of the signing of the informed consent, and assent if applicable, through the End-of-Study/Early Termination Visit) will be documented.

The maintenance of treatment effect will be assessed by analyzing the change in seizure frequency and severity (if applicable), including seizure-free days and longest period with no seizures. The changes from Baseline to end of treatment in behavioral features and motor function as measured by ABCC, Vineland-3 (participants from the Phase 3 cohorts only), CGI-C, CGI-S, and CaGI-C, as well as quality of life as measured by PedsQL will be assessed.

Example 6. Oral Suspension Pediatric Formulation

Qualitative and quantitative compositions for radiprodil granules at 1%, 10%, and 30% drug loading are described in Table 4.

TABLE 4

Qualitative and quantitative compositions for radiprodil granules at 1%, 10%, and 30% drug loading.

| Excipients | Function | 30% drug loading (% w/w) | 10% drug loading (% w/w) | 1% drug loading (% w/w) |
|---|---|---|---|---|
| Radiprodil Form A | Drug substance | 30.00 | 10.00 | 1.00 |
| Mannitol (Pearlitol 100 SD) | Co-filler | 48.00 | 64.00 | 71.00 |
| Microcrystalline cellulose (Avicel PH 101) | Filler | 12.00 | 16.00 | 18.00 |
| Crospovidone (Kollidon CL) | Disintegrant | 5.0 | 5.00 | 5.00 |
| Povidone (Kollidon 30) | Binder | 4.00 | 4.00 | 4.00 |
| Polysorbate 80 (Tween 80) | Surfactant | 1.00 | 1.00 | 1.00 |
| Total | | 100.00 | 100.00 | 100.00 |

CL = cross-linked; SD = spray-dried; % w/w = percentage weight for weight

As stated in Section 3.2.2, the 1% and 10% drug loading granules have a 36-month expiration dating period from date of manufacture when stored at room temperature (15-25° C.).

Stability testing for the 30% drug loading granules is on-going, but stability results to date give an acceptable usage period of at least 12 months from date of manufacture for the 30% drug loading granules when stored at room temperature (15-25° C.).

Radiprodil granules reconstituted in water/SyrSpend SF® PH4 10/90 in round amber glass bottles and stored up to 3 months at 5° C. or 25° C. have been evaluated in an ICH-compliant stability study. The collected stability data allow using the reconstituted oral suspension for all drug product granules (1%, 10%, and 30% drug loading) for multiple doses for up to 60 days when stored at room temperature (15-25° C.).

Based on the validation data results, gastric tube administration is proposed as acceptable for clinical participants over the dose range of 2 mL to 28 mL for the 1% constituted granules, 1 mL to 28 mL for the 10% constituted granules, and 1 mL to 9 mL for the 30% constituted granules.

Example 7. Food Effect Studies of Radiprodil

To identify radiprodil dose regimens to evaluate for the phase 3 study in patients with GRIN-related neurodevelopmental disorder (NDD), virtual populations were simulated. The goal of the simulations was to identify a radiprodil dose regimen that would keep the 97.5 percentile plasma radiprodil concentrations above a $C_{avg}$ of 100 ng/ml which is expected to be associated with at least 75% receptor occupancy but less than the exposure observed at the no observable adverse effect level (NOAEL) in a juvenile rat toxicology study ($C_{max}$=1404 ng/mL; $AUC_{tau}$=9550 ng*h/mL) which is the exposure threshold in an ongoing (Phase 1B) and planned (Phase 3) clinical study. In particular, this modeling was conducted to ensure $C_{max}$ levels were below the exposure limits, as the Sponsor considers $C_{max}$ levels more related to the seizure-related toxicological effects observed in preclinical studies.

To identify radiprodil doses to be studied in the Phase 3 clinical study described above, simulations were conducted utilizing the 30% formulation under fed and fasted conditions. In the simulations, all subjects were assumed to be representative of the targeted GRIN-related NDD population and were split as 50:50 male: female. In the model, subjects <6 months were based upon allometry as there was no experimental evidence of ontogeny (Johnson et al, 2021). Each cohort of N=500 was generated from: Four age groups (1 month to <2 years, 2y to 12, 12y to 18, >18y); One formulation (30% oral suspension), and Two prandial states (fed and fasted).

Radiprodil doses every 12 hours (Q12 hour dose regimens) were simulated to steady state as follows:

0.125 mg/kg for 1 week, 0.25 mg/kg for 1 week then 0.5 mg/kg for 3 weeks 0.125 mg/kg for 1 week, 0.25 mg/Kg for 1 week, 0.5 mg/kg for 1 week, then 0.75 mg/kg for 3 weeks 0.125 mg/kg for 1 week, 0.25 mg/kg for 1 week, 0.5 mg/kg for 1 week, 0.75 mg/kg for 1 week, then 1 mg/kg for 3 weeks Age/weight sampling sources were as follows:

Subjects <2 years were sampled with replacement from WHO database

Pediatric ≥2 years and adult subjects were sample with replacement from a CDC NHAES Survey database via PK-Sim software The predicted steady state exposures for radiprodil administered in the 30% formulation under fed or fasted conditions at 0.5 mg/kg, 0.75 mg/kg and 1 mg/kg Q12 hour are shown in Table 5, Table 6 and Table 7, respectively. The predicted % of subjects with radiprodil exposures above the $C_{avg}$ of 100 ng/ml and below the $C_{max}$ and $AUC_{24}$ hour exposures observed at the NOAEL in the juvenile rat toxicology study are shown in Table 8, Table 9 and Table 10, respectively.

TABLE 5

The Predicted Steady State Exposures of Radiprodil Administered in the 30% Formulation Under Fed or Fasted Conditions at the Dosing Regimen of 0.5 mg/kg Q12 hour

| | 1 m.o. to <2 y.o. | | 2 to 12 y.o. | |
|---|---|---|---|---|
| | Fasted (N = 500) | Fed (N = 500) | Fasted (N = 500) | Fed (N = 500) |
| Cmax (ng/mL) | | | | |
| Median (CV %) | 130 (20.2%) | 190 (19.9%) | 160 (19.2%) | 240 (20.1%) |
| [2.5, 97.5] percentile | [86, 190] | [130, 290] | [110, 230] | [160, 340] |
| Cmin (ng/mL) | | | | |
| Median (CV %) | 66 (36.7%) | 80 (43.2%) | 99 (37.4%) | 130 (37.1%) |
| [2.5, 97.5] percentile | [21, 110] | [23, 150] | [36, 180] | [40, 230] |
| Cavg (ng/mL) | | | | |
| Median (CV | 99 (18.5%) | 140 (19.5%) | 130 (21.9%) | 180 (20.8%) |
| [2.5, 97.5] percentile | [68, 140] | [93, 200] | [88, 200] | [120, 270] |
| AUC24 (ng/mL * hr) | | | | |
| Median (CV %) | 2300 (18.5%) | 3200 (19.5%) | 3100 (21.9%) | 4200 (20.8%) |
| [2.5, 97.5] percentile | [1600, 3200] | [2100, 4500] | [2000, 4600] | [2800, 6300] |

| | 13 to 17 y.o. | | Adults | |
|---|---|---|---|---|
| | Fasted (N = 500) | Fed (N = 500) | Fasted (N = 500) | Fed (N = 500) |
| Cmax (ng/mL) | | | | |
| Median (CV %) | 190 (18.2%) | 280 (16.9%) | 200 (19.2%) | 290 (18.8%) |
| [2.5, 97.5] percentile | [130, 260] | [200, 390] | [130, 290] | [210, 410] |
| Cmin (ng/mL) | | | | |
| Median (CV %) | 120 (30.7%) | 160 (32.1%) | 130 (32.2%) | 170 (33.6%) |
| [2.5, 97.5] percentile | [50, 200] | [68, 270] | [55, 210] | [69, 280] |
| Cavg (ng/mL) | | | | |
| Median (CV %) | 160 (18.7%) | 220 (17.3%) | 170 (19.6%) | 240 (19.8%) |
| [2.5, 97.5] percentile | [120, 230] | [160, 310] | [120, 240] | [160, 340] |
| AUC24 (ng/mL * hr) | | | | |
| Median (CV %) | 3700 (18.7%) | 5100 (17.3%) | 3900 (19.6%) | 5400 (19.8%) |
| [2.5, 97.5] percentile | [2700, 5300] | [3800, 7100] | [2600, 5600] | [3600, 7800] |

TABLE 6

| The Predicted Steady State Exposures of Radiprodil Administered in the 30% Formulation Under Fed or Fasted Conditions at the Dosing Regimen of 0.75 mg/kg Q12 hour | | | | |
|---|---|---|---|---|
| | 1 m.o. to <2 y.o. | | 2 to 12 y.o. | |
| | Fasted (N = 500) | Fed (N = 500) | Fasted (N = 500) | Fed (N = 500) |
| Cmax (ng/mL) | | | | |
| Median (CV %) | 190 (20.2%) | 290 (19.9%) | 240 (19.2%) | 360 (20.1%) |
| [2.5, 97.5] percentile | [130, 280] | [200, 430] | [170, 350] | [250, 510] |
| Cmin (ng/mL) | | | | |
| Median (CV %) | 99 (36.7%) | 120 (43.2%) | 150 (37.4%) | 190 (37.1%) |
| [2.5, 97.5] percentile | [31, 170] | [35, 230] | [54, 270] | [60, 340] |
| Cavg (ng/mL) | | | | |
| Median (CV %) | 150 (18.5%) | 210 (19.5%) | 200 (21.9%) | 280 (20.8%) |
| [2.5, 97.5] percentile | [100, 210] | [140, 290] | [130, 300] | [190, 410] |
| AUC24 (ng/mL * hr) | | | | |
| Median (CV %) | 3400 (18.5%) | 4800 (19.5%) | 4600 (21.9%) | 6300 (20.8%) |
| [2.5, 97.5] percentile | [2400, 4700] | [3200, 6800] | [3000, 6900] | [4300, 9400] |
| | 13 to 17 y.o. | | Adults | |
| | Fasted (N = 500) | Fed (N = 500) | Fasted (N = 500) | Fed (N = 500) |
| Cmax (ng/mL) | | | | |
| Median (CV %) | 280 (18.2%) | 420 (16.9%) | 300 (19.2%) | 430 (18.8%) |
| [2.5, 97.5] percentile | [200, 390] | [300, 580] | [200, 430] | [310, 620] |
| Cmin (ng/mL) | | | | |
| Median (CV %) | 180 (30.8%) | 240 (32.2%) | 190 (32.3%) | 260 (33.8%) |
| [2.5, 97.5] percentile | [75, 300] | [100, 400] | [82, 320] | [100, 420] |
| Cavg (ng/mL) | | | | |
| Median (CV %) | 240 (18.8%) | 330 (17.3%) | 250 (19.7%) | 350 (19.9%) |
| [2.5, 97.5] percentile | [170, 350] | [250, 460] | [170, 360] | [240, 510] |
| AUC24 (ng/mL * hr) | | | | |
| Median (CV %) | 5500 (18.8%) | 7700 (17.3%) | 5800 (19.7%) | 8100 (19.9%) |
| [2.5, 97.5] percentile | [4000, 8000] | [5600, 11000] | [4000, 8400] | [5500, 12000] |

TABLE 7

| The Predicted Steady State Exposures of Radiprodil Administered in the 30% Formulation under Fed or Fasted Conditions at the Dosing Regimen of 1 mg/kg Q12 hour | | | | |
|---|---|---|---|---|
| | 1 m.o. to <2 y.o. | | 2 to 12 y.o. | |
| | Fasted (N = 500) | Fed (N = 500) | Fasted (N = 500) | Fed (N = 500) |
| Cmax (ng/mL) | | | | |
| Median (CV %) | 260 (20.2%) | 380 (19.9%) | 320 (19.2%) | 480 (20.1%) |
| [2.5, 97.5] percentile | [170, 380] | [270, 570] | [220, 460] | [330, 680] |
| Cmin (ng/mL) | | | | |
| Median (CV %) | 130 (36.7%) | 160 (43.2%) | 200 (37.4%) | 250 (37.1%) |
| [2.5, 97.5] percentile | [42, 220] | [46, 300] | [72, 350] | [80, 450] |
| Cavg (ng/mL) | | | | |
| Median (CV %) | 200 (18.5%) | 280 (19.5%) | 270 (22.0%) | 370 (20.8%) |
| [2.5, 97.5] percentile | [140, 270] | [190, 390] | [180, 400] | [250, 550] |
| AUC24 (ng/mL * hr) | | | | |
| Median (CV %) | 4600 (18.5%) | 6300 (19.5%) | 6200 (22.0%) | 8500 (20.8%) |
| [2.5, 97.5] percentile | [3100, 6300] | [4300, 9000] | [4000, 9200] | [5700, 13000] |

TABLE 7-continued

The Predicted Steady State Exposures of Radiprodil Administered in the 30% Formulation under Fed or Fasted Conditions at the Dosing Regimen of 1 mg/kg Q12 hour

| | 13 to 17 y.o. | | Adults | |
|---|---|---|---|---|
| | Fasted (N = 500) | Fed (N = 500) | Fasted (N = 500) | Fed (N = 500) |
| Cmax (ng/mL) | | | | |
| Median (CV %) | 380 (18.2%) | 560 (16.9%) | 400 (19.2%) | 580 (18.8%) |
| [2.5, 97.5] percentile | [260, 520] | [400, 780] | [270, 570] | [410, 830] |
| Cmin (ng/mL) | | | | |
| Median (CV %) | 240 (30.8%) | 320 (32.2%) | 250 (32.4%) | 340 (33.8%) |
| [2.5, 97.5] percentile | [100, 400] | [140, 530] | [110, 430] | [140, 560] |
| Cavg (ng/mL) | | | | |
| Median (CV %) | 320 (18.8%) | 450 (17.3%) | 340 (19.7%) | 470 (20.0%) |
| [2.5, 97.5] percentile | [230, 460] | [330, 620] | [230, 480] | [320, 680] |
| AUC24 (ng/mL * hr) | | | | |
| Median (CV %) | 7400 (18.8%) | 10000 (17.3%) | 7800 (19.7%) | 11000 (20.0%) |
| [2.5, 97.5] percentile | [5300, 11000] | [7500, 14000] | [5300, 11000] | [7300, 16000] |

TABLE 8

The Percentage of Subjects with Radiprodil $C_{max}$ and $AUC_{24}$ under the NOAEL from the Rat Juvenile Toxicology Study and Radiprodil $C_{avg}$ above the RO Target Following Simulations of Radiprodil 0.5 mg/kg Q12 hour under Fasted/Fed Conditions with the 30% Formulation

| | 1 m.o. to <2 y.o. | | 2 to 12 y.o. | |
|---|---|---|---|---|
| | Fasted (N = 500) | Fed (N = 500) | Fasted (N = 500) | Fed (N = 500) |
| Cmax under NOAEL (1404 ng/mL) | | | | |
| Yes | 500 (100%) | 500 (100%) | 500 (100%) | 500 (100%) |
| No | 0 (0%) | 0 (0%) | 0 (0%) | 0 (0%) |
| AUC24 under NOAEL (9555 ng/mL * hr) | | | | |
| Yes | 500 (100%) | 500 (100%) | 500 (100%) | 500 (100%) |
| No | 0 (0%) | 0 (0%) | 0 (0%) | 0 (0%) |
| Cavg above RO target (100 ng/mL) | | | | |
| Yes | 244 (48.8%) | 475 (95.0%) | 445 (89.0%) | 500 (100%) |
| No | 256 (51.2%) | 25 (5.0%) | 55 (11.0%) | 0 (0%) |
| | **13 to 17 y.o.** | | **=18 y.o.** | |
| | Fasted (N = 500) | Fed (N = 500) | Fasted (N = 500) | Fed (N = 500) |
| Cmax under NOAEL (1404 ng/mL) | | | | |
| Yes | 500 (100%) | 500 (100%) | 500 (100%) | 500 (100%) |
| No | 0 (0%) | 0 (0%) | 0 (0%) | 0 (0%) |
| AUC24 under NOAEL (9555 ng/mL * hr) | | | | |
| Yes | 500 (100%) | 500 (100%) | 500 (100%) | 498 (99.6%) |
| No | 0 (0%) | 0 (0%) | 0 (0%) | 2 (0.4%) |
| Cavg above RO target (100 ng/mL) | | | | |
| Yes | 495 (99.0%) | 500 (100%) | 499 (99.8%) | 500 (100%) |
| No | 5 (1.0%) | 0 (0%) | 1 (0.2%) | 0 (0%) |

TABLE 9

The Percentage of Subjects with Radiprodil $C_{max}$ and $AUC_{24}$ under the NOAEL from the Rat Juvenile Toxicology study and Radiprodil Cavg above the RO Target Following Simulations of Radiprodil 0.75 mg/kg Q12 hour under Fasted/Fed Conditions with the 30% Formulation

| | 1 m.o. to <2 y.o. | | 2 to 12 y.o. | |
|---|---|---|---|---|
| | Fasted (N = 500) | Fed (N = 500) | Fasted (N = 500) | Fed (N = 500) |
| Cmax under NOAEL (1404 ng/mL) | | | | |
| Yes | 500 (100%) | 500 (100%) | 500 (100%) | 500 (100%) |
| No | 0 (0%) | 0 (0%) | 0 (0%) | 0 (0%) |
| AUC24 under NOAEL (9555 ng/mL * hr) | | | | |
| Yes | 500 (100%) | 500 (100%) | 499 (99.8%) | 490 (98.0%) |
| No | 0 (0%) | 0 (0%) | 1 (0.2%) | 10 (2.0%) |
| Cavg above RO target (100 ng/mL) | | | | |
| Yes | 488 (97.6%) | 500 (100%) | 500 (100%) | 500 (100%) |
| No | 12 (2.4%) | 0 (0%) | 0 (0%) | 0 (0%) |

| | 13 to 17 y.o. | | =18 y.o. | |
|---|---|---|---|---|
| | Fasted (N = 500) | Fed (N = 500) | Fasted (N = 500) | Fed (N = 500) |
| Cmax under NOAEL (1404 ng/mL) | | | | |
| Yes | 500 (100%) | 500 (100%) | 500 (100%) | 500 (100%) |
| No | 0 (0%) | 0 (0%) | 0 (0%) | 0 (0%) |
| AUC24 under NOAEL (9555 ng/mL * hr) | | | | |
| Yes | 499 (99.8%) | 446 (89.2%) | 498 (99.6%) | 401 (80.2%) |
| No | 1 (0.2%) | 54 (10.8%) | 2 (0.4%) | 99 (19.8%) |
| Cavg above RO target (100 ng/mL) | | | | |
| Yes | 500 (100%) | 500 (100%) | 500 (100%) | 500 (100%) |
| No | 0 (0%) | 0 (0%) | 0 (0%) | 0 (0%) |

TABLE 10

The Percentage of Subjects with Radiprodil $C_{max}$ and $AUC_{24}$ under the NOAEL from the Rat Juvenile Toxicology study and Radiprodil $C_{avg}$ above the RO Target Following Simulations of Radiprodil 0.75 mg/kg Q12 hour under Fasted/Fed Conditions with the 30% Formulation

| | 1 m.o. to <2 y.o. | | 2 to 12 y.o. | |
|---|---|---|---|---|
| | Fasted (N = 500) | Fed (N = 500) | Fasted (N = 500) | Fed (N = 500) |
| Cmax under NOAEL (1404 ng/mL) | | | | |
| Yes | 500 (100%) | 500 (100%) | 500 (100%) | 500 (100%) |
| No | 0 (0%) | 0 (0%) | 0 (0%) | 0 (0%) |
| AUC24 under NOAEL (9555 ng/mL * hr) | | | | |
| Yes | 500 (100%) | 493 (98.6%) | 492 (98.4%) | 354 (70.8%) |
| No | 0 (0%) | 7 (1.4%) | 8 (1.6%) | 146 (29.2%) |
| Cavg above RO target (100 ng/mL) | | | | |
| Yes | 500 (100%) | 500 (100%) | 500 (100%) | 500 (100%) |
| No | 0 (0%) | 0 (0%) | 0 (0%) | 0 (0%) |

| | 13 to 17 y.o. | | Adults | |
|---|---|---|---|---|
| | Fasted (N = 500) | Fasted (N = 500) | Fasted (N = 500) | Fasted (N = 500) |
| Cmax under NOAEL (1404 ng/mL) | | | | |
| Yes | 500 (100%) | 500 (100%) | 500 (100%) | 500 (100%) |
| No | 0 (0%) | 0 (0%) | 0 (0%) | 0 (0%) |

TABLE 10-continued

The Percentage of Subjects with Radiprodil $C_{max}$ and $AUC_{24}$ under the NOAEL from the Rat Juvenile Toxicology study and Radiprodil $C_{avg}$ above the RO Target Following Simulations of Radiprodil 0.75 mg/kg Q12 hour under Fasted/Fed Conditions with the 30% Formulation

| | | | | |
|---|---|---|---|---|
| AUC24 under NOAEL (9555 ng/mL * hr) | | | | |
| Yes | 455 (91.0%) | 170 (34.0%) | 426 (85.2%) | 146 (29.2%) |
| No | 45 (9.0%) | 330 (66.0%) | 74 (14.8%) | 354 (70.8%) |
| Cavg above RO target (100 ng/mL) | | | | |
| Yes | 500 (100%) | 500 (100%) | 500 (100%) | 500 (100%) |
| No | 0 (0%) | 0 (0%) | 0 (0%) | 0 (0%) |

Overall, systemic exposures were predicted to be higher when radiprodil (30% formulation) was given under fed versus fasted conditions. Radiprodil systemic exposures were also predicted to progressively increase when going from the younger to the older age groups. Under fed conditions, predicted median radiprodil $C_{avg}$, $C_{max}$, and $AUC_{24}$ exposures at the 0.5 mg/kg dose regimen ranged from 140 to 240 ng/mL, 190 to 290 ng/ml, and 3200 to 5400 ng*h/ml, respectively, over the four age groups. At the 0.75 mg/kg dose regimen under fed conditions median $C_{avg}$, $C_{max}$, and $AUC_{24}$ exposures ranged from 210 to 350 ng/mL, 290 to 430 ng/mL, and 4800 to 8100 ng/ml*h, respectively, over the four age groups. At the 1 mg/kg dose regimen under fed conditions median $C_{avg}$, $C_{max}$, and $AUC_{24}$ exposures ranged from 280 to 470 ng/ml, 380 to 580 ng/mL, and 6300 to 11000 ng/ml*h, respectively, over the four age groups.

The highest predicted $C_{max}$ and $AUC_{24}$ values (97.5 percentile) were 620 ng/mL and 12000 ng/ml*h at the 0.75 mg/kg for the adult (>18 years) age group.

The results demonstrated that under fed conditions with the 30% formulation radiprodil exposures were maintained above a $C_{avg}$ of 100 ng/ml for the 0.75 mg/kg and 1 mg/kg Q12 hour dosing regimens for all age groups (Table 8 and Table 9). At the 0.5 mg/kg Q12 hour dosing regimen, radiprodil fell below the 100 ng/ml $C_{avg}$ in only 5% of subjects (Table 7). These results support that the three dosing regimens, when given under fed conditions, are expected to reach the pre-defined target threshold, as defined in the phase 1B and phase 3 study, and support the potential to obtain antiseizure efficacy of radiprodil in all age groups.

Predicted $C_{max}$ exposures for all three dosing regimens (0.5 mg/kg, 0.75 mg/kg, 1 mg/kg) administered under fed conditions were below the $C_{max}$ (1404 ng/mL) at the NOAEL in the juvenile rat toxicology study. The predicted $AUC_{24}$ values for the 0.5 mg/kg Q12 hour regimen under fed conditions were under the threshold of 9555 ng/ml*h. The $AUC_{24}$ values for the 0.75 mg/kg Q12 hour regimen were predicted to be above the 9555 ng/mL*h threshold in only 10.8% of subjects in the 13-17 years of age range and 19.8% of adult subjects, while the $AUC_{24}$ results at the 1 mg/kg exceed the threshold of 9555 ng/ml*h in the majority of adult subjects.

Therefore, a dose of 1 mg/kg BID will not be utilized as part of the dose escalation scheme in the Phase 3 study and the 0.75 mg/kg represents the proposed top dose.

In summary, the population PK model was able to well describe the PK of radiprodil in adult and pediatric subjects for all age ranges planned to be studied in GRIN-related NDD. A target dose of 0.75 mg/kg Q12 hours when administered as the 30% formulation in the fed state is expected to achieve the exposures relevant for the targeted NR2B receptor occupancy (at least 75%). In the ongoing Phase 1B study, 7 out of 9 subjects treated with 0.783 mg/kg bid (age 1-12y), showed a predicted RO in the range of 65-85%.

Table 11 shows a comparison of pharmacokinetic parameters of Radiprodil between 45 mg Radiprodil (30% Formulation) fed and fasted (pharmacokinetic analysis set) from Phase 1 study of normal healthy human subjects.

TABLE 11

Comparison of Pharmacokinetic Parameters of Radiprodil between 45 mg Radiprodil (30% Formulation) Fed and Fasted (Pharmacokinetic Analysis Set) from Phase 1 study of normal healthy human subjects

| Pharmacokinetic Parameter | Formulation and Fed Status | Number of Observations | Geometric LSM | Geometric LSM Ratio (Fed/Fasted) | 90% CI of Geometric LSM Ratio |
|---|---|---|---|---|---|
| Radiprodil | | | | | |
| $C_{max}$ (ng/mL) | Fed | 18 | 211.08 | 259.6% | (228.8%, |
| | Fasted | 18 | 81.30 | | 294.6%) |
| $AUC_{last}$ | Fed | 18 | 2774.98 | 155.8% | (139.3%, |
| (h * ng/mL) | Fasted | 18 | 1781.04 | | 174.3%) |
| $AUC_{inf}$ | Fed | 18 | 2812.02 | 148.4% | (133.0%, |
| (h * ng/mL) | Fasted | 17 | 1894.73 | | 165.7%) |

Abbreviations: CI = Confidence interval; CL = Confidence limit; GLS = Geometric least square; LSM = Least square mean.

Example 8. A Clinical Study of Radiprodil in the Treatment of Drug-Resistant Seizures and Behavioral Symptoms Investigational Product (IP): Radiprodil. This example describes an open-label, multicenter, phase 1B/2A study in participants with TSC or FCD Type II.

Objectives and Endpoints

The primary objectives of this study are to determine the safety and tolerability of multiple individually titrated doses of radiprodil in TSC and FCD Type II patients and to determine the pharmacokinetics (PK) and plasma exposure of radiprodil. Endpoints of these primary objectives include: adverse events (AEs), serious adverse events (SAEs), and adverse drug reactions (ADRs) (frequency, type, severity, and duration) over the course of treatment (Part A and Part B); changes in vital signs; physical examination findings; 12-lead electrocardiogram (ECG) findings; clinically significant changes in laboratory parameters; occurrence of suicidal ideation or behavior; and plasma concentrations of radiprodil at predefined timepoints.

Additional objectives of this study are to evaluate initial signs of efficacy on frequency and severity of epileptic seizures in those participants with seizures and to evaluate initial signs of efficacy of radiprodil on additional central nervous system (CNS) features including behavior and quality of life. Endpoints of these additional objectives include: change from Baseline to end of the Maintenance Period (Day 84) in seizure frequency from daily seizure electronic diary (eDiary); change from Baseline to end of Part B in seizure frequency from daily seizure eDiary; percent change from Baseline to end of treatment (Part A and Part B) in video electroencephalogram (V-EEG) seizure burden (e.g., seizure type, severity, and frequency recorded during V-EEGs); number of seizure free days and longest period with no seizures from Baseline to end of treatment; and change from Baseline to end of treatment (Part A and Part B) in behavioral features as measured by the aberrant behavior checklist-community (ABC-C), as well as other disorder features as measured by quality of life (Pediatric Quality of Life Inventory [PedsQL]), Caregiver Burden Inventory (CBI), and global impression (Caregiver Global Impression of Change [CaGI-C]), and Clinical Global Impression of Change [CGI-C] scales).

Study Design

The study will consist of 2 parts; a dose escalation/maintenance part (Part A) to determine the safety, tolerability, and PK of multiple individually titrated doses of radiprodil, and a long-term follow-up period (Part B) to assess the treatment effect on seizures and behavioral symptoms. A safe and well tolerated dose after approximately 16 weeks of continuous treatment during Part A will be established, and initial signs of efficacy and changes in quality of life will be evaluated. The study will further evaluate the long-term safety and tolerability of radiprodil and assess the maintenance of the treatment effect during Part B.

Part A

Approximately 30 participants will be enrolled using a 2:1 ratio (20 with TSC; 10 with FCD Type II). The study will consist of the following periods:

- Screening Period: up to 6 weeks but not less than 4 weeks;
- Titration Period: estimated to be 4 weeks but the final duration will be determined by PK assessments;
- Maintenance Period: up to 12 weeks; and
- Safety Follow-Up Period: 2 weeks after last dose.

After signing the informed consent form (ICF) (consent by the caregivers and assent by the participants, as applicable and according to local regulatory requirements) at the Screening Visit, participants will enter the 4-week Titration Period. Identification of prevalent observable motor seizures will be determined for each participant with seizures. Caregivers will also record other, non-motor seizure types and possible seizure-related phenomena in the eDiary. Participants meeting all eligibility criteria on Day 0 (Baseline) will enter the Titration Period and be admitted to the site for Titration Visit 1 (T1). Participants will visit the site for a minimum of 1 day, with the potential for overnight stays of approximately 3 days (Visit T1±1 day); hospitalization could be extended at the Investigator's discretion in consultation with the medical monitor. Administration of the IP, radiprodil, orally or enterally bid, will start on Visit T1.

Participants will visit the site for each of the subsequent titration visits. An overnight stay (or hotel stay) before and after a site-based titration day is allowed as deemed necessary based on practical considerations and taking into account participant and caregiver preference. Participants will continue to receive radiprodil at home. During the Titration Period, participants will take their assigned dose for 7 to 14 days until a dose escalation may be performed at the next visit (Visits T2, T3, T4, and subsequent visits if applicable [$T^N$]), again subject to logistical/travel considerations.

During the Titration Period, adaptive criteria based on PBPK modelling will be used to determine the individual dose escalation. Dose escalation will be based on the safety/tolerability profile observed in each individual participant and their radiprodil plasma concentration as measured at the current dose level. Once an appropriate dose level has been identified and it was tolerated by the participant, and the participant has completed the Titration Period with approval of the SRC, they will continue to take this dose throughout the Maintenance Period. However, should tolerability issues emerge, the dose level may be reduced to improve tolerability and (if appropriate) returned to the established dose when tolerability improves again. Such adjustments are at the discretion of the Investigator but should be promptly recorded in the eDiary/eCRF to ensure appropriate IP supply management.

Maintenance Visit 1 (MV1, Day 0) will be scheduled 7 days (+2 days) after the last visit of the Titration Period.

During the Maintenance Period, participants will visit the site monthly. An on-site visit will also occur 2 weeks after MV1 (Maintenance day 14 [D14]). Participants will receive telephone calls from the site 2 weeks after each on-site visit to assess compliance with IP administration, any adverse events (AEs), and changes to concomitant medications. The assessments scheduled for the MV4 (D42) visit will also be performed at the site for participants who terminate the study early.

During the Titration and Maintenance Periods, participants or their caregivers will record the volume of IP administered on each treatment day in the eDiary. Participants or their caregivers will also enter the number and type of seizures on a daily basis, including other, nonmotor seizure types and possible seizure-related phenomena. At the Screening Visit, participants or their caregivers will be trained to identify, count, and report the participant's seizures and on the use of the eDiary. Seizures confirmed by EEG or V-EEG recording by the investigator will be determined for each participant and analyzed as a secondary outcome. The number, type, and severity of behavioral symptoms will be assessed using the ABC-C; other disorder features will be assessed by PedsQL, CBI, and CGI-C and participants or their caregivers will assess seizures, and overall condition using the CaGI-C.

Blood samples for PK will be obtained at Visits T1 (pre-dose and 1, 2, 4, 6, 8, 10, and 12 hours after the first dose, with the 12-hour sample taken immediately before the administration of the second dose), T2, T3, T4, and TN (predose and 1, 2, and 5 hours after the first dose), MV1 (DO), MV3 (D28), MV5 (D56) (predose), and MV7 (D84)/early termination (predose and 1, 2, and 5 hours after the first dose). The timepoints and frequency of sampling may be adjusted based on the SRC evaluation on the minimum data needed to protect participant safety and comfort and to fulfill the study objectives. The days on which participants will visit the site, participants will take their doses at the site in conjunction with the PK sampling schedule.

The radiprodil plasma concentrations measured at the visits during the Titration Period will be considered for dose escalations. After administration of the first radiprodil dose in all participants, a rapid assay of the PK levels will allow the verification of exposure to radiprodil against the projected levels. If necessary, dosing adjustments by the SRC may be made (using the Simcyp software) if the measured exposure parameters (Cmax and AUC) indicate that the measured exposure exceeds 80% (±5%) NR2B RO. The exact timing and frequency of PK sampling may also be adjusted by the SRC based on emerging PK data from the first participants.

The starting dose for each participant enrolled in the study is set at 0.05 mg/kg and is expected to have a theoretical NR2B occupancy of approximately 25%. The required dose increments will be determined based on individual PK plasma levels (both AUC and Cmax) collected at each visit during the Titration Period.

Based on the dedicated PBPK model, the increment will be a dose expected to give no more than a 2.5-fold higher plasma concentration. The decision to move on to the next dose level will be decided by the SRC, based on the observed PK data and the absence of clinically relevant safety and tolerability events, as determined by the escalation/stopping criteria described further below.

The highest dose to be given to each of the participants will be capped at radiprodil concentrations expected to achieve an approximately 80% (±5%) NR2B occupancy.

At the Screening Visit, each site will be required to complete a seizure identification form (SIF) for each participant to ensure that seizures are classified accurately. If a new seizure type occurs during the study that was not previously approved, a past seizure type (from >1 year prior to screening) reoccurred, or a seizure type was inadvertently omitted, the site will be required to complete a new SIF.

For V-EEG evaluation, PK sampling, and safety evaluations at Visits T1 and MV7 (D84), an overnight stay at the site or in suitable accommodation close to the site will be required for all participants. At Visits T2, T3, T4, and MV1 (DO), overnight stays will be permitted for site-based visits in accordance with the investigator's evaluation of participant safety and the convenience of the participant and their caregivers.

It is anticipated that 3 dose escalations beyond the starting dose of 0.05 mg/kg will occur for each participant during the Titration Period but may be more based on SRC recommendation as determined by the individual radiprodil plasma concentration, safety, and tolerability. If a participant does not tolerate the IP dose after an escalation, reductions are allowed. Re-escalation may be permitted once the AE has been remitted. Subsequent re-escalation is permitted at a later Titration Visit, if clinically indicated (additional Titration Visits may occur to accommodate such circumstances). All dose changes by the Investigator should be communicated and discussed with the medical monitor, if possible.

The SRC (the PK subject matter expert, and the sponsor's physician/medical monitor in consultation with the Principal Investigator or Sub-investigator) will meet prior to each dose escalation to discuss the PK data and clinical findings and to evaluate the appropriateness of the dosing schedule for each participant. The SRC will also meet after the last titration visit to evaluate the dose prior to entering the maintenance phase. Confirmation by the SRC will not be required prior to a re-escalation to a previously administered higher dose.

Safety and tolerability of radiprodil will be assessed by evaluating AEs and clinically significant findings in vital signs, physical examinations, 12-lead electrocardiograms (ECGs), laboratory parameters, suicidal ideation or behavior, seizure frequency, and severity. All AEs observed by the study personnel or reported by the participant during the study (from the time of the signing of the informed consent, and assent if applicable, through the End-of-Study/Early Termination Visit) will be documented.

Plasma concentrations of radiprodil obtained at different doses and its major metabolites obtained during the Maintenance Period.

Efficacy will be assessed by analyzing the change from Baseline to end of treatment in motor seizure frequency from both daily seizure eDiary and V-EEG seizure burden (e.g., seizure type, severity, and frequency recorded during EEGs at Visits T1 and MV7 [D84]), the number of seizure-free days, and the longest period with no seizures. Furthermore, the changes from Baseline to end of treatment in behavioral and motor features as measured by ABC-C will be analyzed.

Overall clinical status and quality of life will be evaluated using CBI, CGI-C, CaGI-C(focusing on seizures, behavioral symptoms, and overall condition), and Peds-QL at all appropriate visits.

Dosing across the study will be suspended and an urgent SRC review will also occur within 24 hours if either of the following study stopping criteria are met:

- Any SAEs considered at least possibly related to the IP (as judged by investigator) in 2 or more participants, where those SAEs occur in the same body system; or
- Any severe nonserious adverse reaction (i.e., severe nonserious AEs considered at least possibly related to the IP as judged by investigator) in 3 or more participants, where those severe AEs occur in the same body system and lead to the discontinuation of IP of the affected participant.

At this urgent review, the SRC will confirm whether the above criteria have been met and, if so, whether cessation of dosing of all participants within the study should be temporary or permanent.

Thereafter, the Data Safety Monitoring Board (DSMB) (which will include independent external members) will need to approve any subsequent resumption of dosing and whether any amendments to the study are needed to support this. The DSMB will, in any case, meet regularly to review the data with a focus on safety and tolerability, to assess the risk benefit profile or as required to consider other emerging safety issues, and to determine whether continuation of the study is appropriate.

All participants will be encouraged to remain on their stable standard of care (SOC) for the duration of the study. However, adjustments to SOC are permitted as determined by the investigator and must be captured within the electronic case report form (eCRF).

If a participant discontinues prematurely (i.e., before the last visit of the Maintenance Period, MV7, D84), the IP will be tapered off, and an Early Termination Visit will be conducted as soon as possible after the last full dose with the procedures scheduled for MV7 (D84) and the Safety Follow-up Visit if possible.

Participants can be rescreened only once in exceptional cases at the discretion of the Investigator and with approval from the medical monitor.

The dosing schedule is detailed in Table 12.

TABLE 12

| Dosing schedule of participants | | | | | | | |
|---|---|---|---|---|---|---|---|
| Schedule | | Study Day | Proceeds at Dose 1 | Proceeds at Dose 2 | Proceeds at Dose 3 | Proceeds at Dose 4 | Proceeds at Dose N |
| Titration | T1 | t1 | 0.05 | 0.05 | 0.05 | 0.05 | 0.05 |
| | T2 | T1 + 7 (+7) | 0.05 | Dose 2 | Dose 2 | Dose 2 | Dose 2 |
| | T3 | T2 + 7 (+7) | — | Dose 2 | Dose 3 | Dose 3 | Dose 3 |
| | T4 | T3 + 7 (+7) | — | — | Dose 3 | Dose 4 | X |
| | MV1 | D0 ± 2 | 0.05 | Dose 2 | Dose 3 | Dose 4 | Dose N |
| | MV2 | D14 ± 2 | 0.05 | Dose 2 | Dose 3 | Dose 4 | Dose N |
| | MV3 | D28 ± 2 | 0.05 | Dose 2 | Dose 3 | Dose 4 | Dose N |
| | MV4 | D42 ± 2 | 0.05 | Dose 2 | Dose 3 | Dose 4 | Dose N |
| | MV5 | D56 ± 2 | 0.05 | Dose 2 | Dose 3 | Dose 4 | Dose N |
| | MV6 | D70 ± 2 | 0.05 | Dose 2 | Dose 3 | Dose 4 | Dose N |
| | MV7 | D84 ± 2 | 0.05 | Dose 2 | Dose 3 | Dose 4 | Dose N |

Abbreviations: D = Maintenance Period study day; MV = Maintenance Period visit; PK = pharmacokinetics; t = Titration Period study day; T = Titration Period; End-of-Titration Visit = M1.

Part B

During the Treatment Period of Part B, participants will continue to receive their previously established dose of radiprodil.

The Baseline Visit of Part B should be scheduled on the same day as the last visit of Part A. If deemed eligible at the Baseline Visit (Day 1 of Part B), participants will directly roll over from Part A and then continue to receive their established dose of radiprodil at home during the Long-term Treatment Period of Part B. The safety, tolerability, efficacy, and PK evaluations performed at the last visit of Part A will be carried forward and used as baseline evaluations for Part B if the data were collected within 7 days prior to Day 1 of Part B.

Administration of the IP will be stopped in any individual participant who develops a medical condition (or laboratory abnormality or ECG change) that, in the opinion of the Investigator or sponsor, compromises the participant's ability to participate or compromises the participant's safety. This may include occurrence of any SAE considered at least possibly related to the IP.

If a participant is not allowed to restart the IP, radiprodil will be tapered off, and the participant will be encouraged to attend an Early Termination visit as soon as possible after the last full dose.

Participants will visit the site every 3 months, undergoing assessments with the option for an overnight stay, dependent upon geography and convenience. These visits could be conducted remotely (e.g., as telemedicine visits) in exceptional circumstances with approval of the medical monitor.

Electrocardiogram assessments will be conducted every 3 months. Multichannel 8- to 24-hour V-EEG will be performed every 6 months. The V-EEG results will be reviewed by the investigator and an independent expert EEG reviewer. For visits including V-EEG evaluation, an overnight stay at the site or in suitable accommodation close to the site will be permitted in accordance with the Investigator's evaluation of participant safety and the convenience of the participant and their caregivers.

During Part B, if the Principal Investigator believes that it is in the best interest of the participant to change the dose (e.g., tolerability issues), this change should be first discussed with the medical monitor and sponsor. However, frequent adjustments are discouraged and should be discussed with the sponsor's physician/medical monitor. Dose adjustments should be promptly recorded in the eDiary and eCRF to ensure appropriate IP supply management.

During the Treatment Period of Part B, the volume of IP taken every day will continue to be recorded. Participants or their caregivers will also continue to record the number and type of seizures on a daily basis. The number, type, and severity of behavioral symptoms and other disorder features will be assessed using the ABC-C, CBI, CGI-C, CGI-S, and CaGI-C, as well as quality of life as measured by PedsQL.

Predose blood samples for trough PK analyses will be obtained every 3 months.

Telephone calls will be conducted by the sites every month, except on months with scheduled on-site visits (every 3 months), to assess participants or their caregivers' eDiary entries (seizure data, daily IP administration volume, participant's usual or prescribed regimen and frequency of rescue therapy for seizures, and data reported by the caregivers based on the integrated scales), any AEs, and changes to concomitant medications.

Unscheduled visits could be conducted as needed with the option to use telemedicine visit technology. The tests and assessments to be performed during an unscheduled visit will be the same as for the regular 3-monthly visits, except that V-EEG, ECG, and completion of the scales are optional.

Participation in Part B of the study will continue for 1 year but may be extended based on a favorable benefit/risk profile. At the end of the study, participants will taper off the IP and attend an End-of-Study Visit approximately 14 days after the last dose.

Each participant may be withdrawn from the study for reasons that may include (but are not limited to) unacceptable safety concerns/tolerability issues, apparent lack or loss of efficacy, participant/caregiver choice, or sponsor decision. Under these circumstances and following consultation with the study medical monitor, radiprodil treatment will be tapered off over a suitable period. Any participant who discontinues the study before the study is ended will be encouraged to attend an Early Termination Visit as soon as possible after the last full dose with the same assessments as scheduled for the End of Study Visit. The reason for participant discontinuation or withdrawal from the study will be recorded in the appropriate eCRF.

The long-term safety and tolerability of radiprodil will be assessed by evaluating AEs, SAEs, and ADRs (frequency, type, severity, and duration), together with changes in vital signs, physical examination findings, 12-lead ECG findings, clinically significant changes in laboratory parameters, suicidal ideation or behavior for participants ≥6 years of age, seizure frequency, or severity. All AEs observed by the study personnel or reported by the participant or caregivers during the study (from the time of the signing of the informed consent, and assent if applicable, through the End-of-Study/Early Termination Visit) will be documented.

The maintenance of the treatment effect will be assessed by analyzing the change in seizure frequency and severity (if applicable), including seizure-free days and longest period with no seizures. Overall clinical status and quality of life will be evaluated using CBI, CGI-C, CaGI-C(focusing on seizures, behavioral symptoms, and overall condition), and Peds-QL at all appropriate visits.

Trough plasma concentrations of radiprodil and its major metabolites will also be analyzed at selected timepoints.

Tapering Recommendation

If a participant is stopping the IP for any reason, they should undergo a tapering regimen reflecting the following recommended schedule, namely—the dose of radiprodil should be reduced by 25% of the full dose for each of three 5-day steps, i.e., to 75%, 50%, and then 25% before stopping entirely. However, this schedule may be modified at the discretion of the Investigator to suit the clinical circumstances, e.g., if a participant is already taking a low dose.

Preclinical Efficacy and NR2B Receptor Occupancy

In vivo preclinical data have indicated that radiprodil anticonvulsant effects correlate with plasma concentration and NR2B RO. Therefore, this relationship will guide the definition of the expected therapeutic range.

Radiprodil anticonvulsant efficacy was specifically tested in rats at different time points during postnatal development, using pentylenetetrazole (PTZ) as a convulsant, to induce generalized clonic-tonic seizures. The activity of radiprodil in this juvenile PTZ rat model was tested up to 30 mg/kg, showing efficacy at a dose of 1 mg/kg. The calculated free plasma fraction of an orally administered 1 mg/kg dose is expected to give around 60% occupancy of the NR2B receptor, based on an ex-vivo occupancy study in rodents and assuming a 1:1 brain to plasma ratio, see below for further details. At a dose of 10 mg/kg, roughly corresponding to 90% NR2B occupancy, radiprodil completely blocked the tonic phases of PTZ-induced convulsions in postnatal day 12 and postnatal day 18 rats. The anticonvulsant efficacy of radiprodil was also assessed in an audiogenic seizure model (generalized seizures) in adult mice, showing anticonvulsant activity in the same range of doses/exposures.

Although the in vivo efficacy models used so far to evaluate the anticonvulsant effects of radiprodil are not specific TCS- and FCD-related disorders, the data suggest that such effects correlate with NR2B occupancy.

Starting Dose

The starting dose for each participant enrolled in the study will be set at 0.05 mg/kg bid. This dose is expected to have a theoretical NR2B occupancy of approximately 25% and is felt to be an appropriate starting dose because of the following reasons:

- The associated exposure level is more than 20-fold lower (in terms of total $C_{max}$ and AUC) than the NOAEL exposure in the completed juvenile rat toxicology study (100 mg/kg/day);
- It has already been administered to 3 infants for treatment of resistant infantile spasms, in whom radiprodil treatment for up to 34 days was found to be safe and well tolerated (Auvin, 2020). In this previous study in infants, 2 participants received doses up to 0.2 mg/kg bid, and plasma exposure both in terms of Cmax (up to 208 ng/ml), and AUCO-t (up to 1036 ng× h/mL) increased in a linear fashion as expected, based on the PBPK modeling; or.
- It is well below the exposure levels associated with the safe and well tolerated single and multiple doses in adult healthy volunteers. In patients with neuropathic pain, a total daily dose of 135 mg (45 mg tid) up to 14 weeks has been previously administered. The plasma exposures corresponded to a $C_{max}$ of 482±129 ng/mL and an $AUC_{0-24}$ h of 6875 ng× h/mL. 7.3.1.7.

Dose Escalation

During the Titration Period, adaptive criteria based on PBPK modelling will be used to determine the individual dose escalation. Individualized predictions including mean and 5th and 95th percentiles will be performed for the first day(s) of low dose therapy, and measured concentration-time data will be superimposed. A decision tree will then be followed regarding the dose escalation strategy based on observed plasma concentrations in relation to predicted values and dose changes necessary to give the required RO; each dose increase will be contingent on review of the measured concentration-time data for the previous dose. Approximately 3 dose escalations beyond the starting dose level of 0.05 mg/kg are expected to be made during the Titration Period. Dose escalation will be based on the safety/tolerability profile observed in each individual participant, and their radiprodil plasma concentration as measured at the current dose level.

At the second and subsequent Titration Visits, the SRC will meet prior to dose escalation to decide whether to proceed to the next dose level and (if so) the increment to be adopted, based on the following criteria:

- The previous dose was sufficiently well tolerated to suggest that the next planned dose has a reasonable likelihood of being acceptably tolerable (i.e., if an AE that is likely to be closely correlated to dose level occurred with moderate or severe intensity at the previous dose, then any further escalation should be minimal, or should not occur);
- The next dose will be expected to give no more than a 2.5-fold higher plasma concentration according to the PBPK model;
- The next dose is predicted not to exceed the exposure anticipated to produce an approximately 80% (±5%) NR2B receptor occupancy;
- The next dose is predicted to be below the plasma exposure at the NOAEL plasma concentration observed in the 4-week juvenile rat study (i.e., a $C_{max}$ of 1404 ng/ml and $AUC_{0-24}$ h of 9,555 ng× h/mL); and
- The next dose will not exceed: 2 mg/kg bid (4 mg/kg daily) for participants <33 kg (participants weighing ±33 kg will be restricted to the 135 mg/day limit).

Those subjects who according to the PBPK model are in the lower end of radiprodil absorption, can be administered a dose that exceeds the total daily dose limit of 4 mg/kg. The recommended dose has to be below the projected exposure of the described PK study limit, and approved by the SRC.

Based on these criteria, the top exposure limit is currently perceived to be close to the highest acceptable benefit-risk ratio.

If a participant does not tolerate the IP after a dose escalation, a dose reduction is allowed. All dose changes by the investigator during the Titration Period should be communicated and discussed with the medical monitor first, provided that the safety of the participant allows. If tolerability improves sufficiently to permit consideration of a return to the previous higher dose level, this can be implemented at the discretion of the investigator, again following discussion with the medical monitor. In general, however, if participant safety permits, any other deviations from the planned dosing schedule should be approved by the SRC before implementation. It is to be noted that such additional titration steps may extend the duration of the participant's Titration Period and overall study participation.

Inclusion Criteria

A participant will be eligible for study participation if they meet all of the following criteria:

- Age range: –population ≥6 months up to 18 years at Part A baseline;
- Failed to respond to at least 2 anti-seizure medications (ASMs) at appropriate dosages and duration;
- Disease specific criteria: a. diagnosis of FCD Type II based on clinical symptoms and confirmed by a positive magnetic resonance imaging (MRI) b. diagnosis of TSC by either clinical or genetic diagnostic criteria (Northrup, 2021) as documented in the participant's medical record;
- Participant on average has had at least 8 countable/witnessed primary seizures during a 4 week baseline period with at least 1 seizure occurring in at least 3 of the 4 weeks of baseline;
- All medical interventions for epilepsy/behavior (including ketogenic diet and any neurostimulation devices) should be stable for 28 days prior to screening with no more than 6 days per month use of rescue medication. Participants must remain stable regimen throughout the treatment period;
- Participant's or their caregivers have signed informed consent and participant has signed assent (if applicable);
- Participant's or their caregivers are willing and able to complete entries in the eDiary on a daily basis;
- Participant has had a magnetic resonance imaging (MRI) scan within 12 weeks of Screening or during the Screening Period; and
- Participant is 1 of the following:
  - Not of childbearing potential (premenarchal or male/not in possession of a uterus);
  - If of childbearing potential, is nonpregnant (negative serum pregnancy test results at Screening and negative urine pregnancy test results at baseline), nonlactating, and practicing 1 of the following medically acceptable methods of birth control:
    - Abstinence as a lifestyle choice;
    - Hormonal methods such as oral, implantable, injectable, or transdermal contraceptives for a minimum of 1 full cycle (based on the participant's usual menstrual cycle period) before IP administration; or
    - Intrauterine device; or
  - If male, is willing to use a highly effective method of contraception throughout the study period.

Exclusion Criteria

A participant will be excluded from the study if they meet any of the following criteria:

- Participant with any other clinically relevant medical, neurologic, or psychiatric condition and/or behavioral disorder unrelated to TSC or FCD Type II that would preclude or jeopardize participant's safe participation or administration of study drug or the conduct of the study according to the judgement of the investigator;
- Participant with any clinically significant laboratory or ECG abnormalities that according to the Investigator in consultation with the Sponsor would jeopardize the safety of the participant, limit participation, or compromise the interpretation of the safety data from the participant;
- Participant has severe hepatic dysfunction (Child-Pugh grade C);
- Participant has a history of brain surgery for epilepsy or any other reason;
- Participant with any contraindications to radiprodil or with known hypersensitivity to the active substance or the excipients or other chemically closely related substances;
- Participant receiving treatment with contraindicated concomitant drugs such as agonists or antagonists of the glutamate receptor, including but not limited to felbamate, memantine, and perampanel; or
- Participant has received an investigational treatment within 3 months or 5 half-lives, whichever is longer.

Premature Participant Withdrawal

All participants will be advised that they are free to withdraw from participation in this study at any time, for any reason, and without prejudice. The investigator should make every reasonable attempt to keep participants in the study. However, participants must be withdrawn from the study if they withdraw consent to participate. Investigators must attempt to contact participants who fail to attend scheduled visits by telephone or other means to exclude the possibility of an AE being the cause of withdrawal. Should this be the cause, the AE must be documented and reported.

The sponsor reserves the right to request the withdrawal of a participant due to protocol deviations or other reasons.

The investigator also has the right to withdraw participants from the study at any time for lack of therapeutic effect that is intolerable or otherwise unacceptable to the participant, for intolerable or unacceptable AEs, intercurrent illness, noncompliance with study procedures, administrative reasons, or in the investigator's opinion, to protect the participant's best interest.

If a participant is withdrawn before completing the study, the reason for withdrawal and the date of discontinuation will be recorded on the appropriate page of the eCRF. Whenever possible and reasonable, the evaluations that were to be conducted at Visit M20 and the Safety Follow-up Visit should be performed at the time of premature discontinuation.

Discontinuation of Study Intervention

Discontinuation from the IP does not mean discontinuation from the study, and remaining study procedures should be completed as indicated by the study protocol. If a clinically significant finding is identified (including, but not limited to, changes from Baseline) after enrollment, the investigator or qualified designee will determine if any change in participant management is needed. Any new clinically relevant finding will be reported as an AE.

Administration of the IP will be stopped if the participant develops a medical condition (or laboratory abnormality or ECG change) that, in the opinion of the investigator, compromises the participant's ability to participate or compromises the participant's safety. This will include occurrence of any SAE considered at least possibly related to study treatment.

If any of the above circumstances occur, the participant should be followed until the condition has resolved, as agreed by the investigator and the sponsor's physician/medical monitor. If a participant discontinues the IP, restarting may be allowed, but only after review and approval by the SRC. The data to be collected at the time of study intervention discontinuation will include the following: A PK sample (ideally at trough) and safety laboratory panels.

Participant Discontinuation/Withdrawal from the Study

Participants are free to withdraw from participation in the study at any time upon request. Any participant whose dosing is permanently discontinued will taper off the IP and will be encouraged to complete the study or have at least the assessments scheduled for Visit 7 (md84) of the Maintenance Period and the Safety Follow-up Visit if possible.

Dosing across the study will be suspended if any of the general stopping criteria described herein. This decision will be made by the SRC and fully documented. Dosing may only be resumed with the agreement of the DSMB.

Additionally, an investigator may discontinue or withdraw a participant from the study for the following reasons:

Decision by the investigator;

Decision by the sponsor;

Decision by regulatory authority;

Caregiver/participant request;

Change in compliance with any inclusion/exclusion criterion that is clinically relevant and affects the participant safety, as determined by the investigator, or the integrity of the study data;

Protocol deviation that is considered to potentially compromise the safety of the participant or the integrity of the study data;

Unacceptable noncompliance with any relevant study interventions or assessments;

Any clinically relevant sign or symptom that in the opinion of the investigator warrants participant removal from study intervention;

Disease progression that compromises the ability of the participant to safely continue in the study, with particular reference to any unexpected worsening of seizures or behavioral symptoms assessed as related to the IP; or Pregnancy.

Participants who are withdrawn for non-IP related reasons (including coronavirus disease 2019 infection or restrictions) may be replaced following discussion between the investigator and the sponsor and a decision by the SRC. Participants withdrawn as a result of AEs thought to be related to the IP, as determined by the investigator, may also be replaced if study stopping rules have not been triggered. The decision regarding the replacement of participants will be made by the SRC and fully documented. The reason for participant discontinuation or withdrawal from the study will be recorded on the appropriate eCRF.

Participants whose caregivers sign an ICF but do not receive the IP may be replaced. Participants whose caregivers sign the ICF, receive the IP, and subsequently withdraw or are withdrawn or discontinued from the study, may be replaced, depending upon whether they have provided sufficient data to support the objectives of the study-which will be determined by the SRC.

A participant will be considered lost to follow-up if they fail to return for scheduled visits and is unable to be contacted by the study site staff. The following actions must be taken if a participant fails to return to the clinic for a required study visit:

The site will attempt to contact the participant and reschedule the missed visit and counsel the caregivers on the importance of maintaining the assigned visit schedule and ascertain if the participant wishes to and/or should continue in the study;

Before a participant is deemed lost to follow-up, the investigator or designee will make every effort to regain contact with the caregivers (where possible, 3 telephone calls and, if necessary, a certified letter to the participant's caregivers' last known mailing address or local equivalent methods). These contact attempts should be documented in the participant's medical record or study file; and Should the participant's caregivers continue to be unreachable, they will be considered to have withdrawn from the study with a primary reason of lost to follow-up.

Participant Replacement Criteria

Participants who are withdrawn from the study may be replaced in accordance with the criteria described herein. If a substantial number of participants are withdrawn from the study, the sponsor will evaluate the need for developing replacement criteria. Enrolled participants withdrawn from the study may not reenter. The participant number for a withdrawn participant will not be reassigned to another participant.

Study Stopping Criteria

An urgent SRC review will also occur within 24 hours if either of the following study stopping criteria are met:

Any SAEs considered at least possibly related to the IP (as judged by investigator) in 2 or more participants, where those SAEs occur in the same body system; or Any severe nonserious adverse reaction (i.e., severe nonserious AEs considered at least possibly related to the IP as judged by investigator) in 3 or more participants, where those severe AEs occur in the same body system and lead to the withdrawal of the affected participant.

At this urgent review, the SRC will confirm whether the above criteria have been met and, if so, whether cessation of dosing of all participants within the study should be temporary or permanent.

Thereafter, the DSMB (which will include independent external members) will need to approve any subsequent resumption of dosing and whether any amendments to the study are needed to support this. The DSMB will meet regularly throughout the study to review the data with a focus on safety and tolerability, to assess the risk benefit profile or as required to consider other emerging safety issues, and to determine whether continuation of the study is appropriate.

The decision of the DSMB on the need for cessation will take into account the risk/benefit evaluation for each participant and the potential for harm from the sudden withdrawal of a neuroactive medication in this population. Whatever the decision of the DSMB, it will be submitted to the local health authority and ethics committee as soon as possible within 7 days for their review.

Other stopping rules that will result in temporary hold or termination of the study:

The sponsor decides to terminate the study and no further dosing is scheduled; or A health authority or ethics committee requests a hold on dosing or study termination.

Example 9. Results from a Clinical Study of Radiprodil in the Treatment of Drug-Resistant Seizures and Behavioral Symptoms Results from an open-label, multicenter phase 1B study, as described in the previous Example, are described below.

A behavioral cohort of patients from 6 months to 12 years of age with known GoF variants confirmed via method described in Myers, et al., Hum Mol Genetics. 2023, 32:2857-2871, was enrolled. The patient had behavioral symptoms (CGI-S ≥4) but did not have ≥1 weekly countable motor seizure (CMS) with ≥4 generalized or focal seizures during the observation period. Motor seizures included drop seizures; generalized onset seizures included tonic-clonic, tonic, bilateral clonic, atonic, myoclonic-atonic, and myoclonic-tonic-clonic seizures; and focal seizures included seizures with bilateral hyperkinetic motor features and clonic seizures.

Figure 13:
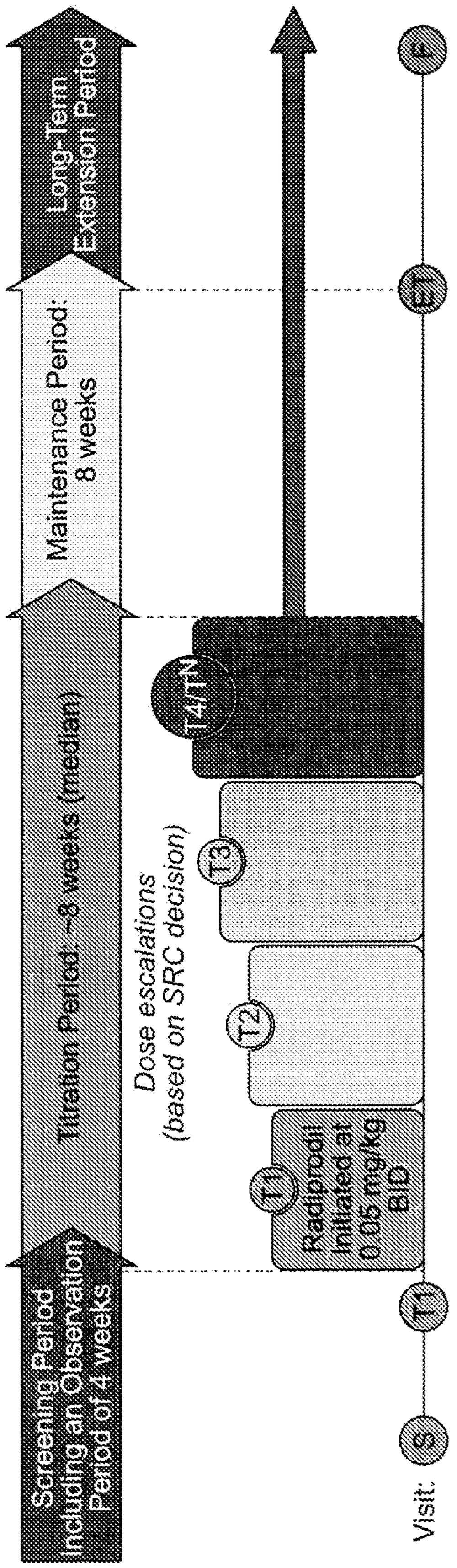
FIG. 13 illustrated the study design of a phase 1B study of radiprodil, as described in Example 9 below.

Study Design: Radiprodil was initiated at 0.05 mg/kg twice daily (BID) and incrementally increased based on the observed exposure determined by a dedicated physiologically based pharmacokinetic model, predicted receptor occupancy, and safety, and tolerability as assessed by the safety review committee (SRC), as shown in FIG. 13.

Part A: ≤5-week screening period, an individualized dose escalation phase, and an 8-week maintenance period.

Part B: Assessment of the long-term safety of radiprodil.

Radiprodil doses during the Maintenance Period ranged from 0.25 to 1.96 mg/kg (median: 0.783 mg/kg) administered BID orally or by feeding tube.

The range of the titration period was 5.1 to 21.6 weeks (median: 8.5 weeks)

Results: Baseline demographic and disease characteristics were generally balanced between cohorts and representative of the target population. A predefined data cut was performed when 12 patients completed Part A.

TABLE 13

| Baseline demographic and disease characteristics | |
|---|---|
| Baseline Characteristics | Behavioural Cohort (n = 7) |
| Age, years, mean (SD) | 7.1 (3.8) |
| Sex, n (%) | |
| Female | 5 (71.4) |
| GRIN Type, n (%) | |
| GRIN1 GoF | 3 (42.9) |
| GRIN2A GoF | 1 (14.3) |
| GRIN2B GoF | 3 (42.9) |
| Baseline 28-day CMS frequency, median (min, max)[a] | — |
| Clinical Global Impression-Severity, n (%) | |
| Most extremely ill (7) | 1 (14.3) |
| Severely ill (6) | 4 (57.1) |
| Markedly ill (5) | 2 (28.6) |
| Number of Concomitant ASMs[b], mean (SD) | 1.5 (0.7) |

ASM, antiseizure medication.

[a]28-day seizure frequency is calculated as: (No. of seizures)/(No. of days seizures were assessed) x 28 days.

[b]Antiseizure medications are defined as medications with World Health Organization Anatomical Therapeutic Chemical Classification System level 2 of N03.

Treatment emergent adverse event (TEAE): Radiprodil treatment appeared to be generally well-tolerated. Pyrexia, diarrhoea, and respiratory tract infection were the most common TEAEs. Three patients experienced SAEs, all unrelated to radiprodil treatment. One each of adenovirus infection, bronchiolitis, and viral pneumonia.

TABLE 14

| Treatment emergent adverse event (TEAE) | |
|---|---|
| TEAEs, n (%)[a] | Behavioral Cohort (n = 7) |
| Any TEAE | 6 (85.7) |
| Pyrexia | 1 (14.3) |
| Diarrhea | 2 (28.6) |
| Respiratory tract infection | 2 (28.6) |
| Abnormal behavior | 2 (28.6) |
| Agitation | 2 (28.6) |
| Cough | 1 (14.3) |
| Dystonia | 1 (14.3) |
| Fatigue | 2 (28.6) |
| Gastroenteritis | 1 (14.3) |

Figure 14:
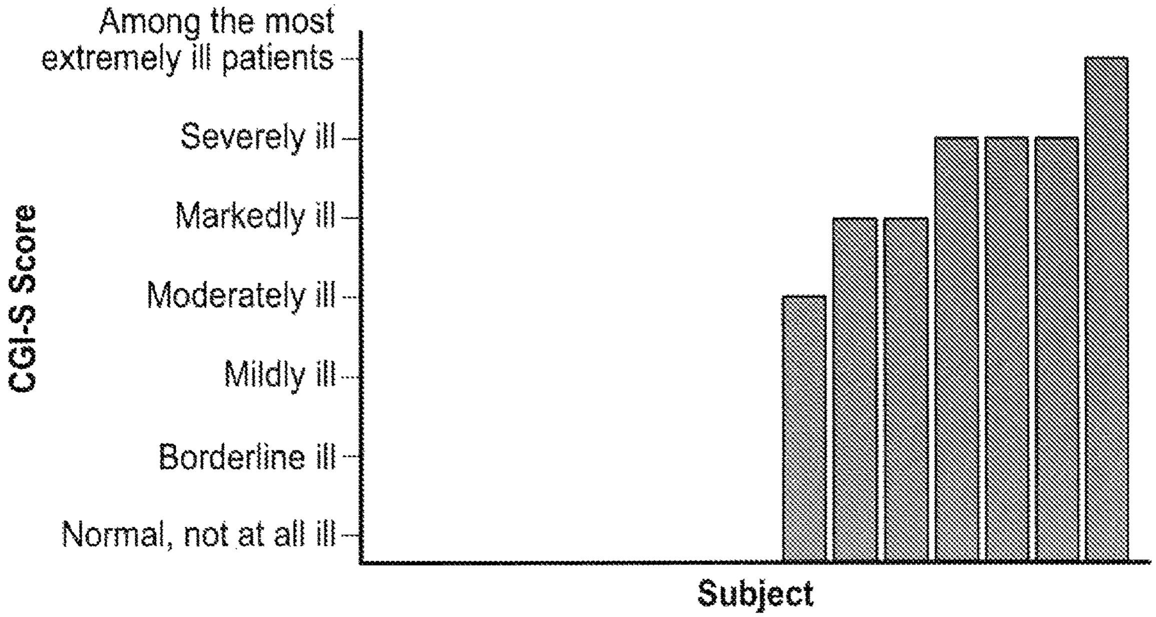
FIG. 14 is a graph illustrating the baseline Clinical Global Impressions of Change (CGI-C) scores observed by clinicians in the phase 1B study of radiprodil, as described in Example 9 below.

Global Impressions of Change: Baseline Clinical Global Impressions of Change (CGI-C) scores are shown in FIG. 14.

Figure 15:
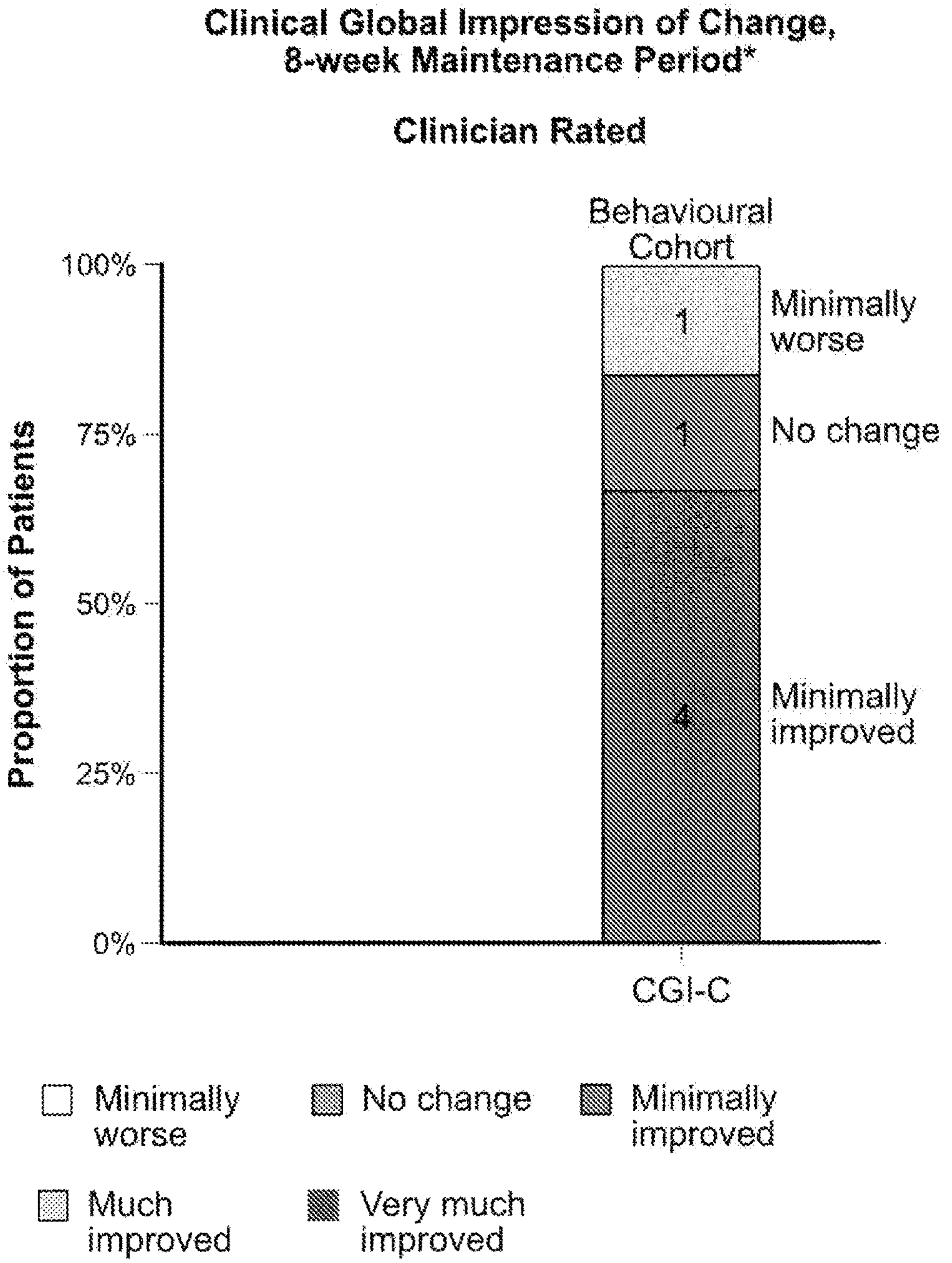
FIG. 15 is a graph illustrating the Clinical Global Impressions of Change (CGI-C) observed during the 8-week maintenance period of a phase 1B study of radiprodil, as described in Example 9 below.
Figure 16:
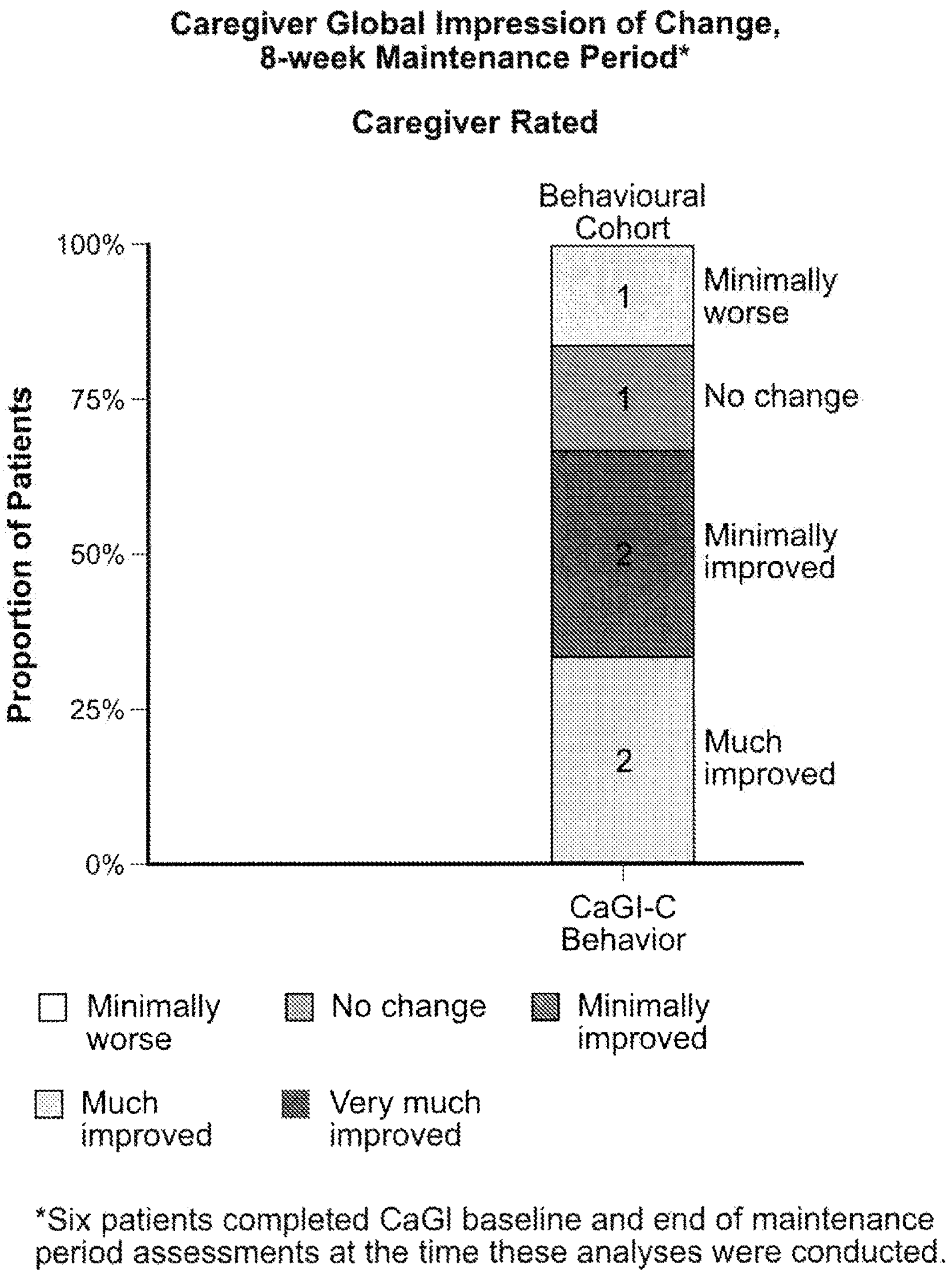
FIG. 16 is a graph illustrating the Caregiver Global Impressions of Change (CaGI-C) observed during the 8-week maintenance period of a phase 1B study of radiprodil, as described in Example 9 below.

Both clinicians and caregivers described clinical improvement in most patients over the course of the study using the Clinical Global Impressions of Change (CGI-C) and Caregiver Global Impressions of Change (CaGI-C), respectively (FIG. 15 and FIG. 16), regardless of the occurrence of CMS.

Conclusions: Radiprodil appeared to be generally well-tolerated in patients with GRIN-related neurodevelopmental disorder and GoF variants. Most common TEAEs were associated with infection or underlying disease symptoms. Both clinicians and caregivers described clinical improvement in most patients using the Clinical and Caregiver Global Impressions of Change Improvements. These results support advancing radiprodil into the next phase of development as a potential treatment for GRIN-related neurodevelopmental disorders.

Example 10. Preparation of Form a of Radiprodil

An exemplary preparation and characterization of radiprodil Form A is provided in US Publication No. 2012/0059034, which is incorporated herein by reference.

Example 11. Radiprodil Drug Granules

The formulation for pediatric use was developed as multiple unit oral dosage form. The approach was to develop a highly dispersible granule by wet granulation process in a fluid bed granulator to be reconstituted prior to administration.

Figure 17:
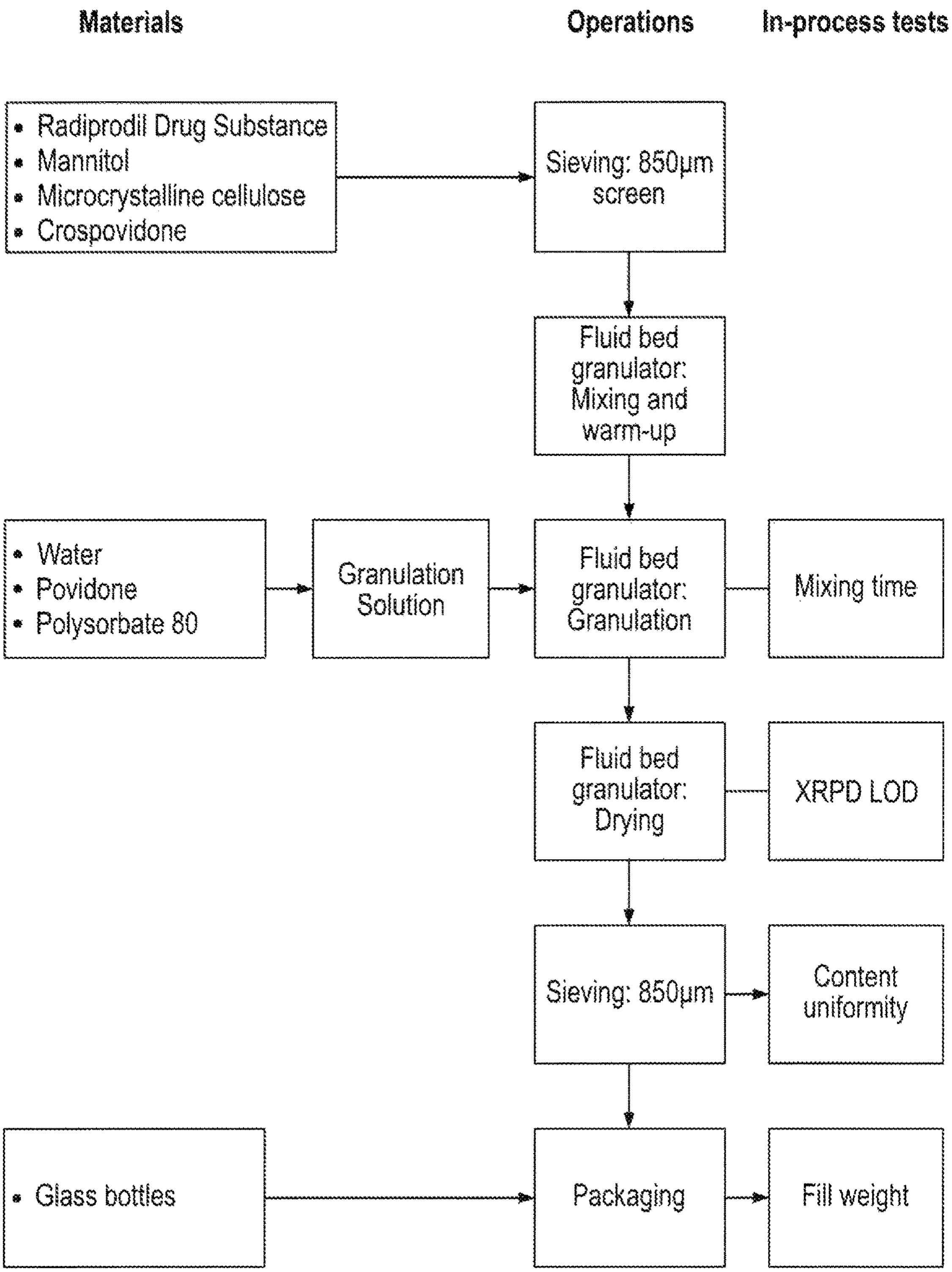
FIG. 17 depicts an exemplary manufacturing process of 30 weight % radiprodil granules.

The manufacturing process for Radiprodil granules for oral suspension described in Table 4 above consists of a granulation in a fluid bed granulator followed by a filling of the final granules in bottle. The Radiprodil granules are manufactured in accordance with current Good Manufacturing Practice (cGMP). The equipment described may be replaced by any equipment of similar performance. A flow diagram of the manufacturing process for Radiprodil granules for oral suspension is presented as FIG. 17.

Different granule prototypes were manufactured using different qualitative compositions in terms of filler, surfactant, binder and disintegrant, always using suitable excipients for pediatric formulation. During the formulation development, it has been observed that all the granule prototypes produced via fluid bed granulation were containing Form A of radiprodil. Therefore the manufacturing process was optimized to allow complete conversion of the dihydrate form to Form A through the drying step at the end of granulation process.

Scale-up of the granulation process in a fluid bed granulator was carried out and granules were manufactured at 1 kg scale. Process conditions were set with the aim to obtain full conversion of the dihydrate form (radiprodil drug substance) to Form A with a check of the XRPD pattern of the final granules. The trials demonstrated the feasibility of such a procedure to obtain a final product containing only the Form A.

Finally, one GMP batch at 30% drug loading was successfully manufactured at 1 kg scale for an ICH stability study by applying process conditions from scale-up trials.

Example 12. Impurity and Stability Analysis of Radiprodil Drug Granules

Impurities in the radiprodil drug substance and granules were analyzed.

HPLC-DAD method is used for the identification of radiprodil. The retention time and the DAD spectrum must have same features as the ones obtained with a reference standard of radiprodil.

An HPLC method is used for the assay of radiprodil and for the determination of the degradation products in Radiprodil granules for oral suspension. The quantification of the drug substance isperformed by comparing the peak areas of the sample with the corresponding peaks of the reference solution (external standard method). The quantification of the degradation products isperformed in area percentage taking the sum of all the peaks that are ≥0.05% and that are not contained in the chromatogram of the blank solution or coming from the excipients.

HPLC method is used to determine the level of the impurity 6-amino-2-benzoxazolone in radiprodil granules for oral suspension. The quantification is performed by comparing the peakarea of the sample with the peak of the reference solution (external standard method).

The potential and observed organic impurities in radiprodil drug substance batches are listed in Table 15.

TABLE 15

Impurities relating to radiprodil drug substance.

| Impurity | Structure/Formula/Molecular Weight | Source |
|---|---|---|
| Impurity 1 | 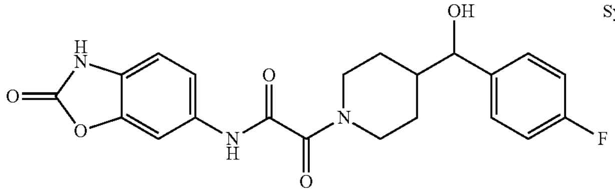 $C_{21}H_{20}FN_3O_5$ 413.41 | Synthesis |
| Impurity 2 | 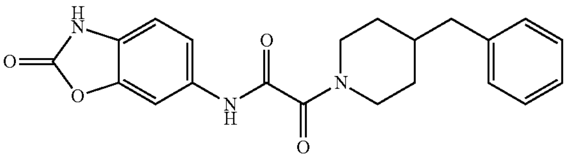 $C_{21}H_{21}N_3O_4$ 379.42 | Synthesis |
| Impurity 3 ([4-(4-Fluorobenzyl)-piperidin-1-yl]-oxo-acetic acid) | 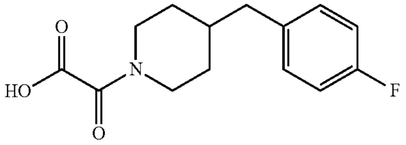 $C_{14}H_{16}FNO_3$ 265.29 | Starting Material |
| Impurity 4 (6-Amino-2-benzoxazolone) | 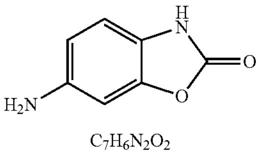 $C_7H_6N_2O_2$ 150.14 | Starting Material |

TABLE 15-continued

| Impurities relating to radiprodil drug substance. | | |
|---|---|---|
| Impurity | Structure/Formula/Molecular Weight | Source |
| Impurity 5 (6-Nitro-2-benzoxazolone) | 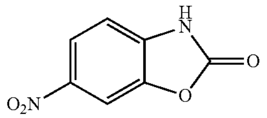 $C_7H_4N_2O_4$ 180.12 | Precursor of Starting Material |

Stability and impurity analyses of 30% granules, such as those described in Examples 11 and 12, and reconstituted formulations were studied. Table 16 displays stability data and impurity profiles for 30% radiprodil granules stored at 25° C./60% relative humidity (RH) at various time points. Table 17 displays stability data and impurity profiles for 30% radiprodil granules stored at 40° C./75% RH at various time points.

TABLE 16

| Stability Data for 30% Drug Loading Stored at 25° C./60% RH | | | | | | | |
|---|---|---|---|---|---|---|---|
| | Acceptance | Time points (months) | | | | | |
| Test | Criteria | 0 | 1 | 3 | 6 | 9 | 12 |
| Appearance | White to off-white granules | White powder | White granules | White granules | White granules | White granules | White granules |
| Assay | 90.0-110.0% of label claim | 98.7 | 100.7 | 99.5 | 99.2 | 97.5 | 99.4 |
| Water Content | Reported value (%) | 1.5 | 1.6 | 1.6 | 1.5 | 1.6 | 1.8 |
| Polymorph Confirmation XRPD on Granules | XRPD pattern consistent with the reference XRPD pattern | XRD pattern shows presence of radiprodil form A | XRD pattern shows presence of radiprodil form A and mannitol peaks | XRPD pattern consistent with T0 | XRD pattern shows presence of radiprodil form A and mannitol peaks | XRD pattern shows presence of radiprodil form A and mannitol peaks - | XRD pattern shows presence of radiprodil form A and mannitol peaks |
| | | | Impurities[a] | | | | |
| 6-Amino-2-benzoxazolinone | NMT 0.0074% w/w[c] | 0.00 | 0.00 | 0.00 | 0.00 | <0.001 | <0.001 |
| Hydroxy-RGH-896 | NMT 0.2% a/a | <0.05 | <0.05 | <0.05 | <0.05 | <0.05 | <0.05 |
| Piperidinyl-oxo-acetic acid | NMT 0.2% a/a | <0.05 | <0.05 | <0.05 | <0.05 | <0.05 | <0.05 |
| Desfluoro-RGH-896 | NMT 0.2% a/a | <0.05 | <0.05 | <0.05 | <0.05 | <0.05 | <0.05 |
| Individual Unspecified | NMT 0.2% a/a | <0.05 | <0.05 | <0.05 | <0.05 | <0.05 | <0.05 |
| Total unspecified | NMT 1.0% a/a | <0.05 | <0.05 | <0.05 | <0.05 | <0.05 | <0.05 |
| Total[b] | NMT 2.5% a/a | <0.05 | <0.05 | <0.05 | <0.05 | <0.05 | <0.05 |
| | | | Dissolution | | | | |
| Low volume | Q = 80% at | 95 | 98 | 98 | 97 | 97 | 93 |
| High volume | 30 minutes | 96 | 96 | 98 | 97 | 95 | 95 |

[a] = Impurities are expressed in % claim

[b] = 6- amino-2-benzoxazolinone not included in Total Impurities calculation

[c] = the acceptance criteria has been lowered from NMT 0.2% w/w to NMT 0.0074% w/w from timepoint 9-month timepoint

TABLE 17

| Stability Data for 30% Drug Loading Stored at 40° C./75% RH | | | | | |
|---|---|---|---|---|---|
| | Acceptance | Time points (months) | | | |
| Test | Criteria | 0 | 1 | 3 | 6 |
| Appearance | White to off-white granules | White granules | White granules | White granules | White granules |
| Assay | 90.0-110.0% of label claim | 98.7 | 100.5 | 103.2 | 101.2 |
| Water Content | Reported value (%) | 1.5 | 1.7 | 1.9 | 2.2 |
| Polymorph Confirmation XRPD on Granules | XRPD pattern consistent with the reference XRPD pattern | XRD pattern shows presence of radiprodil form A | XRD pattern shows presence of radiprodil form A and mannitol peaks | XRPD pattern consistent with T0 | XRD pattern shows presence of radiprodil form A and mannitol peaks |
| Impurities[a] | | | | | |
| 6-Amino-2-benzoxazolinone | NMT 0.2% w/w | 0.00 | 0.00 | 0.00 | 0.00 |
| Hydroxy-RGH-896 | NMT 0.2% a/a | <0.05 | <0.05 | <0.05 | <0.05 |
| Piperidinyl-oxo-acetic acid | NMT 0.2% a/a | <0.05 | <0.05 | <0.05 | <0.05 |
| Desfluoro-RGH-896 | NMT 0.2% a/a | <0.05 | <0.05 | <0.05 | <0.05 |
| Individual Unspecified | NMT 0.2% a/a | <0.05 | <0.05 | <0.05 | <0.05 |
| Total unspecified | NMT 1.0% a/a | <0.05 | <0.05 | <0.05 | <0.05 |
| Total[b] | NMT 2.5% a/a | <0.05 | <0.05 | <0.05 | <0.05 |
| Dissolution | | | | | |
| Low volume | | 95 | 99 | 95 | 94 |
| High volume | Q = 80% at 30 minutes | 96 | 94 | 94 | 95 |

[a] = Impurities are expressed in % claim
[b] = 6- amino-2-benzoxazolinone not included in Total Impurities calculation
NMT = not more than

Example 13. Dissolution Profiles of Radiprodil Compositions

This study summarizes dissolution experiments preformed on the radiprodil drug substance and on the drug product including two drug loadings with and without reconstitution in SYRSPEND® and water prior to the dissolution test.

All dissolution experiments were performed on six vessels and the comparative curves were plotted using the average of them.

Some dissolution experiments were performed using prior to the dissolution a reconstitution in Syrpend® and water. In that case, the reconstitution was prepared and let under stirring for 1 night prior to the dissolution test. In order to mimic the clinical pharmacy manual, an additional test was performed with an extemporaneous suspension (15 min under stirring prior to the dissolution).

Dissolution and high performance liquid chromatography (HPLC) parameters used in the experiments are provided below in Tables 18 and Table 19, respectively.

TABLE 18

| Dissolution Parameters | |
|---|---|
| Description | Value |
| Apparatus | USPII (paddle apparatus) |
| Dissolution medium | Buffer 15 mM Sodium Phosphate pH 6.8 + 0.5% SLS |
| Dissolution medium volume (mL) | 2000 for 19 ml 30% granules suspension |
| Dissolution medium temperature (° C.) | 37 +/−0.5° C. |
| Rotation speed (rpm) | 50 |
| Sampling time (min) | 5, 10, 15, 30, 45 and 60 (infinity point at 250 rpm) mins |
| Sampling volume (mL) | 1 mL (5 mL withdrawn; 4 mL |
| Separative technique | discarded back into the vessel) |

TABLE 19

| HPLC Parameters | |
|---|---|
| Description | Value |
| Column type | Symmetry Shield RP-18 (15 mm * 4.6 mm − 3.5 μm) |
| Mobile phase | Mix of phase A/phase B = 45/55% v/v |

TABLE 19-continued

| HPLC Parameters | |
|---|---|
| Description | Value |
| Mobile phase (phase A) | Water/Acetonitrile (ACN)/1M TEAP (900:90:10 v/v/v) |
| Mobile phase (phase B) | Water/ACN/1M TEAP (90:900:10 v/v/v) |
| Flow rate (mL/min) | 1.0 |
| Column temperature (° C.) | 30 |
| Detector type | UV |
| Wavelength (nm) | 255 |
| Injection volume (μL) | 20 |

Dissolution experiments without reconstitution in SYRSPEND ® SF and water prior to the dissolution tests.

Figure 18:
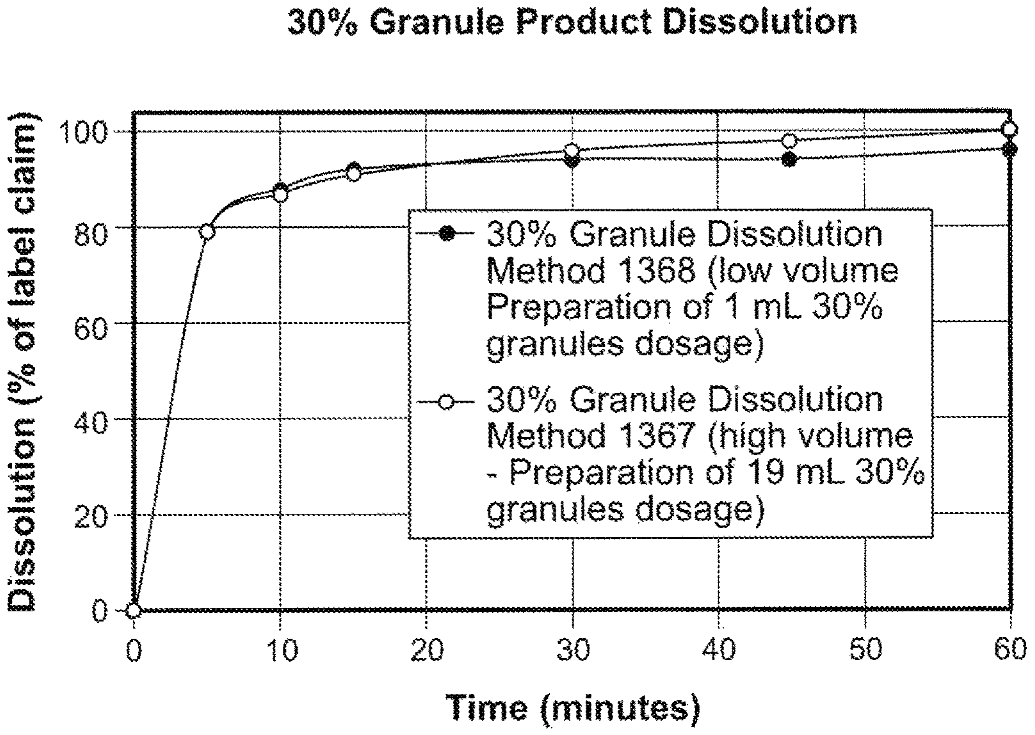
FIG. 18 depicts dissolution profiles for 30% granule radiprodil samples prepared in high volume and low volume.

Exemplary dissolution profiles of 30% granule product are provided in FIG. 18.

Example 14. Preparation of Form C of Radiprodil

An exemplary preparation and characterization of radiprodil Form C is provided in US Publication No. 2012/0010044, which is incorporated herein by reference.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of treating a GRIN-related neurodevelopmental disorder in a subject in need thereof, the method comprising orally administering to the subject a pharmaceutical composition comprising: (i) an anhydrous crystalline form of a compound of Formula I:

Formula I

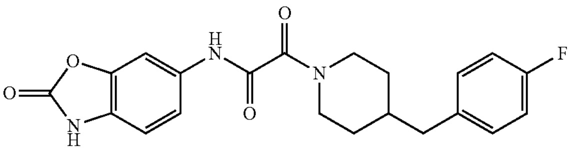

wherein the anhydrous crystalline form (Form A) has an X-ray powder diffraction pattern with characteristic peaks between and including the following values of 2θ in degrees: 7.8, 22.0, 23.7, 27.0 and 27.6±0.2° 2θ, and (ii) a pharmaceutically acceptable excipient;

wherein orally administering comprises:

(i) a titration dose comprising:

orally administering the pharmaceutical composition to the subject in an amount sufficient to provide the subject 0.05 mg/kg to about 1.0 mg/kg of the compound twice a day;

and (ii) a maintenance dose comprising:

orally administering the pharmaceutical composition to the subject in an amount sufficient to provide the subject about 0.5 mg/kg to about 1.0 mg/kg of the compound twice a day.

2. The method of claim 1, wherein the subject is a pediatric subject.

3. The method of claim 1, wherein the subject is suffering from tuberous sclerosis complex.

4. The method of claim 1, wherein the subject is suffering from focal cortical dysplasia.

5. The method of claim 1, wherein the subject has been identified as having a GRIN mutation.

6. The method of claim 5, wherein the mutation is a GRIN2A gain-of-function mutation, a GRIN2B gain-of-function mutation, a GRIN1 gain-of-function mutation, or a GRIN2D gain-of-function mutation.

7. The method of claim 1, wherein the compound is orally administered to the subject within one to four hours of the subject eating food.

8. The method of claim 7, wherein the compound is orally administered to the subject within one to four hours of the subject eating a high-fat meal.

9. The method of claim 7, wherein the compound is orally administered to the subject within two hours of the subject eating food.

10. The method of claim 1, wherein the pharmaceutical composition comprises: about 30% by weight of the anhydrous crystalline form of the compound based on the total weight of the pharmaceutical composition.

11. The method of claim 1, wherein the titration dose comprises:

orally administering the pharmaceutical composition to the subject in an amount sufficient to provide the subject 0.125 mg/kg to 1.0 mg/kg twice a day.

12. The method of claim 1, wherein the titration dose comprises:

orally administering the pharmaceutical composition to the subject in an amount sufficient to provide the subject 0.125 mg/kg to 0.75 mg/kg twice a day.

13. The method of claim 1, wherein the maintenance dose comprises:

orally administering the pharmaceutical composition to the subject in an amount sufficient to provide the subject 1.0 mg/kg of the compound twice a day.

14. The method of claim 1, wherein the maintenance dose comprises:

orally administering the pharmaceutical composition to the subject in an amount sufficient to provide the subject 0.75 mg/kg of the compound twice a day.

15. The method of claim 12, wherein the maintenance dose comprises:

orally administering the pharmaceutical composition to the subject in an amount sufficient to provide the subject 0.75 mg/kg of the compound twice a day.

16. A method of treating a subject with a GRIN-related neurodevelopmental disorder, the method comprising administering to the subject a pharmaceutical composition comprising:

(i) an anhydrous crystalline form of a compound of Formula I:

Formula I

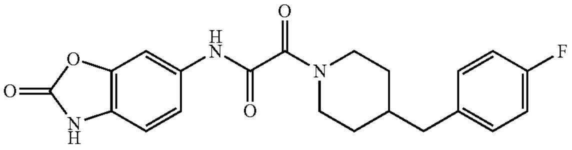

wherein the anhydrous crystalline form (Form A) has an X-ray powder diffraction pattern with characteristic peaks between and including the following values of 2θ in degrees: 7.8, 22.0, 23.7, 27.0 and 27.6±0.2° 2θ, and (ii) a pharmaceutically acceptable excipient, wherein the composition is orally administered to the subject, within four hours of eating food, in an amount sufficient to provide a titration dose of the compound twice a day followed by a maintenance dose of the compound twice a day; wherein:

the titration dose is 0.05 mg/kg to about 0.75 mg/kg of the compound; and the maintenance dose is about 0.75 mg/kg of the compound.

17. The method of claim 16, wherein the compound is orally administered to the subject within two hours of the subject eating food.

18. The method of claim 16, wherein the subject has been identified as having a GRIN mutation.

19. The method of claim 16, wherein the subject is a pediatric subject.

20. The method of claim 16, wherein the titration dose is 0.125 mg/kg to 0.75 mg/kg of the compound.

21. The method of claim 20, wherein the maintenance dose is 0.75 mg/kg of the compound.

22. The method of claim 16, wherein the pharmaceutical composition comprises: about 30% by weight of the anhydrous crystalline form of the compound based on the total weight of the pharmaceutical composition.

23. A method of treating a GRIN-related neurodevelopmental disorder in a subject in need thereof, the method comprising orally administering to the subject a pharmaceutical composition comprising: (i) an anhydrous crystalline form of a compound of Formula I:

Formula I

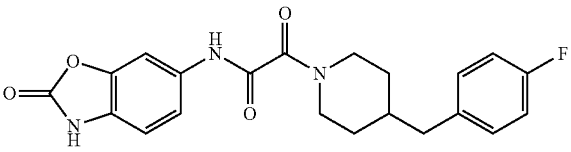

wherein the anhydrous crystalline form (Form A) has an X-ray powder diffraction pattern with characteristic peaks between and including the following values of 2θ in degrees: 7.8, 22.0, 23.7, 27.0 and 27.6±0.2° 2θ, and (ii) a pharmaceutically acceptable excipient;

wherein the composition is orally administered to the subject within one to four hours of the subject eating food, wherein orally administering comprises:

(iii) a titration dose comprising:

orally administering the pharmaceutical composition to the subject in an amount sufficient to provide the subject 0.05 mg/kg to about 1.0 mg/kg of the compound twice a day;

and (iv) a maintenance dose comprising:

orally administering the pharmaceutical composition to the subject in an amount sufficient to provide the subject about 0.5 mg/kg to about 1.0 mg/kg of the compound twice a day.

24. The method of claim 23, wherein the subject has been identified as having a GRIN mutation.

25. The method of claim 24, wherein the mutation is a GRIN2A gain-of-function mutation, a GRIN2B gain-of-function mutation, a GRIN1 gain-of-function mutation, or a GRIN2D gain-of-function mutation.

26. The method of claim 23, wherein the subject is a pediatric subject.

27. A method of treating a subject with a GRIN-related neurodevelopmental disorder, the method comprising administering to the subject a pharmaceutical composition comprising:

(i) an anhydrous crystalline form of a compound of Formula I:

Formula I

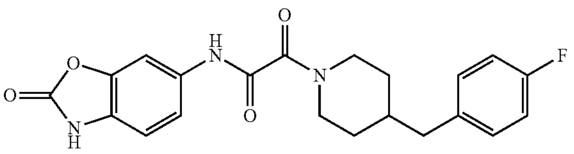

wherein the anhydrous crystalline form (Form A) has an X-ray powder diffraction pattern with characteristic peaks between and including the following values of 2θ in degrees: 7.8, 22.0, 23.7, 27.0 and 27.6±0.2° 2θ, and (ii) a pharmaceutically acceptable excipient, wherein the composition comprises about 30% by weight of the anhydrous crystalline form of the compound based on the total weight of the pharmaceutical composition, and wherein the composition is orally administered to the subject in an amount sufficient to provide a titration dose of the compound twice a day followed by a maintenance dose of the compound twice a day; wherein:

the titration dose is about 0.05 mg/kg to about 1 mg/kg of the compound.

28. The method of claim 27, wherein the subject is a pediatric subject.

29. The method of claim 27, wherein the subject has been identified as having a GRIN mutation.

30. The method of claim 29, wherein the mutation is a GRIN2A gain-of-function mutation, a GRIN2B gain-of-function mutation, a GRIN1 gain-of-function mutation, or a GRIN2D gain-of-function mutation.

* * * * *